(12) United States Patent
Epperly et al.

(10) Patent No.: US 10,251,860 B2
(45) Date of Patent: Apr. 9, 2019

(54) COMPOUNDS FOR BONE HEALING

(71) Applicants: University of Pittsburgh—Of the Commonwealth System of Higher Education, Pittsburgh, PA (US); The Brigham and Women's Hospital, Inc., Boston, MA (US)

(72) Inventors: Michael W. Epperly, Pittsburgh, PA (US); Joel S. Greenberger, Sewickley, PA (US); Peter Wipf, Pittsburgh, PA (US); Julianne Glowacki, Boston, MA (US)

(73) Assignees: University of Pittsburgh—of the Commonwealth System of Higher Education, Pittsburgh, PA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 15/906,856

(22) Filed: Feb. 27, 2018

(65) Prior Publication Data

US 2018/0185322 A1 Jul. 5, 2018

Related U.S. Application Data

(63) Continuation of application No. PCT/US2016/049505, filed on Aug. 30, 2016.

(60) Provisional application No. 62/212,283, filed on Aug. 31, 2015.

(51) Int. Cl.
| | |
|---|---|
| *A61P 19/00* | (2006.01) |
| *A61P 19/10* | (2006.01) |
| *A61K 31/337* | (2006.01) |
| *C07D 305/06* | (2006.01) |

(52) U.S. Cl.
CPC ........... *A61K 31/337* (2013.01); *A61P 19/00* (2018.01); *A61P 19/10* (2018.01); *C07D 305/06* (2013.01)

(58) Field of Classification Search
CPC .............................. A61K 31/337; A61P 31/10
USPC ...................................................... 514/449
See application file for complete search history.

(56) References Cited

U.S. PATENT DOCUMENTS

| | | | |
|---|---|---|---|
| 8,288,551 B2 | 10/2012 | Wipf et al. | |
| 8,748,369 B2 | 6/2014 | Epperly et al. | |
| 9,200,035 B2* | 12/2015 | Wipf | ...................... C07D 405/14 |
| 9,546,144 B2* | 1/2017 | Wipf | ...................... C07D 405/14 |
| 9,676,738 B2* | 6/2017 | Wipf | ...................... C07D 305/08 |
| 2010/0035869 A1 | 2/2010 | Wipf et al. | |
| 2014/0256654 A1 | 9/2014 | Wipf et al. | |

FOREIGN PATENT DOCUMENTS

| | | |
|---|---|---|
| WO | WO 2010/009389 | 1/2010 |
| WO | WO 2010/009405 | 1/2010 |
| WO | WO 2013/059651 | 4/2013 |

OTHER PUBLICATIONS

International Search Report dated Oct. 19, 2012, from International Application No. PCT/US2012/061109.
International Search Report dated Dec. 18, 2016, from International Application No. PCT/US2016/049505.
Kalash et al., "Amelioration of Radiation-Induced Pulmonary Fibrosis by a Water-Soluble Bifunctional Sulfoxide Radiation Mitigator (MMS350)," *Radiation Research* 180(5):474-490, 2013.
Shinde et al., "Effects of the Bifunctional Sulfoxide MMS350, a Radiation Mitigator, on Hematopoiesis in Long-term Bone Marrow Cultures and on Radioresistance of Mrarow Stromal Cell Lines," *In Vivo* 28(4):457-466, 2014.
Skoda et al., "An Uncharged Oxetanyl Sulfoxide as a Covalent Modifier for Improving Aqueous Solubility," *ACS Medical Chemistry Letters* 5(8):900-904, 2014.
Sprachman et al., "A Bifunctional Dimethylsulfoxide Substitute Enhances the Aqueous Solubility of Small Organic Molecules," *Assay and Drug Development Technologies* 10(2):269-277, Jun. 2012.
Wuitschik et al., "Oxetanes in Drug Discovery: Structural and Synthetic Insights," *Journal of Medical Chemistry* 53(8):3227-3246, 2010.

\* cited by examiner

*Primary Examiner* — Kevin E Weddington
(74) *Attorney, Agent, or Firm* — Klarquist Sparkman, LLP

(57) ABSTRACT

Disclosed herein are embodiments of a method of accelerating bone healing in a subject in need thereof, comprising administering to the subject a compound disclosed here. The method may further comprise selecting or identifying a subject that has bone damage, or is a risk of developing bone damage. The compound may be administered after bone damage has occurred, or it may be administered prophylactically. The compound may be administered to a subject that has not and/or will not be exposed to radiation. In other embodiments, the subject has been and/or will be exposed to radiation.

19 Claims, 41 Drawing Sheets

| Condition | $D_0$ (Gy) | ñ |
|---|---|---|
| C57BL/6 | $1.9 \pm 0.1$ | $5.8 \pm 1.1$ |
| C57BL/6 + MMS350 Pre | $1.7 \pm 0.2$ | $15.8 \pm 2.9$ (p = 0.0039) |
| C57BL/6 + MMS350 Post | $2.4 \pm 0.3$ (p = 0.0444) | $3.5 \pm 0.3$ | acute phase latent period

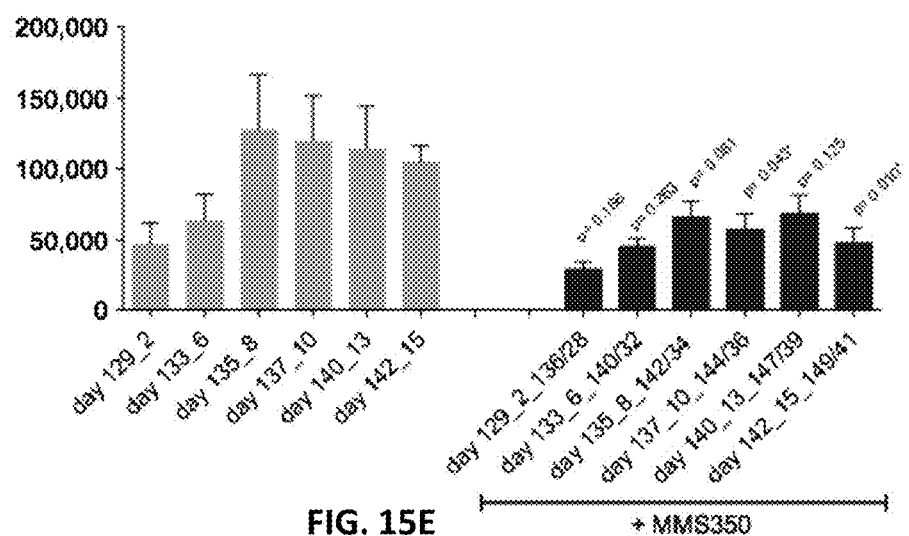
FIG. 15E  + MMS350
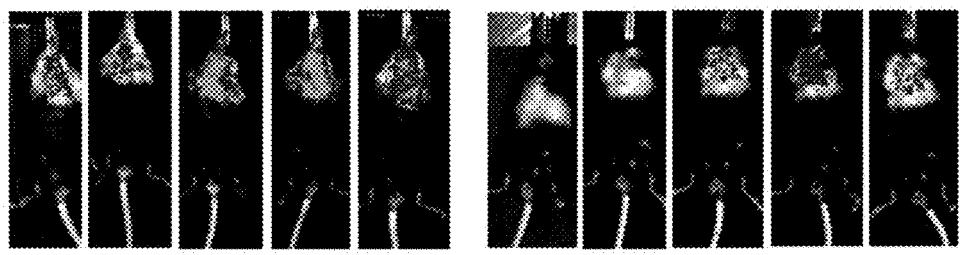
late reaction phase
FIG. 15F acute phase latent period late reaction phase

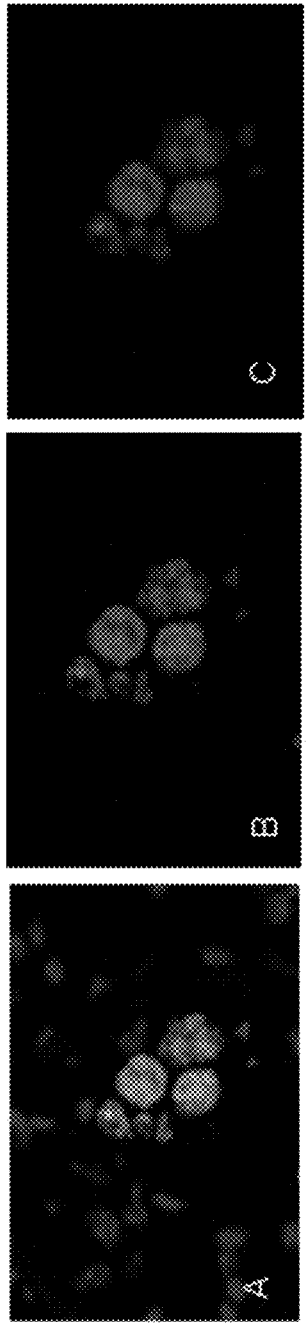

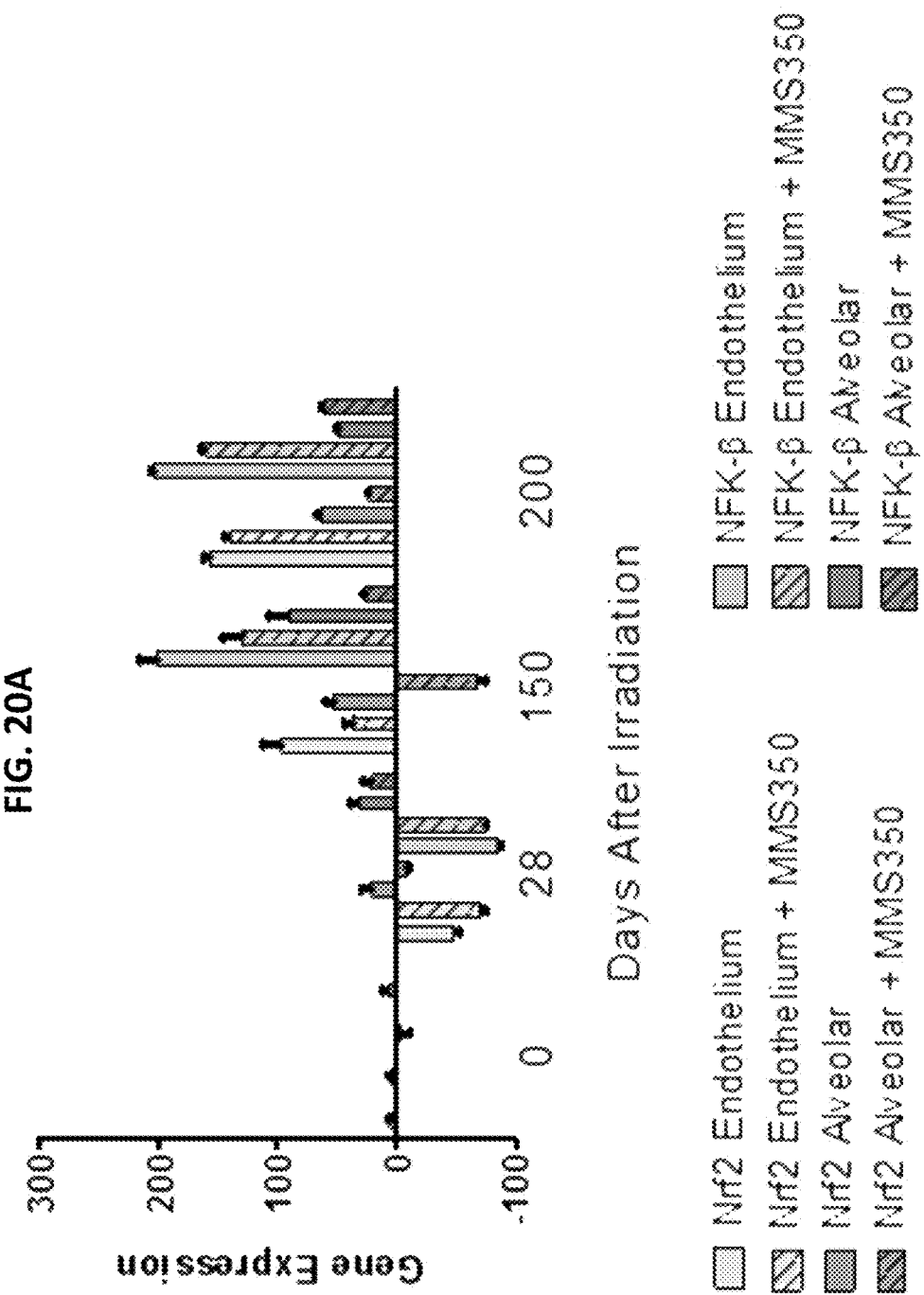

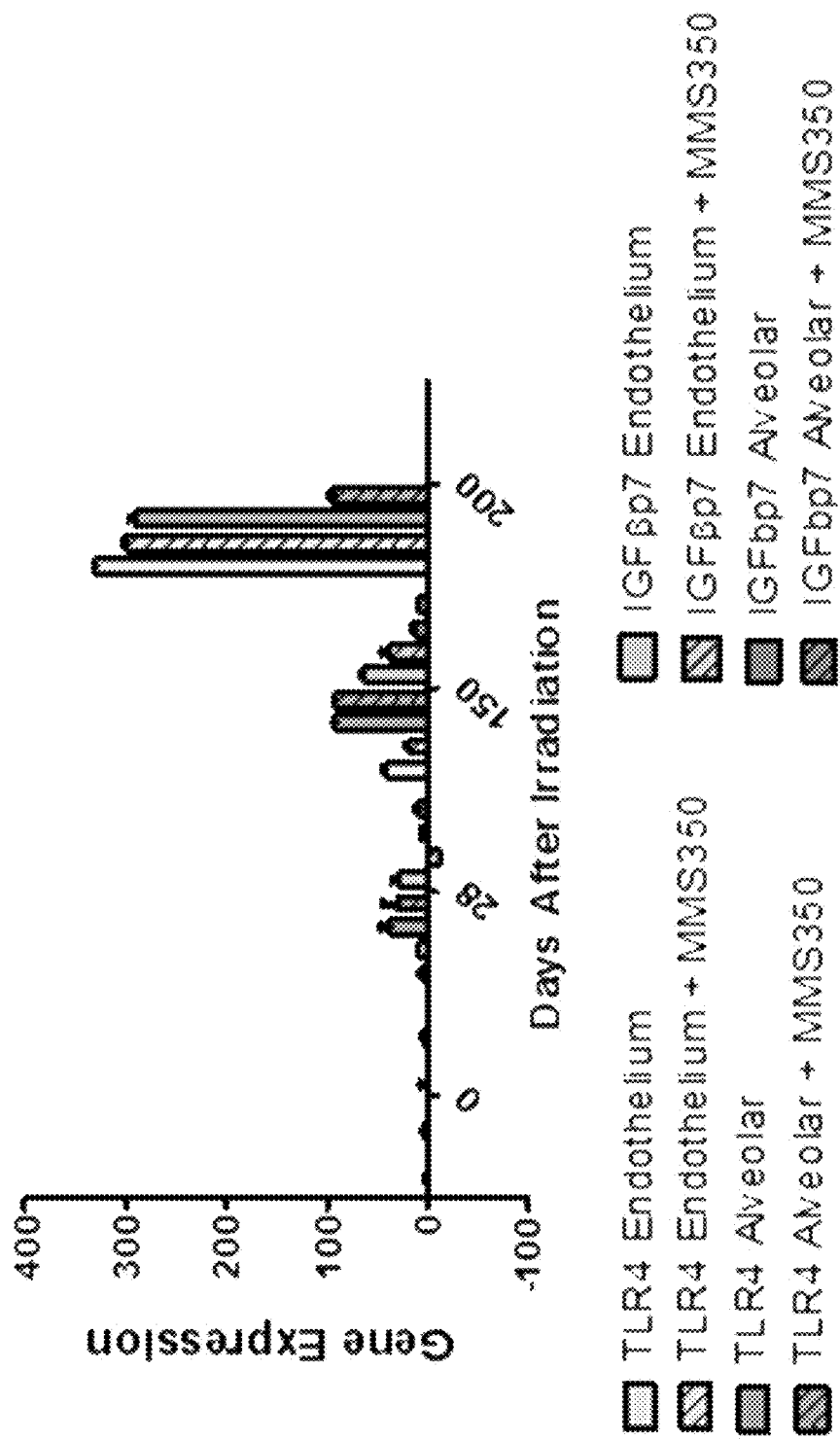

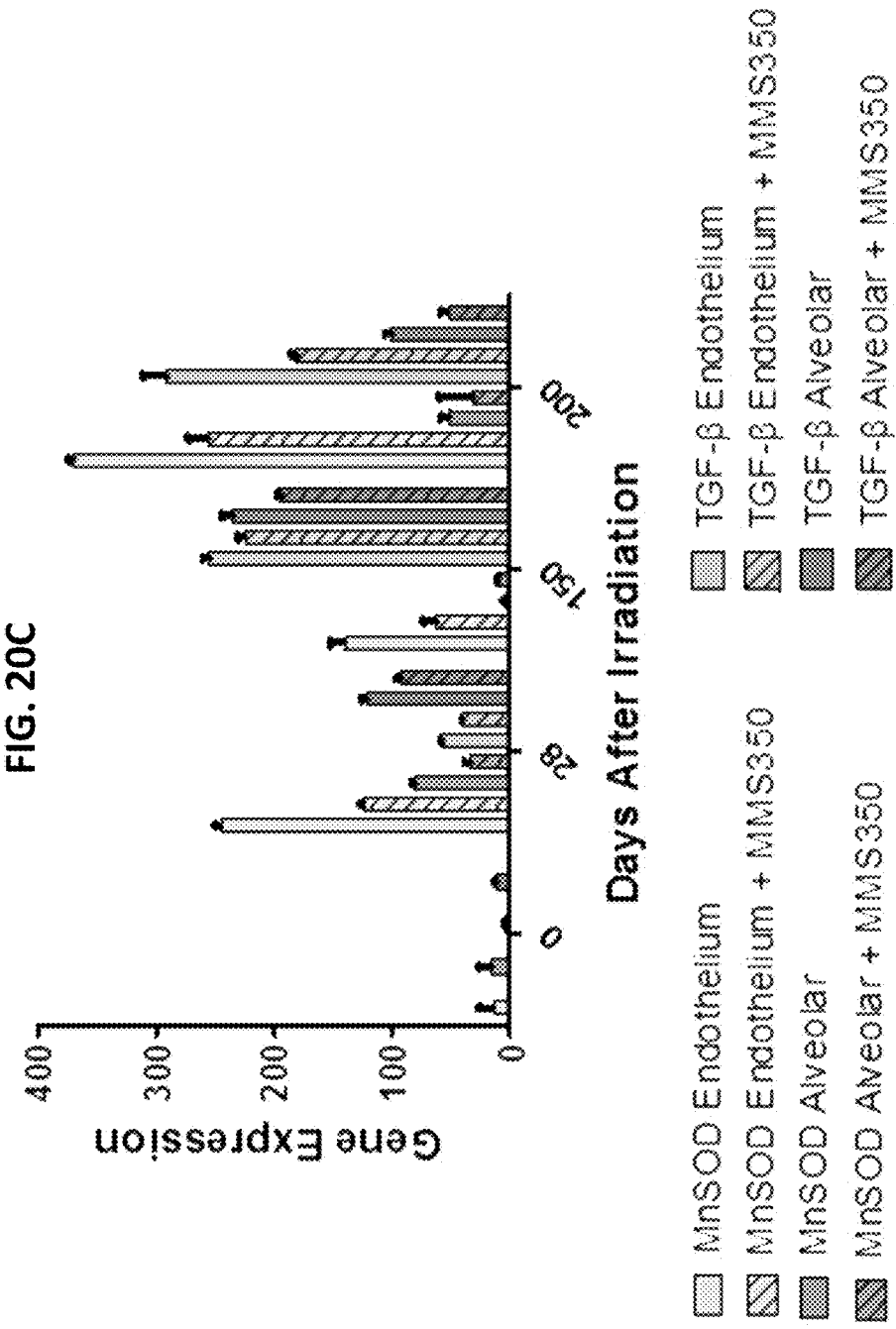

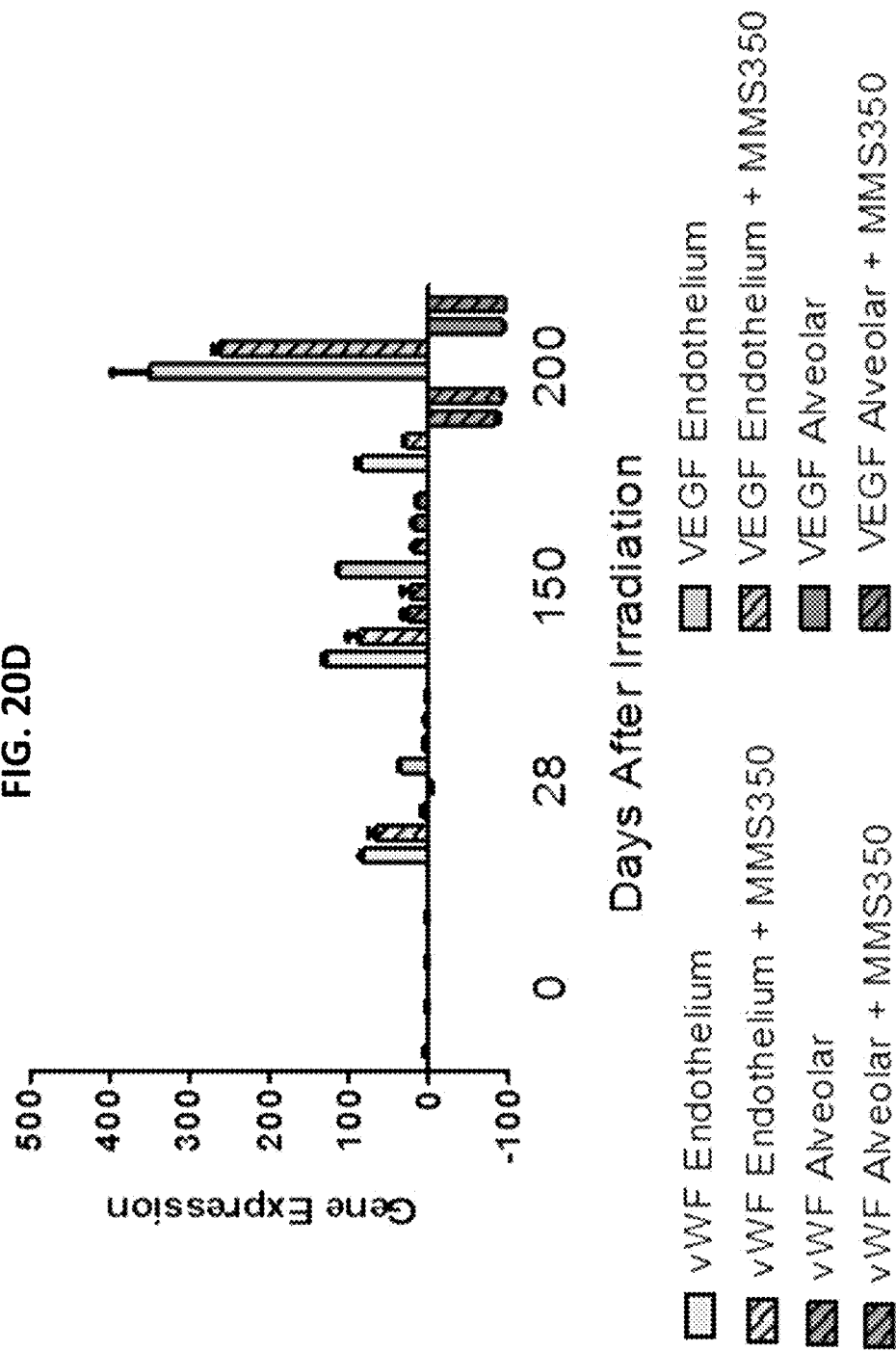

Whole Lung

Endothelial Cells

| Conditioned medium source | Average motility (µm/min) |
|---|---|
| control medium | 7.95 ± 0.19<br>n=273 |
| endothelial cells | 7.97 ± 0.67<br>n=244<br>p=0.975 |
| type II alveolar cells | 7.25 ±0.13 n=244<br>p=0.093 |
| irradiated endothelial cells | 7.84 ± 0.51<br>n=270<br>p=0.864 |
| irradiated type II alveolar cells | 7.55 ± 0.43<br>n=248<br>p=0.476 |

Azetidine Synthesis:

US 10,251,860 B2

COMPOUNDS FOR BONE HEALING

CROSS REFERENCE TO RELATED APPLICATION

This is a continuation of International Application No. PCT/US2016/049505, filed on Aug. 30, 2016, which was published in English under PCT Article 21(2), and which in turn claims the benefit of the earlier filing date of U.S. provisional patent application No. 62/212,283, filed on Aug. 31, 2015, each of which is incorporated herein by reference in its entirety.

ACKNOWLEDGMENT OF GOVERNMENT SUPPORT

This invention was made with government support under grant No. U19-A1068021 awarded by the National Institutes of Health/National Institute of Allergy and Infectious Disease. The government has certain rights in the invention.

FIELD

The present disclosure concerns a method of accelerating bone healing, bone growth, bone reconstruction, or bone repair in a subject.

BACKGROUND

In both the field of development of radiation counter measures for large population administration as a radiation counter measure and in the field of development of normal tissue radiation protectors for clinical radiotherapy, interest in new small molecule modifiers of irradiation induced cellular tissue and organ damage has gained prominence in recent years. Reports of effective small molecule irradiation mitigators have included the GS-nitroxides, triphenylphosphonium conjugated Imidazole Fatty Acids, phospho-inositol-3 kinase inhibitors, and a variety of other small molecules which inhibit ionizing radiation induced apoptosis. Delivery of these small molecules at 24 hours or later after total body irradiation has proven effective in animal models of total body irradiation and in some cases, as with GS-nitroxides, has been effective in multiple organ specific administration protocols for protection of the esophagus and skin from ionizing irradiation damage.

A challenge for the development of small molecule irradiation mitigators has been design and implementation of a non-toxic and reliable delivery system. Relative insolubility of many new small molecule radiation mitigators has required administration by intravenous, intra-peritoneal, or other systemic delivery systems. Delivery formulations have required liposomal or other solvent systems that have been unsuitable for oral administration.

In addition, modern drug development relies on high-throughput screening assays. Often, these trials use compound libraries stored in solution for periods of several months to as long as three years. DMSO 1 has been used as the storage solvent of choice, but problems, including compound degradation and precipitation, are frequently encountered. In one case study, qualitative compound precipitation was observed in 26% of test plates. Systematic studies of compound degradation in DMSO have indicated that approximately 50% of samples degraded over a period of 12 months when stored in anhydrous DMSO at ambient temperature. Compound storage problems are augmented by low hydrophilicity, since a large portion of screening libraries is composed of compounds designed for enhanced membrane permeability. The trend toward lipophilic, higher molecular weight compounds results in libraries of materials with lower intrinsic aqueous solubilities. Current estimates state that 30-50% of compounds in screening libraries have aqueous solubilities of less than 10 μM. These lipophilic molecules are more likely to precipitate from DMSO stock solutions, leading to erroneously low assay concentrations when using the DMSO stock for sample preparation. Additionally, poor aqueous solubility causes precipitation from aqueous media after dilution of DMSO stock solutions. When compound concentrations in assay media fall below calculated concentrations, flawed conclusions regarding toxicity, efficacy, or structure-activity relationships are drawn.

Aqueous dissolution of problematic compounds can be enhanced by salt formation, or chemical modification of the substrate (formation of pro-drugs). If these methods are not applicable, complexing agents or cosolvents can be added to aid in dissolution. Some examples include cyclodextrins, dendrimers, low molecular weight PEG's (polyethylene glycols, e.g., PEG 400), and solvents such as glycerin and NMP (A-methyl pyrrolidone). Other solubilizing agents have designs based on DMSO; one example is a polymeric sulfoxide derived from poly-L-methionine 2 (FIG. 1).

SUMMARY

Disclosed herein are compounds of formulae I-VI as described below.

Also disclosed herein are methods of treating or preventing radiation-induced damage in a subject, comprising administering to the subject a therapeutically effective amount of at least one compound of formulae I-VI.

Also disclosed herein are methods for increasing solubility of an organic compound in an aqueous medium, comprising including in the aqueous medium a compound that includes an oxetane moiety.

A method for accelerating bone healing is also disclosed herein. The method may comprise selecting a subject that has or is at increased risk of developing bone damage, and administering a disclosed compound to the subject to accelerate bone healing, bone growth, bone reconstruction, or bone repair.

The foregoing will become more apparent from the following detailed description, which proceeds with reference to the accompanying figures.

BRIEF DESCRIPTION OF THE DRAWINGS

FIG. 10A is a graph of number of cells versus radiation dose, illustrating the number of cell counted on day 3 of the experiment.

FIG. 10B is a graph of viability versus radiation dose, illustrating the viability of cells at different radiation doses on day 3 of the experiment.

FIG. 10C is a graph of number of cells versus radiation dose, illustrating the number of cell counted on day 5 of the experiment.

FIG. 10D is a graph of viability versus radiation dose, illustrating the viability of cells at different radiation doses on day 5 of the experiment.

FIG. 15 provide data illustrating that the pulmonary migration of luc+ stromal cells to lungs of irradiated mice is reduced by MMS350. C57BL/6NTac mice were irradiated to 20 Gy to the pulmonary cavity. The mice were shielded so that only the pulmonary cavity was irradiated. On day 88 after irradiation, half of the mice were placed on 100 mM MMS350 in drinking water. In subgroups, at day: 3, 50, or 100 after irradiation, mice were injected intraperitoneally with $1 \times 10^6$ cells of a clonal bone marrow stromal cell line derived from a luciferase+ transgenic mouse.

FIG. 15E is a graph illustrating that by 129 days post 20Gy thoracic irradiation (the late reaction phase), migration of luc+ BM stromal cells to the lungs was significant. Mice on MMS350 in drinking water displayed a significant decrease in pulmonary migration of luc+ bone marrow stromal cells compared to control mice.

FIG. 15F is a photograph of the in vivo images corresponding to the data presented in FIG. 15E.

FIGS. 17A-17C are photographs illustrating the cell division of luciferase positive bone marrow stromal cell line migrating to lungs.

FIG. 17A is a photograph illustrating dual stained lung sections demonstrating simultaneously stained luc+ and BrdU+ cells (yellow).

FIG. 17B is a photograph illustrating just the luc+ stained cells from FIG. 17A (green).

FIG. 17C is a photograph illustrating just the BrdU+ stained cells from FIG. 17A (red).

FIGS. 20A-20D provide data illustrating that MMS350 decreases levels of irradiation induced endothelial and alveolar cell specific RNA levels. Endothelial and alveolar cells were isolated from the lungs of irradiated control or MMS350 treated mice at days 0, 29, 150, and 200 after 20 Gy thoracic irradiation. Subgroups of mice had received MMS350 continuously in the drinking water beginning 7 days before irradiation. RNA was isolated and RT-PCR was performed for gene expression for various markers. Gene expression that was increased by lung irradiation in endothelial cells was decreased in mice treated with MMS350 in the drinking water compared to the effect on pulmonary genes associated with irradiated alveolar cells.

FIG. 20A is a graph of gene expression versus days after irradiation illustrating the gene expression for oxidative stress induced promoters.

FIG. 20B is a graph of gene expression versus days after irradiation illustrating the gene expression for endothelial and alveolar cell markers.

FIG. 20C is a graph of gene expression versus days after irradiation illustrating the gene expression for fibrosis associated genes.

FIG. 20D is a graph of gene expression versus days after irradiation illustrating the gene expression for endothelial cell markers.

FIG. 21A is a graph of gene expression versus days after irradiation illustrating the expression of BD1, BD2, BD3, and BRDT from mRNA extracted from the total lungs.

FIG. 21B is a graph of gene expression versus days after irradiation illustrating the expression of BD1, BD2, BD3, and BRDT from mRNA extracted from endothelial cells.

FIG. 21C is a graph of gene expression versus days after irradiation illustrating the expression of BD1, BD2, BD3, and BRDT from mRNA extracted from alveolar II cells.

DETAILED DESCRIPTION

Terminology

Figure 1:
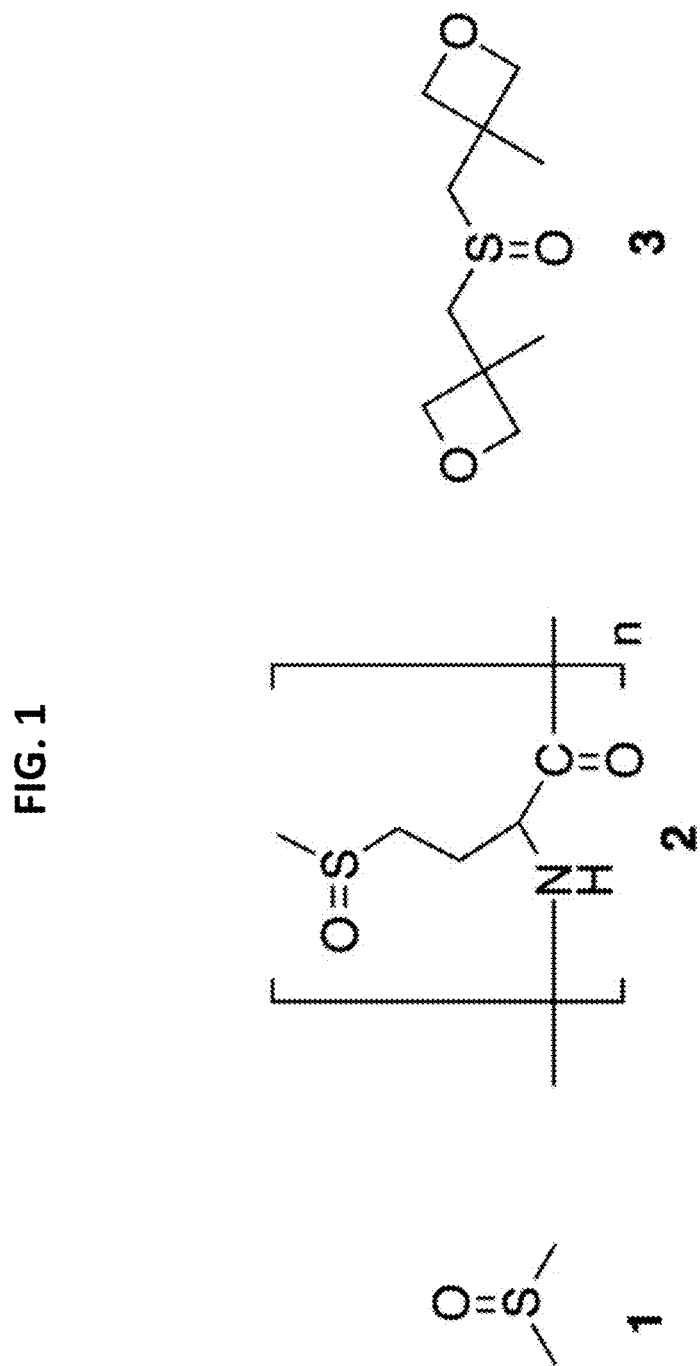
FIG. 1 provides the structures of sulfoxides used for compound storage or aqueous solubility enhancement.

As used herein, the singular terms "a," "an," and "the" include plural referents unless context clearly indicates otherwise. Also, as used herein, the term "comprises" means "includes."

Although methods and materials similar or equivalent to those described herein can be used in the practice or testing of the present disclosure, suitable methods and materials are described below. In addition, the materials, methods, and examples are illustrative only and not intended to be limiting.

To facilitate review of the various examples of this disclosure, the following explanations of specific terms are provided:

The terms "alkyl", "aryl" and other groups refer generally to both unsubstituted and substituted groups unless specified to the contrary.

The term acyl refers to —C(O)$R^f$ wherein $R^f$ is defined below.

"Administration" as used herein is inclusive of administration by another person to the subject or self-administration by the subject.

The term "alkenyl" refers to a straight or branched chain hydrocarbon group with at least one double bond, preferably with 2-15 carbon atoms, and more preferably with 2-10 carbon atoms (for example, —CH=$CHR^g$ or —$CH_2$CH=$CHR^g$, wherein $R^g$ is defined below).

The term "alkoxy" refers to —$OR^d$, wherein $R^d$ is an alkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

Unless otherwise specified, alkyl groups are hydrocarbon groups and, in a number of embodiments, are $C_1$-$C_{16}$ (that is, having 1 to 16 carbon atoms) or $C_1$-$C_{10}$ alkyl groups. Alkyl groups can be branched or unbranched, acyclic or cyclic. The above definition of an alkyl group and other definitions apply also when the group is a substituent on another group (for example, an alkyl group as a substituent of a trialkylsilyl group). For example, a lower alkyl or ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$)alkanoyl can be acetyl, propanoyl or butanoyl; halo($C_1$-$C_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$)alkanoyloxy can be acetoxy, propanoyloxy, butanoyloxy, isobutanoyloxy, pentanoyloxy, or hexanoyloxy.

The term "alkynyl" refers to a straight or branched chain hydrocarbon group with at least one triple bond, preferably with 2-15 carbon atoms, and more preferably with 2-10 carbon atoms (for example, —C≡$CR^h$ or —$CH_2$—C≡$CR^h$, wherein $R^h$ is defined below).

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "aryl" refers to phenyl or naphthyl, or substituted phenyl or naphthyl.

The term "aryloxy" refers to —$OR^e$, wherein $R^e$ is an aryl group.

The term "co-administration" or "co-administering" refers to administration of a an oxetane-substituted compound with at least one other therapeutic agent within the same general time period, and does not require administration at the same exact moment in time (although co-administration is inclusive of administering at the same exact moment in time). Thus, co-administration may be on the same day or on different days, or in the same week or in different weeks. The additional therapeutic agent may be included in the same composition as the oxetane-substituted compound.

The term "heteroaryl" refers to a monocyclic- or polycyclic aromatic ring comprising carbon atoms, hydrogen atoms, and one or more heteroatoms. In a number of embodiments, 1 to 3 heteroatoms are present and are, independently selected from nitrogen, oxygen, phosphorus, sulfur, chlorine, bromine and iodine. As is known to those skilled in the art, heteroaryl rings have less aromatic character than their all-carbon counter parts. A heteroaryl group need thus only have some degree of aromatic character. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidinyl, tetrazolyl, furyl, thienyl, isoxazolyl, thiazolyl, phenyl, isoxazolyl, and oxazolyl. A heteroaryl group can be unsubstituted or substituted with, for example, one or two substituents. In a number of embodiments, heteroaryl groups herein include 2 to 11 carbon atoms ($C_2$-$C_{11}$ heteroaryl groups). In several embodiments, heteroaryl group hereof are monocyclic rings, wherein the ring comprises 2 to 10 carbon atoms or 3 to 6 carbon atoms and 1 to 3 heteroatoms.

The groups set forth above, can be substituted with a wide variety of substituents to synthesize analogs retaining desirable properties. For example, alkyl groups and other groups may be substituted with a group or groups including, but not limited to, a halo group, a benzyl group, a phenyl group, an alkoxy group, a hydroxy group, an amino group (including, for example, free amino groups, alkylamino, dialkylamino groups and arylamino groups), an alkenyl group, an alkynyl group and an acyloxy group. In the case of amino groups (—$NR^aR^b$), $R^a$ and $R^b$ are preferably independently hydrogen, an acyl group, an alkyl group, or an aryl group. Acyl groups may, for example, be substituted with (that is, $R^f$ is) an alkyl group, a haloalkyl group (for example, a perfluoroalkyl group), an alkoxy group, an amino group and a hydroxy group. Alkynyl groups and alkenyl groups may preferably be substituted with (that is, $R^g$ and $R^h$ are, for example) a group or groups including, but not limited to, an alkyl group, an alkoxyalkyl group, an amino alkyl group and a benzyl group.

"Inhibiting" refers to inhibiting the full development of a disease or condition. "Inhibiting" also refers to any quantitative or qualitative reduction in biological activity or binding, relative to a control.

A "therapeutically effective amount" refers to a quantity of a specified agent sufficient to achieve a desired effect in a subject being treated with that agent. For example, a therapeutically amount may be an amount of an oxetane-substituted compound that is sufficient to inhibit radiation-induced damage in a subject. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease such as cancer. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition. In certain embodiments disclosed herein, the treatment inhibits radiation damage in a subject.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Some of the compounds described herein may also exist in their tautomeric form.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. For a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

Overview

Oxetane-substituted compounds, including novel oxetane-substituted sulfoxide, sulfide and sulfone compounds, hereof have demonstrated radiation protection activities. Oxetane-substituted compounds hereof may, for example, effect or provide radioprotection and/or radiomitigation, for example, upon applying or administering an effective dosage thereof. It is anticipated that effective dosages will be in the range of approximately 1 mg/kg to 150 mg/kg. As known to those skilled in the art, however, effective dosage sizes will vary according to the route of administration, and the frequency of administration.

The compounds disclosed herein are useful as radiomitigators to prevent, mitigate, or treat radiation induced damage to cells tissues, or organs, and/or organisms, that have already been exposed to radiation (e.g., from clinical or non-clinical sources), or as radioprotectors to mitigate or prevent damage to cells tissues or organs, and/or organisms that are expected to be exposed to radiation (e.g., in anticipation of radiotherapy, in certain military contexts, and the like).

For example, a water soluble oxetanyl sulfoxide (referred to herein as "MMS350") was evaluated as a radiation protector and mitigator. MMS350 was effective both as a protector and mitigator of clonal mouse bone marrow stromal cell lines in vitro. Single dose administration of MMS350 24 hours after 9.5 Gy total body irradiation of C57BL/6/HNsd mice resulted in significant improvement in survival. Thoracic irradiated mice (20 Gy) demonstrated acute mRNA elevations for: TGF-β, IL-1, TNF-α, MnsOD, NFK—B, Nrf2, SP1, AP1, and TLR4. During the latent period (days 14-100), endothelial cell localized elevation of vWF, VEGF, CCL3, CTGF, and IL6 was detected followed by MnSOD and TGF-β after day 100. MMS350 (100 mM) added daily to drinking water beginning at day 88 after 20 Gy thoracic irradiation substantially decreased pulmonary inflammatory and pro-fibrotic gene expression, migration into the lungs of bone marrow origin luciferase+/GFP+ fibroblast progenitors in (both marrow chimeric and luciferase+ (luc+/GFP) stromal cell line injected mice), and radiation fibrosis (p<0.0001). MMS350 decreased radiation pulmonary fibrosis in both marrow chimeric and luc+ stromal cell line injected mice, and significantly increased survival. In summary, MMS350 when delivered over several weeks (e.g. at least 2 weeks or 2-5 weeks) in drinking water reduces late irradiation induced biomarker elevation and marrow stromal cell mediated pulmonary fibrosis in C57BL/6NTac mice. The non-toxic and orally bioavailable small molecule radiation mitigators disclosed herein should prove an effective counter measure against both acute and chronic effects of ionizing irradiation.

Oxetane-substituted compounds hereof may also have potential as, for example, a DMSO substitute for enhancing the dissolution of organic compounds with poor aqueous solubilities. Such compounds may, for example, provide utility in applications of library storage and biological assays (as, for example, a DMSO substitute).

For example, the use of MMS350 3 (FIG. 1) as a solubilizer and general compound storage additive was evaluated. It was found that addition of sulfoxide 3 increased the aqueous solubility of several model "problem" compounds including naproxen, quinine, curcumin, carbendazim, and griseofulvin. The solubility enhancement surpassed that of DMSO at mass fractions greater than 10%.

Compounds

In a number of embodiments, oxetane substituted compounds hereof have the formula I:

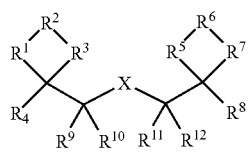

wherein X is S, SO or $SO_2$;

one of $R^1$, $R^2$, and $R^3$ is O and the others of $R^1$, $R^2$ and $R^3$ are independently, the same or different, $CH_2$, or $CR^{13}$ wherein, $R^{13}$ is an alkyl group, an alkenyl group, an alkynyl group, a trialkylsilyl group, or $-(CH_2)_mOR^{15}$, wherein $R^{15}$ is an alkyl group or an aryl group and m is an integer in the range of 1 to 10, one of $R^5$, $R^6$, and $R^7$ is O and the others of $R^5$, $R^6$ and $R^7$ are independently, the same or different, $CH_2$, or $CR^{14}$ wherein, $R^{14}$ is an alkyl group, an alkenyl group, an alkynyl group, a trialkylsilyl group, or $-(CH_2)_nOR^{16}$, wherein $R^{16}$ is an alkyl group or an aryl group and n is an integer in the range of 1 to 10;

$R^4$ and $R^8$ are independently, the same or different, H, an alkyl group, an alkenyl group, an alkynyl group, an aryl group, a heteroaryl group, a $C_1$-$C_3$ alkoxy group, an aryloxy group, or $-(CH_2)_qOR^{17}$, wherein $R^{17}$ is an alkyl group or an aryl group and q is an integer in the range of 1 to 10, provided that $R^4$ is not a $C_1$-$C_3$ alkoxy group or an aryloxy group when $R^1$ or $R^3$ is O and $R^8$ is not a $C_1$-$C_3$ alkoxy group or an aryloxy group when $R^5$ or $R^7$ is O;

$R^9$, $R_{10}$, $R^{11}$ and $R^{12}$ are independently, the same or different, H, an alkyl group, an alkenyl group, an alkynyl group, an aryl group.

In a number of embodiments, $R^{13}$ is a $C_1$-$C_3$ alkyl group, a $C_2$-$C_3$ alkenyl group, a $C_2$-$C_3$ alkynyl group, or a trialkylsilyl group and $R^{14}$ is a $C_1$-$C_3$ alkyl group, a $C_2$-$C_3$ alkenyl group, a $C_2$-$C_3$ alkynyl group, or a trialkylsilyl group.

In a number of embodiments, one of $R^9$ and $R^{10}$ is H and one of $R^{11}$ and $R^{12}$ is H.

In a number of embodiments, one of $R^1$, $R^2$, and $R^3$ is O and the others of $R^1$, $R^2$ and $R^3$ are $CH_2$, and one of $R^5$, $R^6$, and $R^7$ is O and the others of $R^5$, $R^6$ and $R^7$ are $CH_2$.

In certain embodiments, $R^2$ and $R^6$ are each O; and $R^1$, $R^3$, $R^5$, $R^7$ are each $CH_2$.

In certain embodiments, $R^2$ and $R^6$ are each O; $R^1$, $R^3$, $R^5$, $R^7$ are each $CH_2$; $R^4$ and $R^8$ are each $C_1$-$C_{10}$ alkyl such as a methyl, ethyl, propyl, isopropyl, butyl, iso-butyl, sec-butyl, pentyl, 3-pentyl, or hexyl; and $R^9$-$R^{12}$ are each H.

In certain embodiments, $R^9$-$R^{12}$ are each H.

In certain embodiments, X is SO; $R^2$ and $R^6$ are each O; $R^1$, $R^3$, $R^5$, $R^7$ are each $CH_2$; $R^4$ and $R^8$ are each $C_1$-$C_{10}$ alkyl such as a methyl, ethyl, propyl, isopropyl, butyl, iso-butyl, sec-butyl, pentyl, 3-pentyl, or hexyl; and $R^9$-$R^{12}$ are each H.

Figure 24:
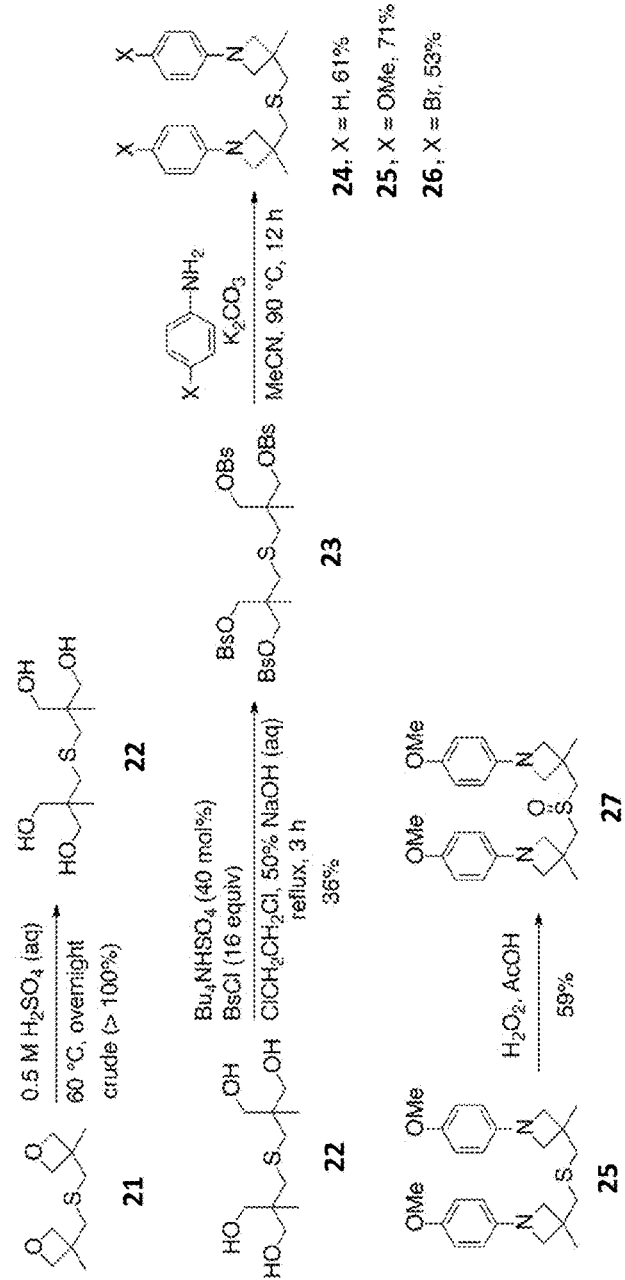
FIG. 24 depicts the synthesis scheme of an azetidine compound.

In other embodiments of formula I, one of $R^1$, $R^2$, and $R^3$ is $NR^{60}$ and the others of $R^1$, $R^2$ and $R^3$ are independently, the same or different, $CH_2$, or $CR^{13}$ wherein, $R^{13}$ is an alkyl group, an alkenyl group, an alkynyl group, a trialkylsilyl group, or $-(CH_2)_mOR^{15}$, wherein $R^{15}$ is an alkyl group or an aryl group and m is an integer in the range of 1 to 10; one of $R^5$, $R^6$, and $R^7$ is $NR^{61}$ and the others of $R^5$, $R^6$ and $R^7$ are independently, the same or different, $CH_2$, or $CR^{14}$ wherein, $R^{14}$ is an alkyl group, an alkenyl group, an alkynyl group, a trialkylsilyl group, or $-(CH_2)_nOR^{16}$, wherein $R^{16}$ is an alkyl group or an aryl group and n is an integer in the range of 1 to 10, wherein $R^{60}$ and $R^{61}$ are each independently H, an alkyl group, an alkenyl group, an alkynyl group, an aryl group or a heteroaryl group; and X, $R^4$, and $R^8$-$R^{12}$ are the same as above. In certain embodiments, $R^{60}$ and $R^{61}$ are each independently an aryl group substituted with an alkoxy group (e.g., a lower alkoxy group) or a halo group, particularly para-substituted. FIG. 24 depicts a synthetic scheme for synthesizing these azetidine-containing compounds.

Also disclosed herein are pharmaceutically acceptable salts or esters of the oxetane-substituted compounds.

In several representative embodiments, the compound has the formula

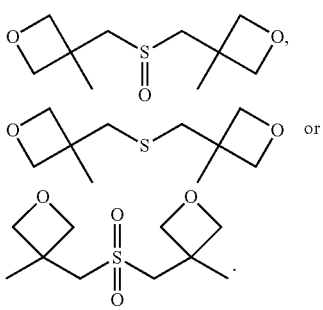

In a number of representative radiation studies, the following compound was studied:

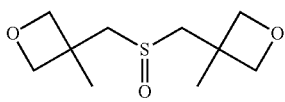

(referred to herein as "MMS350").

As discussed above, the present inventors have also discovered that oxetane-substituted compounds can be used for enhancing the solubility of organic compounds in aqueous media. For model or representative compounds studied, significant solubility enhancements were observed using a representative oxetane-substituted sulfoxide as a cosolvent in aqueous media. In a number of studies, the representative oxetane-substituted sulfoxide had the formula:

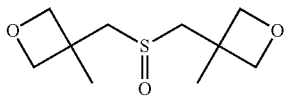

Brine shrimp, breast cancer (MDA-MB-231) and liver cell line (HepG2) toxicity data for the above sulfoxide are set forth below, in addition to comparative IC50 values for a series of PKD1 inhibitors. Radiation damage mitigation studies of the above sulfoxide are set forth below.

In certain embodiments, the oxetane-substituted compounds are solids at room temperature and pressure. In certain embodiments, the oxetane-substituted compounds are water soluble or water miscible and thus may be mixed with water to form an aqueous solution or medium. In further embodiments, the oxetane-substituted compounds may be mixed with an appropriate water-soluble cosolvent to form an aqueous solution. Illustrative cosolvents include N-methyl-2-pyrrolidone (NMP), dimethyl sulfoxide (DMSO), alcoholic solvents (e.g., ethanol or isopropyl alcohol), and acetonitrile.

Also disclosed herein are compounds, and pharmaceutically acceptable salts and esters, thereof, having a formula II:

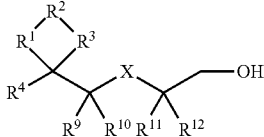

wherein X is S, SO or $SO_2$;

one of $R^1$, $R^2$, and $R^3$ is O and the others of $R^1$, $R^2$ and $R^3$ are independently, the same or different, $CH_2$, or $CR^{13}$ wherein, $R^{13}$ is an alkyl group, an alkenyl group, an alkynyl group, a trialkylsilyl group, or $-(CH_2)_mOR^{15}$, wherein $R^{15}$ is an alkyl group or an aryl group and m is an integer in the range of 1 to 10;

$R^4$ is H, an alkyl group, an alkenyl group, an alkynyl group, an aryl group, a heteroaryl group, a $C_1$-$C_3$ alkoxy group, an aryloxy group, or $-(CH_2)_qOR^{17}$, wherein $R^{17}$ is an alkyl group or an aryl group and q is an integer in the range of 1 to 10;

$R^9$, $R^{10}$, $R^{11}$ and $R^{12}$ are independently, the same or different, H, an alkyl group, an alkenyl group, an alkynyl group, an aryl group.

In certain embodiments of formula II, $R^2$ is O; and $R^1$ and $R^3$ are each $CH_2$.

In certain embodiments of formula II, $R^2$ is O; $R^1$ and $R^3$ are each $CH_2$; $R^4$ is $C_1$-$C_{10}$ alkyl such as a methyl, ethyl, propyl, isopropyl, butyl, iso-butyl, sec-butyl, pentyl, 3-pentyl, or hexyl; and $R^9$-$R^{12}$ are each H.

In certain embodiments of formula II, $R^9$-$R^{12}$ are each H.

In certain embodiments of formula II, X is SO; is O; $R^1$ and $R^3$ are each $CH_2$; $R^4$ is $C_1$-$C_{10}$ alkyl such as a methyl, ethyl, propyl, isopropyl, butyl, iso-butyl, sec-butyl, pentyl, 3-pentyl, or hexyl; and $R^9$-$R^{12}$ are each H.

Also disclosed herein are compounds, and pharmaceutically acceptable salts and esters thereof, having a formula III:

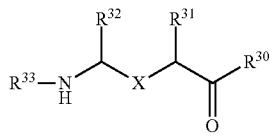

wherein $R^{33}$ includes an oxetanyl sulfane, oxetanyl sulfinyl, or oxetanyl sulfonyl moiety;

X is one of

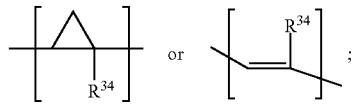

$R^{31}$, $R^{32}$ and $R^{34}$ are, independently, hydrogen, $C_1$-$C_6$ straight or branched-chain alkyl, optionally including a phenyl ($C_6H_5$) group, that optionally is methyl-, hydroxyl- or fluoro-substituted, including: methyl, ethyl, propyl, 2-propyl, butyl, t-butyl, pentyl, hexyl, benzyl, hydroxybenzyl (e.g., 4-hydroxybenzyl), phenyl and hydroxyphenyl. $R^{30}$ is $-NH-R^{35}$, $-O-R^{35}$ or $-CH_2-R^{35}$, where $R^{35}$ is an $-N-O.$, $-N-OH$ or $N=O$ containing group. In one embodiment, $R^{30}$ is

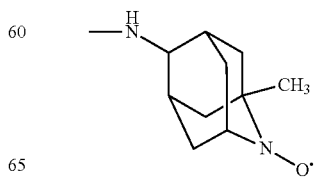

(1-Me-AZADO or 1-methyl azaadamantane N-oxyl). In another embodiment, $R^{30}$ is

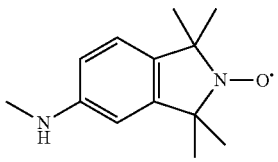

(TMIO; 1,1,3,3-tetramethylisoindolin-2-yloxyl). In a further embodiment, $R^{30}$ is

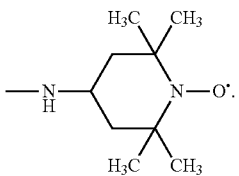

In certain embodiments, $R^{33}$ may be —C(O)—$(CH_2)_x$—S—$CH_2$-oxetanyl-$CH_3$, —C(O)—$(CH_2)_x$—SO—$CH_2$-oxetanyl-$CH_3$, —C(O)—$(CH_2)_x$—$SO_2$—$CH_2$-oxetanyl-$CH_3$, —C(O)O—$(CH_2)_x$—S—$CH_2$-oxetanyl-$CH_3$, —C(O)O—$(CH_2)_x$—SO—$CH_2$-oxetanyl-$CH_3$, or —C(O)O—$(CH_2)_x$—$SO_2$—$CH_2$-oxetanyl-$CH_3$, wherein x is selected from 0 to 5, more particularly 1 to 3, and most particularly 2.

In certain embodiments of formula III, $R^{33}$ is —C(O)O—$(CH_2)_x$—SO—$CH_2$-oxetanyl-$CH_3$; $R^{31}$, $R^{32}$ and $R^{34}$ are each independently hydrogen, $C_1$-$C_6$ straight or branched-chain alkyl, or phenyl-substituted $C_1$-$C_6$ straight or branched-chain alkyl; and $R^{30}$ is

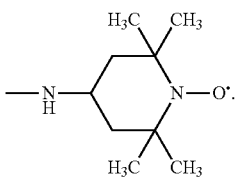

Figure 25:
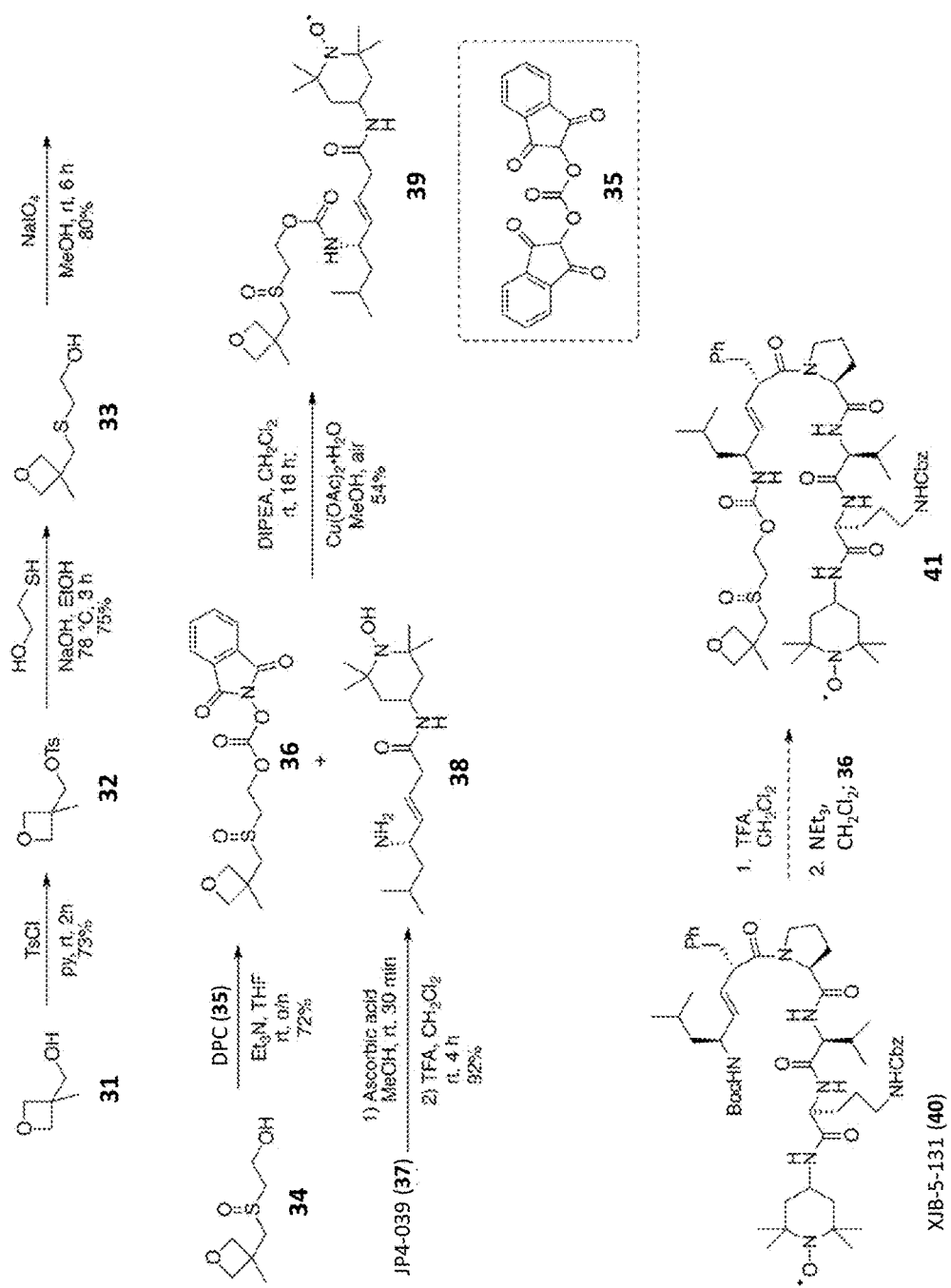
FIG. 25 depicts the synthesis scheme of additional oxetane sulfoxide-substituted compounds.

An example of a compound of formula III is compound 39 in FIG. 25.

Also disclosed herein are compounds, and pharmaceutically acceptable salts and esters thereof, having a formula IV:

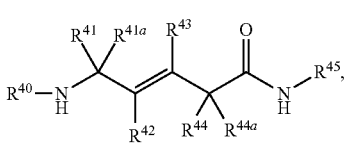

or a formula V

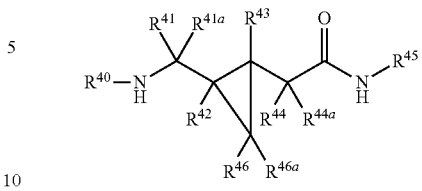

wherein $R^{40}$ includes an oxetanyl sulfane, oxetanyl sulfinyl, or oxetanyl sulfonyl moiety;

$R^{41}$, $R^{41a}$, $R^{44}$, and $R^{44a}$ are each independently hydrogen, a halo, $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted;

$R_4$ is hydrogen, a halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted;

$R^{45}$ is an —N—O., —N—OH or N═O containing group;

$R^{42}$, $R^{43}$, $R^{46}$, and $R^{46a}$ are independently H or a halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted.

In certain embodiments, $R^{40}$ may be —C(O)—$(CH_2)_x$—S—$CH_2$-oxetanyl-$CH_3$, —C(O)—$(CH_2)_x$—SO—$CH_2$-oxetanyl-$CH_3$, —C(O)—$(CH_2)_x$—$SO_2$—$CH_2$-oxetanyl-$CH_3$, —C(O)O—$(CH_2)_x$—S—$CH_2$-oxetanyl-$CH_3$, —C(O)O—$(CH_2)_x$—SO—$CH_2$-oxetanyl-$CH_3$, or —C(O)O—$(CH_2)_x$—$SO_2$—$CH_2$-oxetanyl-$CH_3$, wherein x is selected from 0 to 5, more particularly 1 to 3, and most particularly 2.

Two examples of a compound of formula IV are shown below:

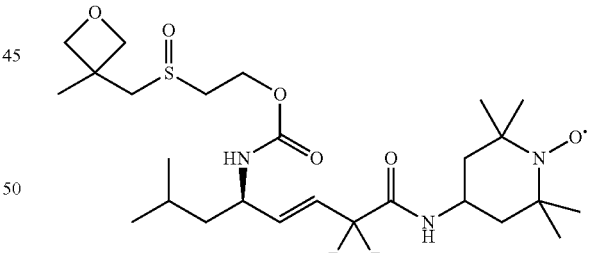

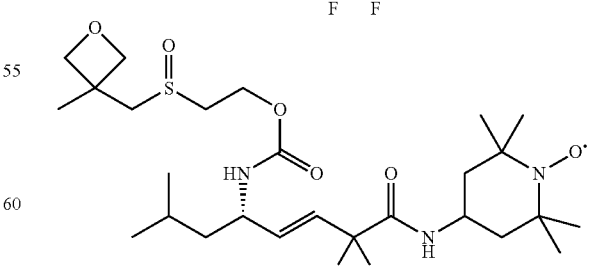

Also disclosed herein are compounds, and pharmaceutically acceptable salts and esters thereof, having a formula VI:

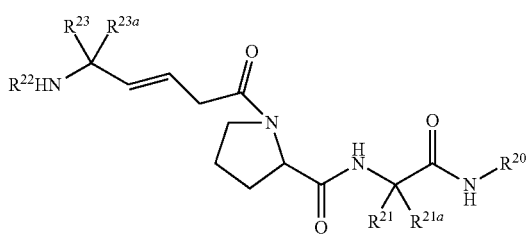

wherein $R^{22}$ includes an oxetanyl sulfane, oxetanyl sulfinyl, or oxetanyl sulfonyl moiety;

$R^{23}$, $R^{23a}$, $R^{21}$, and $R^{21a}$ are each independently hydrogen, a halo, $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted; $R_4$ is hydrogen, a halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted; and $R^{20}$ is an —N—O., —N—OH or N=O containing group.

In certain embodiments, $R^{22}$ may be —C(O)—(CH$_2$)$_x$—S—CH$_2$-oxetanyl-CH$_3$, —C(O)—(CH$_2$)$_x$—SO—CH$_2$-oxetanyl-CH$_3$, —C(O)—(CH$_2$)$_x$—SO$_2$—CH$_2$-oxetanyl-CH$_3$, —C(O)O—(CH$_2$)$_x$—S—CH$_2$-oxetanyl-CH$_3$, —C(O)O—(CH$_2$)$_x$—SO—CH$_2$-oxetanyl-CH$_3$, or —C(O)O—(CH$_2$)$_x$—SO$_2$—CH$_2$-oxetanyl-CH$_3$, wherein x is selected from 0 to 5, more particularly 1 to 3, and most particularly 2.

An example of a compound of formula VI is compound 41 in FIG. 25.

Compositions

Another aspect of the disclosure includes pharmaceutical compositions prepared for administration to a subject and which include a therapeutically effective amount of one or more of the compounds disclosed herein. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. Pharmaceutically acceptable salts include those derived from pharmaceutically acceptable inorganic or organic bases and acids. Particular disclosed compounds possess at least one basic group that can form acid-base salts with acids. Examples of basic groups include, but are not limited to, amino and imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid. In particular, suitable salts include those derived from alkali metals such as potassium and sodium, alkaline earth metals such as calcium and magnesium, among numerous other acids well known in the pharmaceutical art.

Certain compounds include at least one acidic group that can form an acid-base salt with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions also can be used.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl)

amine, 2-hydroxy-tert-butylamine, tris(hydroxymethyl) methylamine, N,N-dimethyl-N-(2-hydroxyethyl)amine, tri-(2-hydroxyethyl)amine and N-methyl-D-glucamine. For additional examples of "pharmacologically acceptable salts," see Berge et al., *J. Pharm. Sci.* 66:1 (1977).

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of poly-carboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

Radiation Protection and Mitigation

As used herein, any compounds used for prevention, mitigation or treatment in a subject of injury caused by radiation exposure is administered in an amount effective to prevent, mitigate or treat such injury, namely in an amount and in a dosage regimen effective to prevent injury or to reduce the duration and/or severity of the injury resulting from radiation exposure. According to one non-limiting embodiment, an effective dose ranges from 0.1 or 1 mg/kg to 100 mg/kg, including any increment or range therebetween, including 1 mg/kg, 5 mg/kg, 10 mg/kg, 20 mg/kg, 25 mg/kg, 50 mg/kg, and 75 mg/kg. However, for each compound described herein, an effective dose or dose range is expected to vary from that of other compounds described herein for any number of reasons, including the molecular weight of the compound, bioavailability, specific activity, etc. The therapeutic window between the minimally-effective dose, and maximum tolerable dose in a subject can be determined empirically by a person of skill in the art, with end points being determinable by in vitro and in vivo assays, such as those described herein and/or are acceptable in the pharmaceutical and medical arts for obtaining such information regarding radioprotective agents. Different concentrations of the compounds described herein are expected to achieve similar results, with the drug product administered, for example and without limitation, once prior to an expected radiation dose, such as prior to radiation therapy or diagnostic exposure to ionizing radiation, during exposure to radiation, or after exposure in any effective dosage regimen. The compounds can be administered one or more times daily, once every two, three, four, five or more days, weekly, monthly, etc., including increments therebetween. A person of ordinary skill in the pharmaceutical and medical arts will appreciate that it will be a matter of simple design choice and optimization to identify a suitable dosage regimen for prevention, mitigation or treatment of injury due to exposure to radiation.

The compounds described herein also are useful in preventing, mitigating (to make less severe) and/or treating injury caused by radiation exposure. In one embodiment, the radiation is ionizing radiation. Ionizing radiation consists of highly-energetic particles or waves that can detach (ionize) at least one electron from an atom or molecule. Examples of ionizing radiation are energetic beta particles, neutrons, and alpha particles. The ability of light waves (photons) to ionize an atom or molecule varies across the electromagnetic spectrum. X-rays and gamma rays can ionize almost any molecule or atom; far ultraviolet light can ionize many atoms and molecules; near ultraviolet and visible light are ionizing to very few molecules. Microwaves and radio waves typically are considered to be non-ionizing radiation, though damage caused by, e.g., microwaves, may result in the production of free-radicals as part of the injury and/or physiological response to the injury.

Radiotherapy Protection

Radiotherapy and Cancer

Radiation therapy works by directing ionizing radiation into the area being treated with the goal of damaging the genetic material of cancerous cells thereby making it impossible for these cells to divide. Accordingly, radiotherapy is an important tool in the fight against cancer and is used in the treatment of as many as 50% of all cancer patients. In fact, more than half a million cancer patients receive radiation therapy each year, either alone or in conjunction with surgery, chemotherapy or other forms of cancer therapy. Other terms for radiotherapy include radiation therapy, x-ray therapy, electron beam therapy, cobalt therapy, or irradiation.

Radiotherapy is especially useful in cases where surgical removal of the cancer is not possible, where surgery might debilitate the patient, or where surgical debulking of the tumor has not absolutely removed all cancerous tissue. Radiotherapy is routinely used following surgery to destroy any cancer cells that were not removed by surgery. Further uses of radiotherapy are prior to surgery where it can "shrink" a previously inoperable tumor down to a manageable size to enable surgical excision.

Radiation therapy can also be used to help relieve symptoms of advanced cancer (such as bleeding or pain), even if a cure is not possible. Over one-third of the practice of radiation therapy is palliative. The typical intent of palliative treatment is to relieve pain quickly and maintain symptom control for the duration of the patient's life. Accordingly, treatment is usually tailored to the patient's clinical condition and overall prognosis. Palliative treatment is often complementary to analgesic drug therapies and may enhance their effectiveness because it can directly target the cause of pain.

Specifically, radiotherapy can be used to treat localized solid tumors, such as cancers of the skin, head and neck, brain, breast, prostate, cervix, and the like. Radiation therapy can also be used to treat cancers of the blood-forming cells and lymphatic system including leukemia and lymphoma respectively, and the like. Mucous membranes or hair in the vicinity of the radiation or in the path of the radiation (e.g., scalp hair in the case of a brain tumor and rectal mucosa in the case of prostate cancer) can be protected using the presently disclosed compounds.

Radiation Forms and Dosage

External beam radiation therapy commonly uses photons, which are sometimes called "packets of energy," to treat cancer. It is an object herein to ameliorate the negative effects of all radiotherapy regardless of the form of the photon or particle, including x-rays, gamma rays, UV rays including UV-A, UV-B and UV-C, neutrons, protons, and electrons including beta particles and the like.

X-rays are a very common form of radiation used in radiotherapy. Gamma rays are another form of photons used in radiotherapy. Gamma rays can be produced spontaneously as certain elements (such as radium, uranium, and cobalt 60), which release radiation as they decompose, or decay. Each element decays at a specific rate and can give off energy in the form of gamma rays and other particles. Typically x-rays and gamma rays have the same general effect on cancer cells.

External beam radiation therapy can be delivered by means of a linear accelerator. Typically, linear accelerators use powerful generators to create the high energy rays for external beam radiation therapy. Generally, linear accelerators are capable of producing x-rays at various energies. The linear accelerator can include a special set of lead shutters, called collimators, which focus and direct the rays to the tumor. The linear accelerator can be a large "L-shaped" design which allows it to rotate and deliver radiation from all angles. Multiple angles allow the maximum amount of radiation to be delivered to the tumor while delivering a minimal amount of radiation to the surrounding healthy tissue. The compounds and methods described herein can be used in conjunction with collimators or other devices and methods that limit radiation exposure to normal cells.

Compounds and methods described herein may be capable of ameliorating the effects of most forms of radiotherapy. For example, the compounds and methods can ameliorate the effects of local-field radiation and wide-field radiation. Local field radiation relates to a narrow beam of radiation directed at the specific metastatic site or sites. Customarily, local field radiation has tended to be used for patients with a long life expectancy and fewer metastatic sites. In contrast, wide-field radiation employs a larger field of radiation and is often used to treat patients with a shorter life expectancy and multiple metastatic pain-causing sites.

Radiotherapy dosage is measured by the scientific unit rad (radiation absorbed dose) which is a radiation energy dose equal to an energy of 100 ergs per gram of irradiated material. A patient who receives radiation therapy as a treatment for cancer can receive several thousand rads over a very short period of time (weeks or months). In contrast, a typical scanning x-ray contains far fewer rads. For example, modern mammography systems used to take x-ray images of the breast use approximately 0.1 to 0.2 rad dose per x-ray.

According to traditional radiotherapy, the larger the daily dose of radiation, the lower the total dose that can be administered because of limits to normal tissue tolerance. Proportionately more tumor cells are killed when the daily radiation dose is larger. Typically a balance is obtained between the killing of tumor cells and the adverse radiation effects on normal tissues, which are largely a function of the daily dose. A number of different schedules have been developed that take into account specific tumor characteristics and the tolerance of normal tissues. The literature is divided regarding the optimal radiation schedule to achieve tumor regression and disease palliation of either primary or metastatic sites. Generally, however, radiation treatment is planned in relation to clinical status. Because a main objective herein is to ameliorate the negative effects of radiation therapy, normal tissue can have a higher tolerance to radiation therapy and larger dosages of radiation can be administered safely.

Side Effects of Radiation

In general, radiation therapy is a local treatment. It typically affects the cells in the treated area. However, as mentioned above, in addition to damaging cancer cells, radiation can also damage normal cells located in the treated area. Normal cells that are located in the treated area can include skin cells, mucous membranes, hair follicles, and the like.

Radiation side effects are typically restricted to the radiation portal and can be classified as either acute, occurring during or immediately after the course of radiation therapy, or late, occurring months to years later. Acute radiation effects are more prominent with radiation schedules that deliver high total doses of radiation with small daily fractions; they generally begin at the end of the second week of therapy. Acute radiation effects, occurring primarily at skin and mucosal surfaces, usually consist of an inflammatory response such as skin erythema or pigmentation, or as mucositis. Late radiation effects may arise without any preceding acute reactions. Fibrosis is the most common type of late radiation injury and can be observed in many types of tissue, including skin.

Other skin conditions caused by radiation therapy include dry and moist desquamation. Dry desquamation, which is characterized by dry and flaky skin and pruritus in the area of irradiation. Moist desquamation, is characterized by sloughing of the epidermis, exposing the moist, raw, dermis layer of the skin.

By the phrase protecting from radiation damage it is implied that relative to damage expected to be incurred to cells, tissue, or organism within a subject or within biological material following exposure to a given amount of radiation (for example ionizing, infra-red or ultra-violet radiation) damage is prevented, minimized or reduced due to effect of the radioprotector compound.

Clinical radiation sources include beam sources (e.g., X-ray, gamma rays, proton beams, etc.) and material sources (e.g., as radium, uranium, cesium 131, cobalt 60, samarium 145, iodine 125 and 127, etc.) that for example may be applied on and/or around a tumor site, or systemically, parenterally, or orally administered.

In certain embodiments the compounds disclosed herein are administered preferentially to cells, tissues or organs likely to be exposed to radiation but that are intended to be protected from such radiation exposure. For example, in the case of administration in conjunction with cancer radiotherapy the formulation will preferably be administered preferentially to normal (non-tumor) tissues or cells surrounding a tumor or lesion that are likely to be exposed to radiation in the course of radiotherapy.

In certain embodiments the tumor or neoplasm to be treated is of a cancer selected from the group consisting of lung cancer, colorectal cancer, NSCLC, bronchoalveolar cell lung cancer, bone cancer, pancreatic cancer, skin cancer, cancer of the head or neck, cutaneous melanoma, intraocular melanoma, uterine cancer, ovarian cancer, rectal cancer, anal region cancer, stomach cancer, gastric cancer, colon cancer, breast cancer, uterine cancer, fallopian tube carcinoma, endometrial carcinoma, cervical carcinoma, vaginal carcinoma, vulval carcinoma, Hodgkin's Disease, esophagus cancer, small intestine cancer, endocrine system cancer, thyroid gland cancer, parathyroid gland cancer, adrenal gland cancer, soft tissue sarcoma, urethral cancer, penis cancer, prostate cancer, bladder cancer, kidney cancer, ureter cancer, renal cell carcinoma, renal pelvis carcinoma, mesothelioma, hepatocellular cancer, biliary cancer, chronic leukemia, acute leukemia, lymphocytic lymphoma, CNS neoplasm, spinal axis cancer, brain stem glioma, glioblastoma multiform, astrocytoma, schwannoma, ependymoma, medulloblastoma, meningioma, squamous cell carcinoma and pituitary adenoma tumors, and tumor metastasis. In certain embodiments the tumor or tumor metastasis is refractory.

In certain embodiments the radiation is produced by an implanted radiation source and/or by a beam radiation source. In certain embodiments the compound disclosed herein is co-administered with an anti-cancer drug. For example, the radioprotective compounds described herein can also be used advantageously in therapy in combination with other medicaments, such as chemotherapeutic agents, for example, radiomimetic agents that are cytotoxic agents that cells, tissues, and/or organs in a manner similar to ionizing radiation. Examples of radiomimetic agents include, but are not limited to bleomycin, doxorubicin, adriamycin, 5FU, neocarcinostatin, alkylating agents and other agents that produce DNA adducts.

The compound may be administered prior to radiation exposure. In certain embodiments, the compound may be administered after irradiation, but before the appearance of symptoms. In certain embodiments, and compounds may be administered after the appearance of symptoms, which may mitigate symptoms or may treat established complications.

In particular, certain embodiments of the oxetane-substituted compounds (e.g., MMS350) are radiation protector/mitigators that are water soluble, and easily administered (e.g., orally administered to a subject). The expense of producing MMS350 is far lower than MnSOD-Plasmid Liposomes, which have been shown to prevent/delay radiation fibrosis in the same mouse model. Furthermore, MnSOD-PL is relatively ineffective when delivered weeks-months after irradiation, at the time that fibrosis is forming, and appears to be only effective when delivered prior to irradiation. In contrast, MMS350 as shown in the data reported herein, has high effectiveness when delivered months after irradiation and at the time of initiation of radiation fibrosis in the lung. Thus, MMS350 is a novel agent, inexpensive to produce, safe (a toxic dose has not yet been reached in dose escalation experiments to date in mice), and it has a unique ease of administration.

In initial experiments, tissue culture using hematopoietic progenitor cell line, IL-3 dependent, 32D cl 3 cells, which forms colonies in semisolid medium showed that MMS350 demonstrated significant effectiveness as both a radiation protector (delivered before irradiation) and radiation damage mitigator (when drug is delivered after irradiation).

MMS350 was delivered by intraperitoneal injection to C57BL/6 mice (n=15/group) before or after the 9.5 Gy of total body irradiation (a dose which kills at least 50% of mice at 30 days) and indicative of death from the hematopoietic syndrome (bone marrow failure). In this experiment, MMS350 was both a protector when delivered prior to irradiation and mitigator when delivered after irradiation comparable to JP4-039. These experiments demonstrate that MMS350 is both a potent radiation protector and mitigator against total body irradiation and may be of value as a radiation countermeasure against the hematopoietic syndrome.

Additional Therapeutic Indications of Oxetane-Substituted Compounds (Prevention of Fibrosis)

One of the most pressing problems in clinical radiotherapy is defining a way to treat the late side effects of irradiation. Acute radiation toxicity, as an example of the hematopoietic syndrome as described above, is treated with agents to alleviate the inflammatory reaction to cell death caused by radiation. After the acute effects of irradiation, there is a latent period during which there is no clinical or histopathologic signs of irradiation damage. After the latent period, depending on irradiation dose, fraction size, and time over which irradiation is delivered, as well as volume of tissue treated, the late side effects of irradiation are initiated. The most prominent late effect is fibrosis. A valuable model for measuring effects of new radiation protective or therapeutic agents against the late effects of irradiation is the lung fibrosis model in C57BL/6 mice. Mice irradiated to the thoracic cavity (head and neck shielded, abdomen and lower body shielded) demonstrate profound radiation fibrosis (organizing alveolitis) at around 120-150 days after thoracic irradiation. In single fraction experiments delivering 20 Gy to the upper body (thoracic cavity) and in fractionated irradiation experiments, this model of fibrosis has been shown to be a valuable test in which to measure the effectiveness of agents that can protect, mitigate, or treat as a therapeutic (eliminate the fibrosis after it has already formed and there are signs and symptoms of lung compromise, as a definition of "treatment" in this particular embodiment), and this system has been used to measure effectiveness of multiple other therapeutic candidate agents.

In a mouse model for radiation fibrosis, a significant component of the fibrotic lesion has been shown to come from bone marrow stromal cells, which migrate through the circulation into the lungs. This model has been published previously and shown to be effective for quantitation of the contribution of fibrosis from both resident in situ of fibroblast progenitors and cells coming from the bone marrow microenvironment, as bone marrow stromal cells. In previous experiments, contribution of the fibrotic lesion in the lung from bone marrow derived cells has been shown to be significant and range from 20-50%.

MMS350 was tested in two mouse models of fibrosis in the C57BL/6J model. In the first system (chimeric mice) C57BL/6 mice were irradiated to a total body dose of 10 Gy, which is known to be lethal for 100% of animals in the absence of bone marrow transplantation. These mice were then transplanted intravenously with luciferase positive C57BL/6J mouse bone marrow. These mice are valuable for measuring the site of hematopoiesis from donor origin marrow since the animals can be imaged for mobilization in a specific imaging system, which detects the luciferase signal. In this assay system, animals are injected with luciferin (the substrate for the enzyme luciferase) bone marrow cells, which contain luciferase (those from the donor marrow strain) metabolize luciferin and produce a fluorescence which is detected in a camera system over the immobilized mice. These same animals can be imaged serially over several weeks-months and followed for migration of luciferase positive cells from bone marrow sites into irradiated sites.

Chimeric mice with luciferase positive bone marrow demonstrated marrow resistance in bone marrow sites including pelvis, long bones, skull, and tail, but no significant migration of cells into the lungs. This irradiation total body dose, which was given to produce chimerism, was well below the threshold for causing radiation lung fibrosis in this mouse strain, according to previous publications. There was no significant migration of cells into the lungs. A subgroup of these animals that received an additional boost of irradiation to the thoracic cavity demonstrated significant migration into the chest/lungs of luciferase positive cells. MMS350 placed in the drinking water significantly reduces migration of bone marrow cells into the lungs after a second thoracic irradiation dose. This result provides strong evidence that MMS350 is preventing radiation fibrosis.

In a second experiment, a clonal bone marrow stromal cell line established from long-term bone marrow cultures of luciferase positive mice and shown to be fluorescent in vitro when luciferin is added to the cells in culture was injected. Cells were injected intraperitoneally in mice that received no thoracic irradiation and in serial photographs over time, the cells stayed in the abdomen. When mice were irradiated to the thoracic cavity (head and neck and abdomen shielded) to 20 Gy and luciferin positive bone marrow stromal cells were injected into the peritoneal cavity, the luc+ cells migrated into the lungs. The positive areas were known to be in the lung, because in representative mice, sacrificed and then the heart removed, animals placed back in the imaging system showed identical positivity in the lungs, demonstrating that the fluorescence from luciferin that was activated by luciferase, were in fact in the lungs. Administration of MMS350 in the drinking water to mice in a subgroup of this experiment demonstrated a significant decrease in migration into the lungs of luc+ cells causing fibrosis. Thus, there is a novel and unique indication for the use of MMS350, and similar oxetane-substituted compounds as an agent which can prevent radiation fibrosis in irradiated lung, which is susceptible to this late side effect of irradiation.

Increasing Aqueous Solubility

The oxetane-substituted compounds disclosed herein may also be useful for enhancing the dissolution of organic compounds with poor aqueous solubilities. For example, the oxetane-substituted compounds may be mixed with (i) a cosolvent such as, for example, N-methyl-2-pyrrolidone (NMP), dimethyl sulfoxide (DMSO), alcoholic solvents (e.g., ethanol or isopropyl alcohol), and acetonitrile and (ii) a water-insoluble compound in an aqueous medium. The resulting composition may also include additives such as pH buffers (e.g., borax or a phosphate) that are typically used in storage compositions.

Bone Healing

In some embodiments, the disclosed compounds are useful for accelerating bone healing, bone growth, bone reconstruction, or bone repair in a subject. The accelerated bone healing may be in response to an acute traumatic injury, such as a partial or complete fracture or breakage of the bone. In some embodiments, the disclosed compounds may be administered in anticipation of a bone fracture, such as before a surgical procedure where a bone breakage is possible or expected. Alternatively, or additionally, the subject may suffer from, or be at increased risk of developing, a bone degenerative disease, such as osteoporosis. An "increased risk" of bone degenerative disease is a risk that is elevated by known risk factors the subject possesses. For example, a woman who has undergone bone density imaging and is found to have sub-optimal or sub-normal levels of bone density would be at increased risk of osteoporosis. In other examples, genetic or demographic information may be used to identify someone of known risk. Other clinical settings in which bone healing or reconstruction can be delayed or impaired include, but are not limited to diabetes, hormone deficiencies, infection, poor vascularity, poor nutritional status, and certain pharmacological agents such as corticosteroids, chemotherapeutics, antibiotics, and anticoagulants.

In some embodiments, a method of accelerating bone healing, bone growth, bone reconstruction, or bone repair comprises administering one or more of the compounds disclosed herein, or a pharmaceutical composition comprising one or more of the compounds, to a subject in need thereof. The method may further comprise selecting a subject in need of such treatment. The selection process may include identifying a subject suffering from a bone fracture, or at risk of suffering a bone fracture, identifying a subject suffering from a bone degenerative disease, or at risk from developing a bone degenerative disease, and/or identifying a subject in which bone healing, bone growth, bone regeneration and/or bone repair may be delayed or impaired. Subjects suffering from, or at risk of developing, a bone degenerative disease may be identified by any suitable technique known to a person of ordinary skill in the art, such as a bone density test, and/or by reviewing factors such as medical history including family history, for example, to identify subjects that may have a low bone density, and physical factors including size, race and age. Subjects suffering from a bone fracture, including partial and complete fractures, may be identified by any suitable technique, including, but not limited to, physical examination, X-ray, CT, MRI or a combination thereof. Subjects in which bone healing, bone growth, bone regeneration and/or bone repair may be delayed or impaired may be identified by any suitable technique, including, but not limited to, medical examination and medical history.

The disclosed compounds may also be useful in children and adolescents who are suffering from damage to the bone growth plate. In such subjects, administration of one or more of the disclosed compounds may accelerate healing of the bone growth plate, including accelerated bone growth.

In some embodiments, a compound disclosed herein is administered in an amount and regimen effective for accelerating bone healing in a subject in need thereof. The amount and regimen may also be selected to reduce the duration and/or severity of bone injury or deficiency caused by an injury, pathology or degenerative condition. According to one non-limiting embodiment, an effective dose ranges from 0.1 or 1 mg/Kg to 100 mg/Kg, including any increment or range therebetween, including 1 mg/Kg, 5 mg/Kg, 10 mg/Kg, 20 mg/Kg, 25 mg/Kg, 50 mg/Kg, and 75 mg/Kg. However, for each compound described herein, an effective dose or dose range may vary from that of other compounds described herein for any number of reasons, including the molecular weight of the compound, bioavailability, specific activity, etc. The therapeutic window between the minimally-effective dose, and maximum tolerable dose in a subject can be determined empirically by a person of skill in the art, with end points being determinable by in vitro and in vivo assays, such as those described herein and/or are acceptable in the pharmaceutical and medical arts for obtaining such information regarding bone healing. Different concentrations of the agents described herein are expected to achieve similar results, with the drug product administered, for example and without limitation, once prior to an expected bone injury, such as prior to surgery, during bone injury (such as during a surgical procedure), or after bone injury in any effective dosage regimen. For osteoporosis or similar conditions, the composition may be administered prophylactically, such as in a susceptible population, for example in postmenopausal women. The compounds can be administered by any suitable technique, such as orally, topically or intravenously. The compounds may be administered one or more times daily, once every two, three, four, five or more days, weekly, monthly, etc., including increments therebetween. A person of ordinary skill in the pharmaceutical and medical arts will be able to identify a suitable dosage regimen for bone healing, and/or prevention or mitigation of bone injury.

In some embodiments, the subject is non-irradiated or minimally-irradiated, meaning that the subject has either not been exposed to radiation or has not been exposed to 1-10 Gy or more of radiation within 14, 7, 6, 5, 4, 3, 2, or 1 days of administration of the compound. The subject may have been minimally irradiated, and thus has received diagnostic amounts of radiation, typically including insignificant amounts of radiation less than 1 Gy, less than 5 Gy or less than 10 Gy, and typically in the milliGy or milliSv range, such as in exposure to X-rays for diagnostic purposes or during air travel, as opposed to chemotherapeutic doses which typically are much higher.

Irradiation to bone as well as other skeletal disorders associated with reduced bone growth can be associated with impaired fracture healing, skeletal reconstruction, engraftment of bone and bone-substitute materials, and skeletal growth and remodeling. The toxic effects of ionizing radiation on bone are of continued interest in radiation oncology. Pediatric oncology patients are at particular risk of long-term side-effects from irradiation of immature bone, including abnormal skeletal maturation, growth retardation, and fracture (Bluemke D A, Fishman E K, Scott W W: Skeletal complications of radiation therapy. Radiographics 14: 111-121, 1994; Brown R K, Pelker R R, Friedlaender G E, Peschel R E, Panjabi M M: Postfracture irradiation effects on biomechanical histologic parameters of fracture healing. J Ortho Res 9: 876-882, 1991; Dawson W B: Growth impairment following radiotherapy in childhood. Clin Radiol 19: 241-256, 1968; Mitchell M J, Logan M L: Radiation-induced changes in bone. Radiographics 18: 1125-1136, 1998; Roebuck D J: Skeletal complications in pediatric oncology patients. Radiographics 4: 873-885, 1999). Post-irradiation bone injury in adults is manifested primarily by osteoradionecrosis and fracture (Lerouxel E, Moreau A, Bouler J M, Giumelli B, Daculsi G, Weiss P, Malard O: Effects of high doses of ionizing radiation on the bone: A new model for evaluation of bone engineering. Br J Oral Maxillofac Surg 47: 602-607, 2009). Radiation has clearly been shown to inhibit spine fusion in animal models (Emery S E, Brazinski M S, Koka A, Bensusan J S, Stevenson S. The biological and biomechanical effects of irradiation on anterior spinal bone grafts in a canine model. J Bone Joint Surg. 1994; 76A:540-8; Bouchard J A, Koka A, Bensusan J S, Stevenson S, Emery S E. Effects of irradiation on posterior spinal fusions. A rabbit model. Spine 1994; 19:1836-41). There is unmistakable clinical significance of post-irradiation bone grafting. In orthopedic oncology, radiation is a powerful adjunct to surgical treatments. A recent review of outcomes of treatment for metastatic spinal cord compression determined that 40% to 67% of patients undergoing pre-surgical radiation developed complications, in contrast to 33% of those who received surgery as the initial intervention (Kim J M, Losina E, Bono C M, Schoenfeld A J, Collins J E, Katz J N, Harris M B. Clinical outcome of metastatic spinal cord compression treated with surgical excision±radiation versus radiation therapy alone: A systematic review of literature. Spine 2012; 37:78-84). The orthopedic oncologist often sees pathologic fractures or impending fractures in irradiated bones. The most common complication seen is that of impaired wound healing and infection (Dormand E L, Banwell P E, Goodacre T E. Radiotherapy and wound healing. Int Wound J. 2005; 2:112-27). Management of osseous tumors and extensive osteoradionecrosis, as a side-effect of radiotherapy, often require the removal of large amounts of bone; skeletal reconstruction in a previously irradiated field may be delayed because of poor post-irradiation bone healing (Hu W W, Ward B B, Wang Z, Krebsbach P H. Bone regeneration in defects compromised by radiotherapy. J Dent Res. 2010; 89:77-81).

In some embodiments, the subject has been irradiated, is currently being irradiated, and/or will be irradiated, with 1 Gy to 100 Gy or more of radiation, such as from 1 to 80 Gy, from 1 to 60 Gy, from 1 to 40 Gy or 1 to 20 Gy, within 14, 7, 6, 5, 4, 3, 2, or 1 days of administration of the compound. The irradiation may be chemotherapeutic radiation, or a result of an incident involving radiation, such as a release of radioisotopes or a dirty bomb, a nuclear explosion, an incident at a nuclear facility, such as a nuclear power plant, or a military incident. In certain embodiments, the subject received the acute traumatic injury prior to, or substantially simultaneously to, exposure to the radiation. Alternatively, or additionally, the subject may have been suffering from, or at risk of developing, a bone degenerative disease prior to exposure to the radiation. In other embodiments, the bone damage, including fractures and degeneration, may be due to or exacerbated by exposure to radiation. For example, in children who are receiving irradiation of cancers such as sarcomas or in adults who may have bone cancers or metastases where radiation is required, irradiation may lead to bone fractures or, particularly in children, damage to the growth plate. In such embodiments, the disclosed compounds may reduce the secondary damage caused by irradiation and increase the speed of bone healing, compared to a subject similarly exposed to radiation and not administered a disclosed compound.

Examples—Compound Synthesis

A representative synthetic scheme for bifunctional sulfides and sulfones, as well as specific representative examples thereof, are set forth below.

Scheme 1.

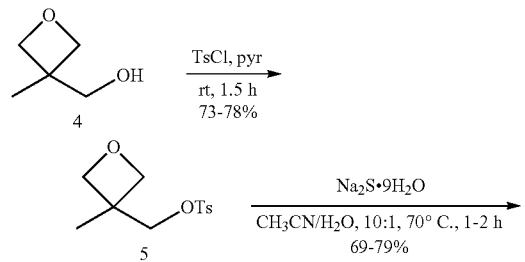

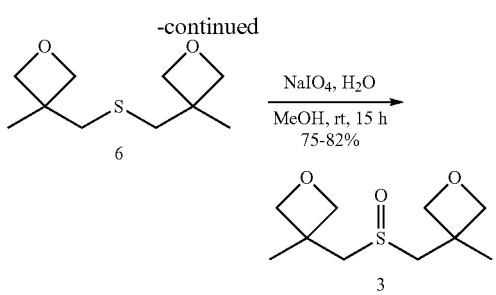

Materials and Methods.

General.

Moisture-sensitive reactions were performed under an atmosphere of nitrogen. 3-Tosyloxymethyl-3-methyl-oxetane was prepared according to a literature protocol. Curcumin (Acros, 95%), naproxen (Acros, 99%), quinine (Acros, 99%), DMSO (Aldrich, 99.9+%), and HPLC-grade water (Aldrich, CHROMASOLV®) were purchased from commercial suppliers and used as received. Carbendazim (Aldrich, 97%) was recrystallized from absolute EtOH, and griseofulvin (Acros, 97%) was recrystallized from toluene. N-Methyl-2-pyrrolidone (Acros, 99%) was distilled from $CaH_2$ under vacuum and stored over 4 Å MS. All other reagents were used as received unless otherwise stated. Analytical thin-layer chromatography (TLC) was performed on pre-coated silica gel 60 F-254 plates (particle size 0.040-0.050 mm, 230-400 mesh) and visualization was accomplished by staining with $KMnO_4$ or p-anisaldehyde solutions. $^1H$ NMR spectra ($CDCl_3$) and $^{13}C$ NMR spectra ($CDCl_3$) were referenced to residual chloroform (7.27 ppm, $^1H$, 77.00 ppm, $^{13}C$). Chemical shifts (δ) are reported in ppm using the following convention: chemical shift, multiplicity (s=singlet, d=doublet, t=triplet, q=quartet, m=multiplet, b=broad), coupling constants, and integration. IR spectra were collected as attenuated-total-reflection infrared (ATR-IR) spectra. Mass spectra were obtained on a Micromass Autospec double focusing instrument. UV/VIS spectra were recorded on a Perkin Elmer Lambda EZ210 spectrophotometer. pH Determinations were made using a 3 mm Ross™ glass combination micro pH electrode (model 8220BNWP) after calibration in standard buffer solutions (pH 4.0, 7.0, and 10.0) at room temperature.

Bis((3-methyloxetan-3-yl)methyl)sulfane (6)

A 3-necked 3-L round-bottom flask equipped with an overhead stirrer, internal thermometer, and a third arm bearing an argon balloon was charged with 3-tosyloxymethyl-3-methyl-oxetane 4 (45.4 g, 177 mmol) and backfilled with $N_2$ (3×). To the flask was added acetonitrile (900 mL) via cannula. The reaction apparatus was placed in a large heating mantle. The argon balloon was replaced with a 250-mL addition funnel containing a solution of $Na_2S \cdot 9H_2O$ (94.5 g 386 mmol) in degassed $H_2O$ (100 mL). The solution was added drop-wise over 25 minutes. Once the addition was complete, the reaction mixture was heated to 70° C. over 45 minutes and maintained at 70° C. for 1 hour. The mixture was cooled to 20° C. (internal temp), the resulting white precipitate was filtered by gravity, and to the filtrate was added EtOAc (1 L). The resulting precipitate was removed by aspirator filtration, and the filtrate was divided into two 1-L batches. To each batch was added water (500 mL), the layers were separated, and the aqueous portion was extracted with EtOAc (2×200 mL). The combined organic layers were washed with brine (100 mL), and the EtOAc layers from the batches were combined and dried ($Na_2SO_4$) overnight, filtered, and concentrated. Kugelrohr distillation was performed on the concentrate. One fraction (T<100° C., 15 Torr) was discarded, and subsequent product collection (140° C.<T<160° C.) yielded a yellow distillate. The distillate was taken up in EtOAc (200 mL), washed with water (100 mL) and brine (100 mL), dried (Na2SO4), and concentrated. Kugelrohr distillation (140° C., 15 Torr) afforded 6 (14.2 g, 79%) as a yellow-green oil: IR (ATR) 2956, 2924, 2861, 1450, 1236, 973, 829 $cm^{-1}$; $^1H$ NMR (300 MHz, $CDCl_3$) δ 4.47 (d, J=5.7 Hz, 4H), 4.38 (d, J=6.0 Hz, 4H), 2.93 (s, 4H), 1.38 (s, 4H); $^{13}C$ NMR (75 MHz, $CDCl_3$) δ 81.9, 43.7, 40.3, 23.0; HRMS (ES) m/z calc for $C_{10}H_{18}O_2NaS$ (M+Na) 225.0925, found 225.0908.

3,3'-Sulfinylbis(methylene)bis(3-methyloxetane) (3)

A 1-L round-bottom flask was charged with a solution of 6 (14.9 g, 73.6 mmol) in MeOH (240 mL) and cooled to 0° C. A solution of $NaIO_4$ (16.5 g, 77.3 mmol) in water (180 mL) was added via addition funnel over about 15 minutes. The ice bath was removed and the slurry was warmed to room temperature. MeOH (2×50 mL, added 20 minutes apart) was added, and the mixture was stirred for 12 hours at room temperature. The mixture was filtered through a fritted funnel, and the white precipitate was washed with MeOH. The combined filtrate and washings were concentrated in vacuo, and the concentrate was co-evaporated with toluene (200 mL). $CH_2Cl_2$ (400 mL) was added to the residue, followed by $MgSO_4$. The mixture was filtered, and the filtrate was concentrated in vacuo to afford crude 3 (15.82 g) as a yellow solid. To the flask containing the crude solid was added toluene (200 mL), and the slurry was heated to 60° C. to affect complete dissolution. Decolorizing carbon was added, and the mixture was filtered by gravity into a 1-L Erlenmeyer flask. To the colorless solution was slowly added distilled hexanes (about 100 mL total) until cloudiness/precipitation occurred. The mixture was allowed to stand at room temperature overnight. Upon filtration and drying under high vacuum, 3 (10.49 g) was collected as a white solid. Material recovered from the mother liquor was recrystallized to afford an additional 2.68 g of 3 as white solid for a total yield of 82%. Reported analytical data refer to that of the first crop: Mp 92.8-94.1° C.; IR (ATR) 2939, 2863, 1451, 1381, 1227, 1026, 971 $cm^{-1}$; H NMR (400 MHz, $CDCl_3$) δ 4.80 (d, J=6.0 Hz, 2H), 4.61 (d, J=5.6 Hz, 2H), 4.50 (d, J=5.4 Hz, 2H), 4.45 (d, J=6.0 Hz, 2H), 3.38 (d, J=12.9 Hz, 2H), 2.75 (d, J=12.9 Hz, 2H), 1.61 (s, 6H); $^{13}C$ NMR (100 MHz, $CDCl_3$) δ 82.4, 82.0, 61.9, 38.4, 23.4; HRMS (ES) m/z calc for $C_{10}H_{18}O_3NaS$ (M+Na) 241.0874, found 241.0885.

To unambiguously characterize 3 as the sulfoxide, the corresponding sulfone was synthesized from sulfide 6.

3,3'-Sulfonylbis(methylene)bis(3-methyloxetane)

A suspension of oxone (650 mg, 1.06 mmol) in water (2.0 mL) was cooled to 10° C. and treated (dropwise) with a solution of 6 (108 mg, 0.533 mmol) in MeOH (2.0 mL). The solution was warmed to rt and stirred for 1 hour. MeOH was removed in vacuo, and the aqueous layer was diluted with water (5 mL) and extracted with $CH_2Cl_2$ (4×10 mL). The combined organic layers were washed with brine (5 mL), dried ($MgSO_4$), and concentrated in vacuo to afford the sulfone (120 mg, 96%) as a white solid: Mp 93.4-95.1° C.; IR (ATR) 2949, 2867, 1456, 1301, 1277, 967 $cm^{-1}$; $^1H$ NMR (400 MHz, $CDCl_3$) δ 4.68 (d, J=6.4 Hz, 4H), 4.46 (d, J=6.4 Hz, 4H), 3.43 (s, 4H), 1.69 (s, 6H); $^{13}C$ NMR (100 MHz, $CDCl_3$) δ 82.2, 62.6, 37.9, 23.3; HRMS (APCI) m/z calc for $C_{10}H_{19}O_4S$ (M+H) 235.1004, found 235.1032.

Determination of Log P Value of 3.

The log P (octanol-water partition coefficient) was determined using the shake-flask method. Three determinations were made. A representative procedure is as follows: a 250-mL separatory funnel was charged with a solution of 3 (50.0 mg) in water (50.0 mL) and n-octanol (50.0 mL). The funnel was capped and inverted 100 times. The funnel and contents were left to stand at room temperature (23.5° C.) for 40 hours. Aliquots of both phases were analyzed by UV/VIS (214 nm for the aqueous layer and 218 nm for the octanol layer), and the concentration in each layer was determined using previously generated calibration curves. In the case of the aqueous layer, a 10-fold dilution was necessary prior to measurement. All measurements were run in triplicate. The log P was determined as log ($[3]_{octanol}/[3]_{aqueous}$), and the average log P value from the 3 trials was −0.87.

Suitable starting materials for the synthetic schemes hereof include, for example:

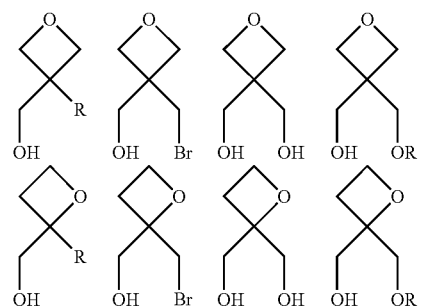

Examples—Increasing Aqueous Solubility

General procedure for determination of solubility in solutions of 3 and HPLC-grade water.
Preparation of Sulfoxide/Water Solutions.

Solutions of 3 and HPLC-grade water were prepared in 1 dram vials by dissolving the appropriate amount of sulfoxide 3 in HPLC-grade water (2.00 mL). In the case of the 25% solution of 3 in $H_2O$ (w/w), 3 (500 mg) was dissolved in water (1.50 mL). Each vial was placed on a platform shaker and shaken at 200 rpm for 30 minutes.
Solubility Measurements.

Eppendorf vials (1.5 mL size) were charged with model compounds in excess. Vials were charged with HPLC-grade water (0.500 mL) or the appropriate 3/water solution (0.500 mL). The vials were briefly vortexed and equilibrated in an end-over-end rotator at 30.0° C. for 20 hours. The vials were centrifuged (4000 rpm, 1300×g, 15 minutes, room temperature) directly after removal from the rotator, and aliquots of the supernatant (0.400 mL) were filtered through 0.45 syringe filters. The pH of each solution was measured using a ThermoScientific electrode (3 mm tip). Each solution was diluted with an appropriate volume of either absolute ethanol (quinine, naproxen, griseofulvin) or methanol (carbendazim). Concentrations were calculated by using previously generated calibration curves. Appropriate blanks were prepared by diluting aliquots (0.400 mL) of the 3/water solutions (or HPLC-grade water in the case of the control) in an analogous fashion to the sample being measured.

General procedure for determination of solubility in solutions of DMSO and HPLC-grade water.

Preparation of DMSO/Water Solutions.

Solutions of DMSO and HPLC-grade water were prepared in 1 dram vials by dissolving the appropriate amount of DMSO in HPLC-grade water (2.00 mL). Each vial was placed on a platform shaker and shaken at 200 rpm for 30 minutes.

Solubility Measurements.

Eppendorf vials (1.5 mL size) were charged with model compounds in excess. Vials were charged with either HPLC-grade water (1.00 mL) or the appropriate DMSO/water solution (1.00 mL). The vials were briefly vortexed and equilibrated in an end-over-end rotator at 30.0° C. for 20 hours. The vials were centrifuged directly after removal from the rotator (4000 rpm, 1300×g, 15 minutes, room teperature), and aliquots of the supernatant (0.800 mL) were filtered through 0.45 μm syringe filters. The pH of each solution was measured using a ThermoScientific electrode (3 mm tip). Each solution was diluted with an appropriate volume of either absolute ethanol (quinine, naproxen, griseofulvin) or methanol (carbendazim) Concentrations were calculated by using previously generated calibration curves. Appropriate blanks were prepared by diluting aliquots (0.800 mL) of the DMSO/water solutions (or HPLC-grade water in the case of the control) in analogous fashion to the sample being measured.

General procedure for solubility determination in mixtures of sulfoxide 3 in pH 7.0 buffer.

Preparation of Sulfoxide/Buffer Solutions.

In the case of a 10% w/w solution of sulfoxide 3 in 0.01 M pH 7.0 phosphate buffer, 3 (700 mg) was dissolved in 0.01 M $Na_2HPO_4/NaH_2PO_4$ buffer (6.30 mL) and equilibrated on a platform shaker at 200 rpm for 30 minutes at room temperature. In the case of a 25% w/w solution of sulfoxide 3 in 0.01 M pH 7.0 phosphate buffer, 3 (1.50 g) was dissolved in 0.01 M $Na_2HPO_4/NaH_2PO_4$ buffer (4.50 mL) and equilibrated on a platform shaker at 200 rpm for 30 minutes at room temperature.

Solubility Measurements.

Eppendorf vials (1.5 mL size) were charged with model compounds in excess. Vials were charged with either pH 7.0 phosphate buffer (1.00 mL) or the appropriate 3/buffer solution. The vials were briefly vortexed and equilibrated in an end-over-end rotator at 30.0° C. for 20 hours. The vials were centrifuged directly after removal from the rotator (4000 rpm, 1300×g, 15 minutes, room temperature), and aliquots of the supernatant (0.800 mL) were filtered through 0.45 μm syringe filters. The pH of each solution was measured using a ThermoScientific electrode (3 mm tip) after calibration. Each solution was diluted with an appropriate volume of either absolute ethanol (quinine, naproxen) or methanol (carbendazim). Concentrations were determined using standard additions of a stock solution of the compound in either absolute ethanol (quinine, naproxen) or methanol (carbendazim) to aliquots of the diluted filtrates.

General procedure for kinetic solubility measurements. A polypropylene tube was charged with PBS solution (490 μL). To the buffer was added a 10 mM stock solution of compound (10 μL). The tube was vortexed and equilibrated on an end-over-end rotator for 15 minutes at room temperature. Aliquots (400 μL) were filtered through 0.45 μm syringe filters and diluted to 5.0 mL with absolute MeOH. Concentrations were determined by UV/VIS analysis.

General procedure for brine shrimp toxicity assays. Sample preparation. Stock solutions of 3 were prepared by dissolving 3 (50.0 mg) in 5.0 HPLC grade water (5.0 mL), (solution A) and 3 (2.50 g) in HPLC grade water (10.0 mL) (solution B). Stock solutions of DMSO were prepared by diluting DMSO (45 μL) with HPLC grade water (5.0 mL) (solution C) and DMSO (2.27 mL) with HPLC grade water (10.0 mL) (solution D).

In each case, 5 replicates were performed. Each replicate was performed in a 2 dram vial marked at the 4 and 5 mL volume points. To each vial was added artificial sea water (3 mL) followed by the appropriate volume of stock solution. For set 1 (1.0 mg/mL), solution A (0.500 mL) or solution C (0.500 mL) was added. For set 2 (5.0 mg/mL), solution B (0.100 mL) or solution D (0.100 mL) was added to each vial. For set 3 (20.0 mg/mL), solution B (0.400 mL) or solution D (0.400 mL) was added to each vial. For set 4 (50.0 mg/mL), solution B (1.00 mL) or solution D (1.00 mL) was added to each vial. Controls containing HPLC grade water (0.100 mL, 0.400 mL, and 1.00 mL) were prepared in the same manner, and five replicates of each control were prepared.

Brine Shrimp Hatching.

Brine shrimp eggs (San Francisco Bay Brand) were hatched in a commercial salt mixture (Instant Ocean). Constant aeration was provided using a pump and airstone, and illumination was maintained using a desk lamp. The shrimp were collected in a separate tank after 48 hours and used within 3-4 hours of collection.

Assay.

Brine shrimp were added to each vial using a plastic transfer pipet. After the shrimp were transferred, artificial sea-water was added until the volume reached the 5-mL mark. One drop of a yeast suspension prepared by suspending 11 mg yeast in sea-water (20 mL) was added to each vial. The shrimp were counted at t=24 hours. Another drop of freshly prepared yeast solution (6 mg in 10 mL sea water) was added, the vials were maintained under illumination, and shrimp were counted at t=48 hours.

General procedure for calculation of water absorption. Oven-dried flasks capped with septa were cooled under a $N_2$ atmosphere and charged with a volume of the appropriate solutions (DMSO, 3.0 mL; NMP, 600 μL; 25% 3/NMP, 600 μL). The water content was determined by Karl Fischer titration using about 100 μL aliquots (t=0 measurement). Each septum was pierced with a 1.5 inch 18 gauge needle and left to stand at room temperature for 7 days. The water content was measured at the end of this period (t=7 d measurement) by Karl Fischer titration. All measurements were made in duplicate.

Results and Discussion.

With reference to Scheme 1, water soluble sulfoxide 3 was prepared in three steps from alcohol 4, which is commercially available or readily prepared from inexpensive 2-(hydroxymethyl)-2-methylpropane-1,3-diol. Briefly, treatment of 4 with TsCl in pyridine afforded tosylate 5. Dimeric sulfide formation using $Na_2S$ followed by oxidation with $NaIO_4$ provided sulfoxide 3 (Scheme 1). The synthesis is amenable to large-scale preparation and requires no chromatography.

Initially, the aim was to use sulfoxide 3 as a substitute for DMSO in chemical transformations such as modified Swern and Kornblum oxidations. The reasoning was that the resulting sulfide 6, being less volatile and odorous than dimethyl sulfide, would be a more tractable byproduct on industrial scale. Additionally, bisoxetanyl sulfoxide 3 is water soluble, and it was found that the sulfide byproduct could be removed from reaction mixtures by an oxidative work-up and aqueous washing procedure. Surprisingly, however, sulfoxide 3 was not a viable oxidizing agent in Kornblum oxidations. For example, α-bromoacetophenone was stable to an excess of 3 when monitored in CD$_3$CN over the course of several weeks; under the same conditions, α-bromoacetophenone was reactive with DMSO within 2 days of treatment.

Taking advantage of the stability and hydrophilicity of 3, its use for the solubility enhancement of poorly aqueous soluble compounds was explored. Oxetanes are attractive functional groups for increasing aqueous solubility due to their rigid geometries and exposed polar surface area at the ring ether. Among unsubstituted cyclic ethers, oxetane has the greatest basicity, which may be attributed to a smaller carbon to oxygen ratio and a larger dipole moment than its larger counterparts (e.g., THF and THP). Recently, Miller, Carreira, and coworkers demonstrated that replacing a gem-dimethyl group with an oxetane moiety can increase a scaffold's aqueous solubility by up to three orders of magnitude while also enhancing metabolic stability. It was thought that sulfoxide 3 may have sufficient aqueous solubility to be completely miscible with water at useful cosolvent concentrations while also disrupting the hydrogen-bonding network of water, thus aiding in solubilization of lipophilic drug candidate compounds.

Figure 2:
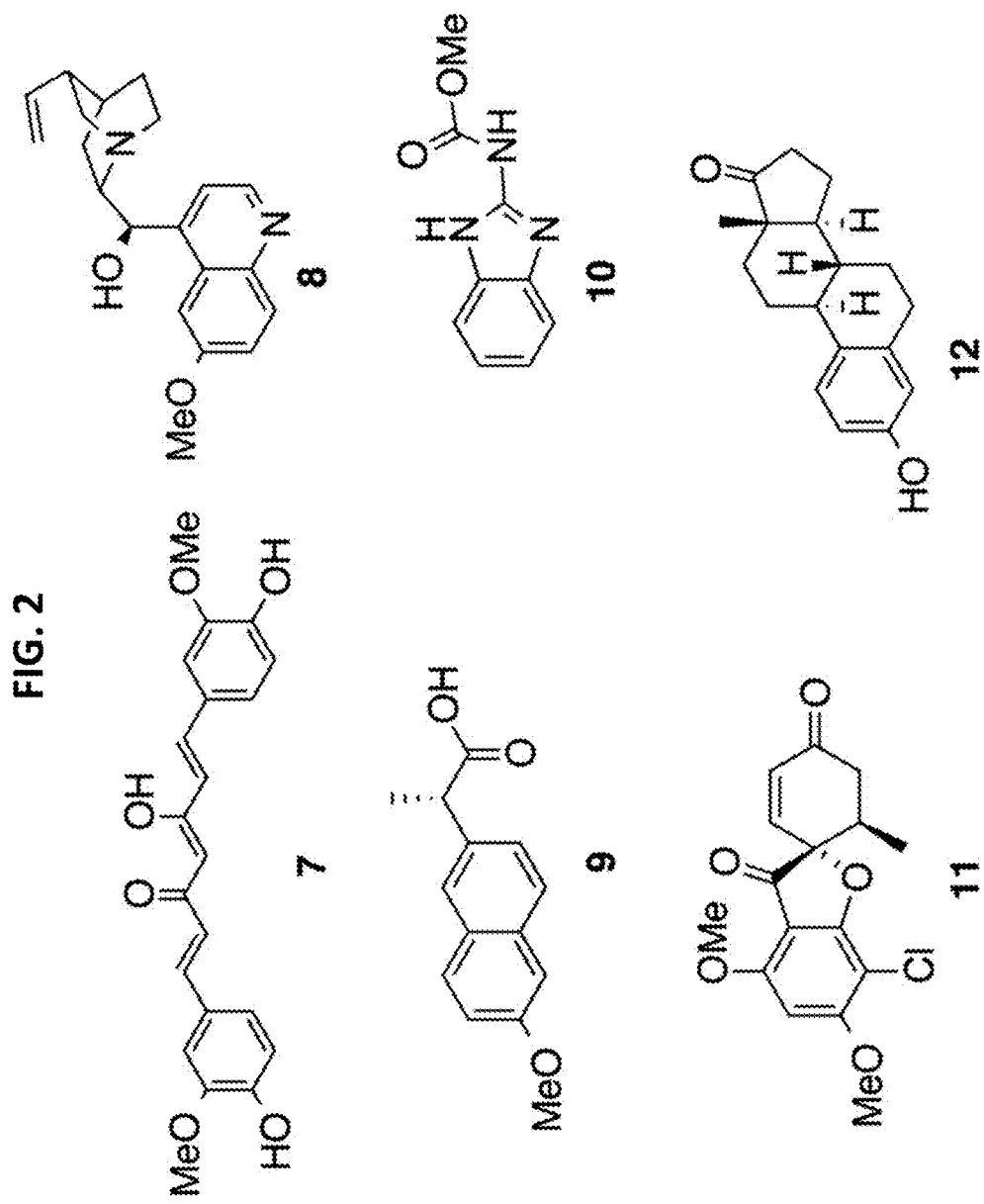
FIG. 2 provides the structures of compounds screened in an aqueous solubility study.
Figure 3:
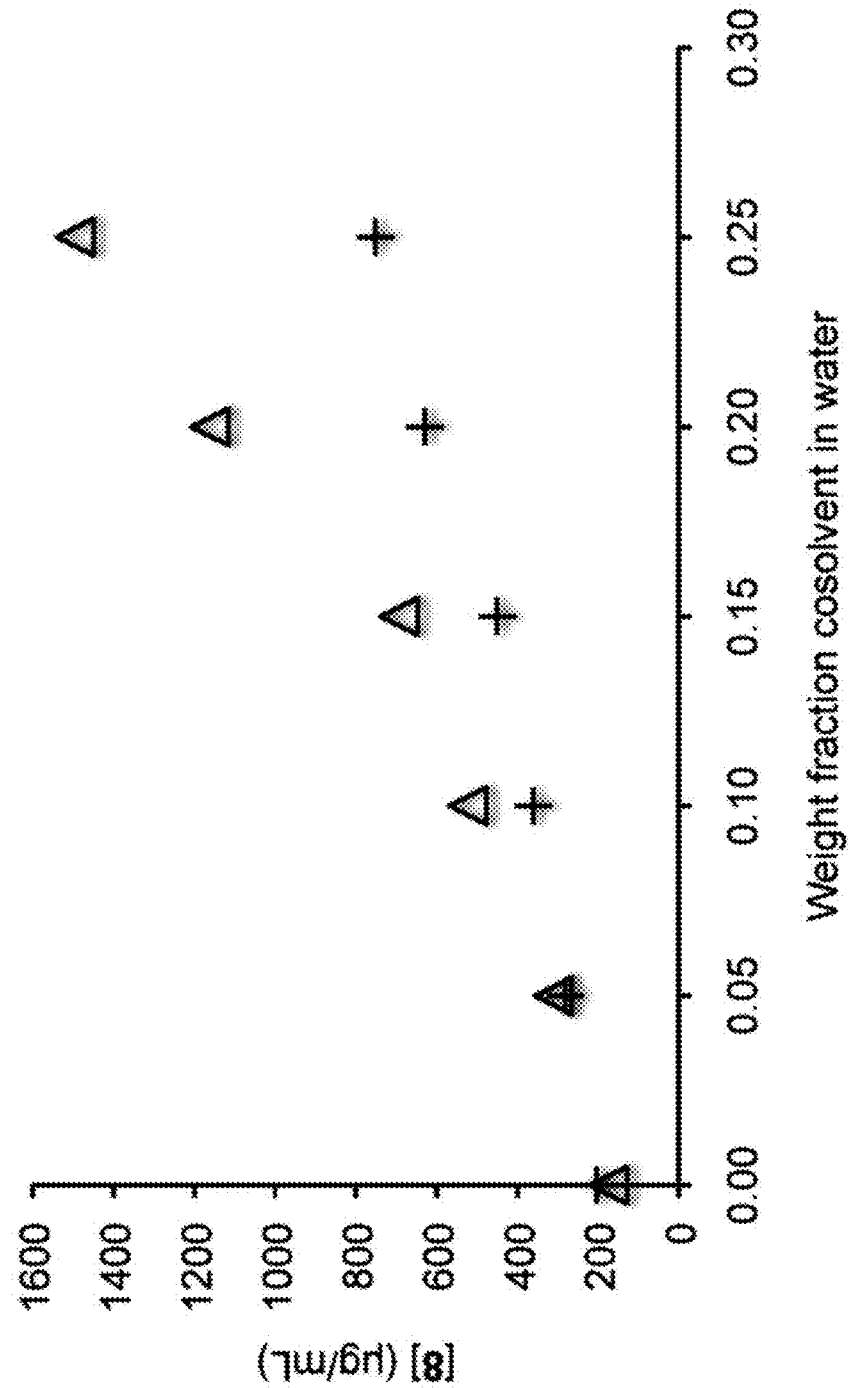
FIG. 3 is a graph of concentration of quinine 8 versus weight fraction of cosolvent in water, illustrating the solubility of quinine 8 in aqueous solutions with sulfoxide 3 (Δ) and DMSO (+) as cosolvents. Each trial was run in duplicate and each point represents the average of the duplicate trials. In the case of sulfoxide 3, the pH varied from 8.7 (with no additive) to 9.4 (with a 0.25 weight fraction additive). In the case of DMSO, the pH varied from 8.9 (with no additive) to 9.5 (with a 0.25 weight fraction additive).
Figure 4:
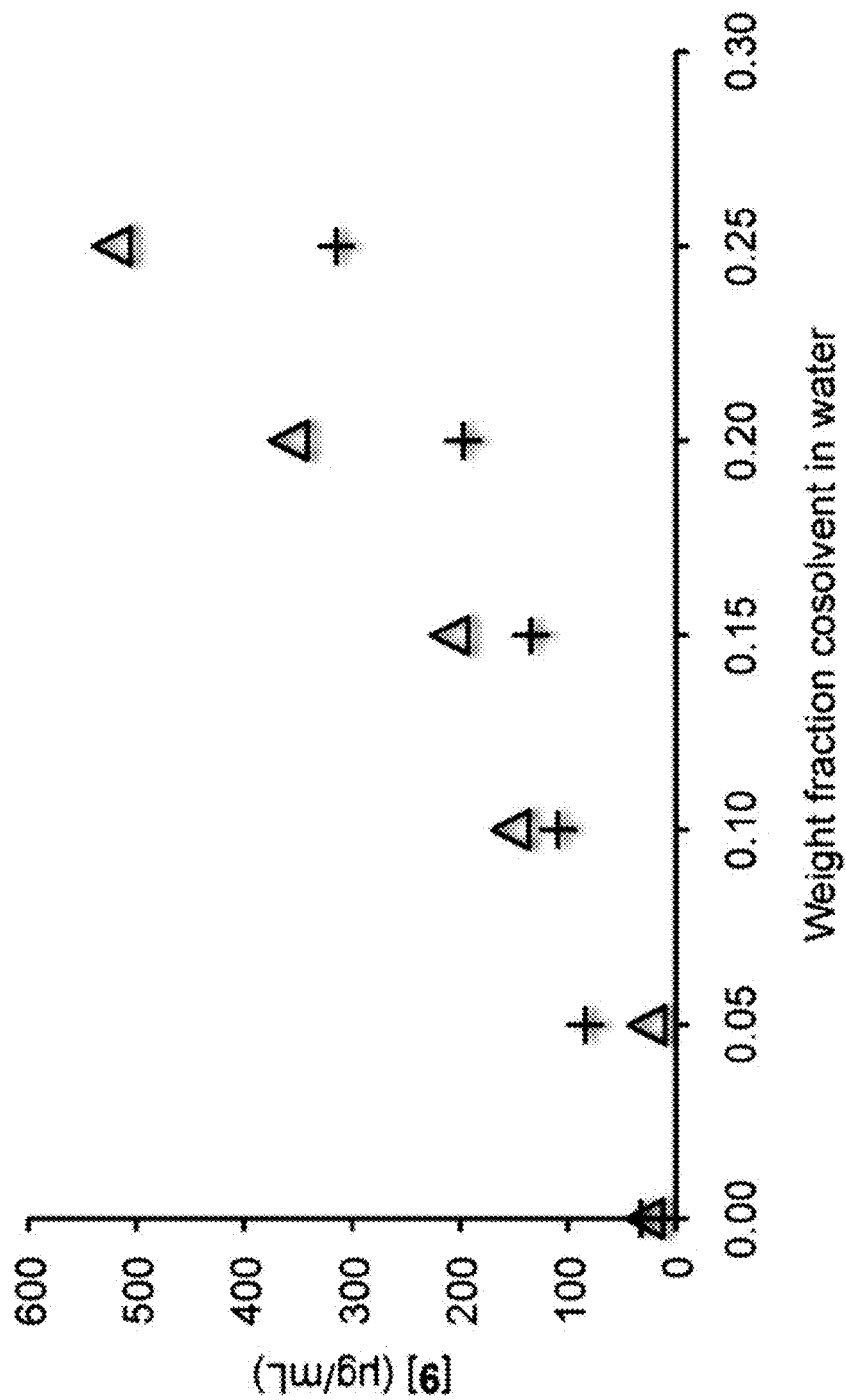
FIG. 4 is a graph of concentration of naproxen 9 versus weight fraction of cosolvent in water, illustrating the solubility of naproxen 9 in aqueous solutions with sulfoxide 3 (Δ) and DMSO (+) as cosolvents. Each trial was run in duplicate and each point represents the average of the duplicate trials. In the case of sulfoxide 3, the pH varied from 4.6 (with no additive) to 4.2 (with a 0.25 weight fraction additive). In DMSO, the pH varied from 4.8 to 4.4.
Figure 5:
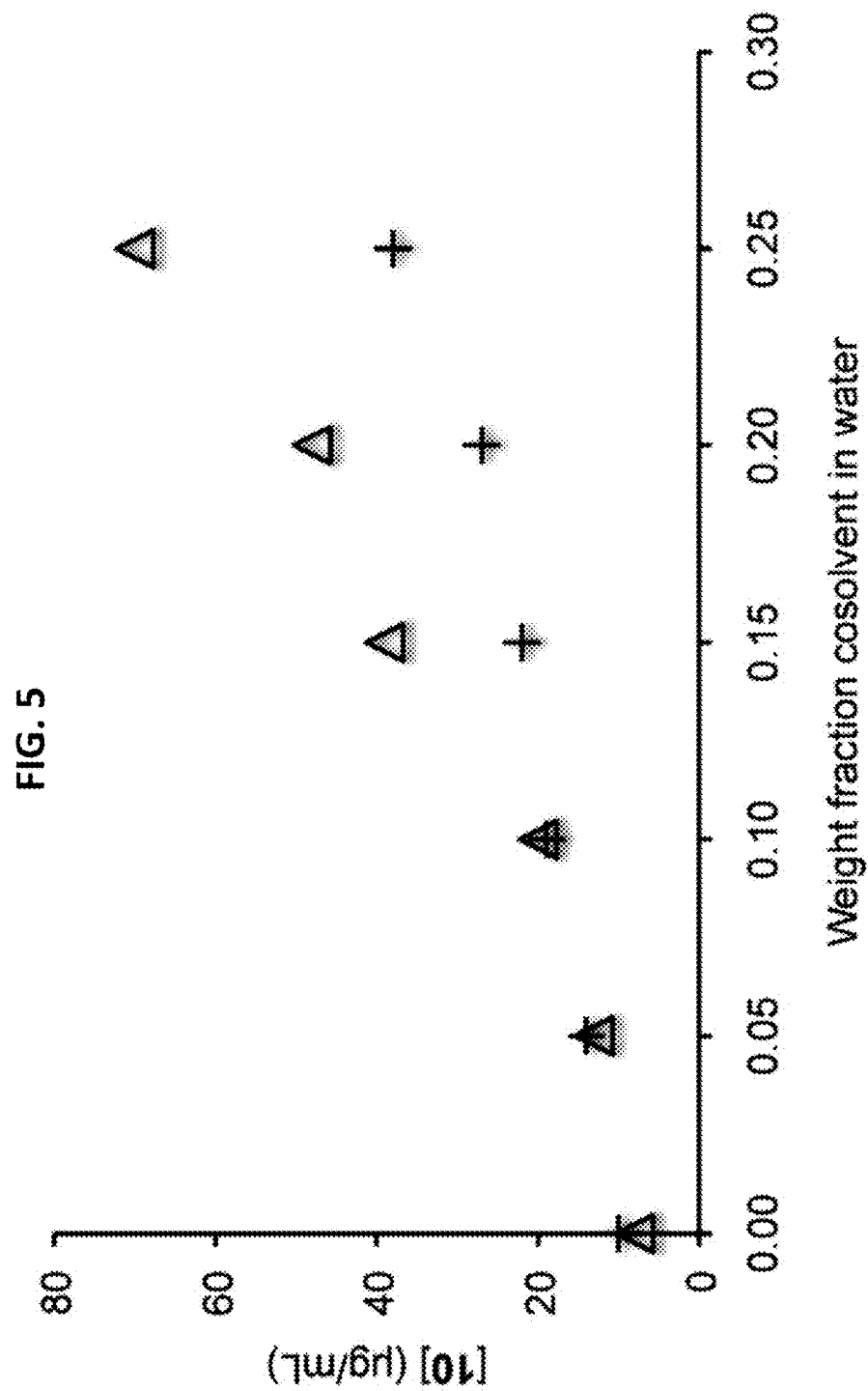
FIG. 5 is a graph of concentration of carbendazim 10 versus weight fraction of cosolvent in water, illustrating the solubility of carbendazim 10 in aqueous solutions with sulfoxide 3 (Δ) and DMSO (+) as cosolvents. Each trial was run in duplicate and each point represents the average of the duplicate trials. In the case of sulfoxide 3, the pH varied from 6.7 (with no additive) to 7.0 (with a 0.15 weight fraction additive). In DMSO, the pH varied from 6.8 (with no additive) to 7.4 (with a 0.25 weight fraction additive).
Figure 6:
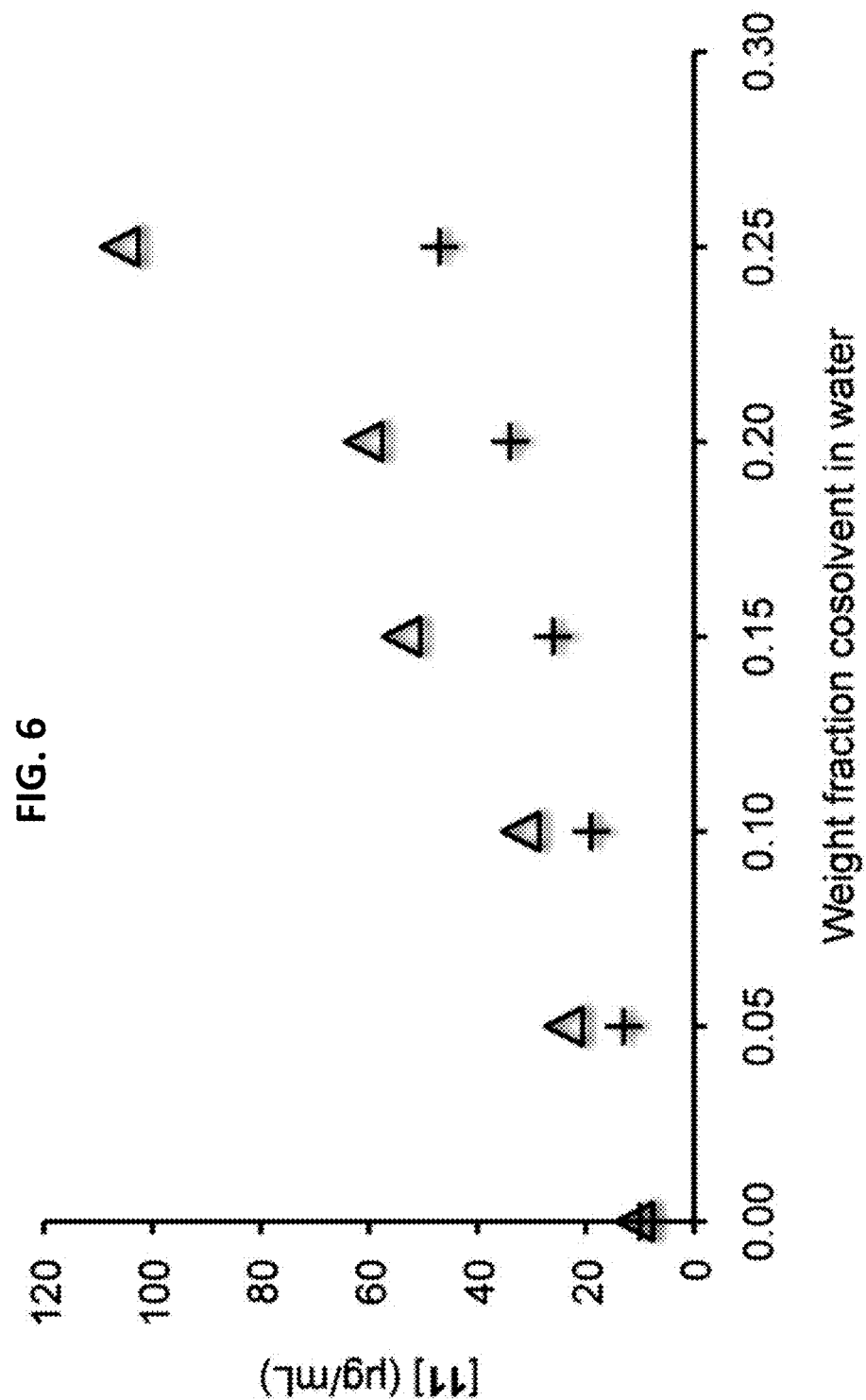
FIG. 6 is a graph of concentration of griseofulvin 11 versus weight fraction of cosolvent in water, illustrating the solubility of griseofulvin 11 in aqueous solutions with sulfoxide 3 (Δ) and DMSO (+) as cosolvents. Each trial was run in duplicate and each point represents the average of the duplicate trials. In the case sulfoxide 3, the pH varied from 6.3 (with no additive) to 6.8 (with a 0.20 weight fraction additive). In DMSO, the pH varied from 6.3 (with no additive) to 6.8 (with a 0.20 weight fraction additive).

To evaluate the utility of sulfoxide 3 as a solubilizing agent, a test set of poorly aqueous soluble compounds, beginning with curcumin 7 was chosen (FIG. 2). Curcumin has shown promise in treating colon cancer and various other disorders, but its use is limited in part by its low aqueous solubility (0.6 µg/mL at ambient temperature, as high as 7.4 µg/mL upon heating) and consequently limited bioavailability. The solubility of curcumin was measured by UV/VIS spectroscopy after equilibration for 20 hours at ambient temperature in an end-over-end rotator. An increase in aqueous solubility at ambient temperature to 60±20 µg/mL using a 25 wt % solution of 3 in water was observed.

The solubility enhancement of 8-12 was further examined by equilibrating the compounds in solutions of increasing amounts of sulfoxide 3 in water. Gratifyingly, up to 10-fold increases in aqueous solubility were observed for 8-11, and almost 2-fold improvements in aqueous solubility were observed in comparison to equivalent DMSO/water solutions (FIGS. 3-6).

Based on the solubility curves (FIGS. 3-6), the sulfoxide 3 and DMSO function as cosolvents rather than complexing agents. According to the model derived by Yalkowsky, an exponential increase in observed solubilities occurs with increasing the volume fraction solvent according to equation 1, where $S_{mix}$ and $S_w$ are the solubility of the solute in the cosolvent mixture and water, respectively, σ is the solubilizing power of the cosolvent, and $f_c$ is the volume fraction of the cosolvent. The slope of a semi-log plot (σ) is related to the cosolvent's ability to disrupt the intermolecular hydrogen bond network of water and form a less polar solvent mixture. Thus, the solubilizing power of sulfoxide 3 and DMSO can be accounted for when comparing the difference in the experimental log P of sulfoxide 3 (−0.87) and the reported log P of DMSO (−1.3).

$$\text{Log } S_{mix} = \log S_w + \sigma f_c \quad (1)$$

Although not bound by any theory, complexation can be tentatively ruled out as a solubilization mechanism assuming that additive-solute complexes would form in a 1:1 ratio. If that were the case, a linear correlation between additive fraction and solubility would be observed.

The aqueous solubility of estrone 12 is low (0.8 ng/mL), and we were unable to quantify the aqueous solubility or observe an increase in solubility in the case of a 25% (w/w) mixture of 3 and water; however, increasing the pH of the media using a pH 9.0 buffer (Borax) as well as addition of NMP to generate a ternary mixture was useful. In this case, the ternary mixture of 3:1:1 pH 9.0 buffer:NMP:DMSO was more effective at solubilization than the 3:1:1 pH 9.0 buffer:NMP:3 mixture (Table 1, entries 3 and 4).

TABLE 1

Solubility of estrone 12 in media buffered at pH 9.0.

| Entry | Medium | Solubility (µg/mL)[a] |
|---|---|---|
| 1 | 3:1 pH 9.0 buffer/3 | 30 ± 10 |
| 2 | 3:1 pH 9.0 buffer/NMP | 63 ± 5 |
| 3 | 3:1:1 pH 9.0 buffer/NMP/3 | 160 ± 20 |
| 4 | 3:1:1 pH 9.0 buffer/NMP/DMSO | 230 ± 30 |

[a]Solubility was determined after equilibration for 20 h at 30.0° C. Data were obtained by UV/VIS analysis of the saturated solutions and were confirmed by analysis of independently prepared estrone standards. Each entry represents a mean solubility ± standard deviation (n = 3).

The solubility of test compounds with ionizable functionalities in 0.01 M pH 7.0 phosphate buffer was also explored (Table 2). In the case of naproxen, the sulfoxide had little effect on the ionized substrate even at 25% w/w concentrations. The effect on the solubility of quinine was diminished at 10% w/w, but an advantage in using 3 was observed in 25% w/w solutions. The solubility of carbendazim in the buffered medium was the same as in solutions made from unbuffered HPLC-grade water.

TABLE 2

Solubility of selected model substrates in solutions of sulfoxide 3 in 0.01M pH 7.0 phosphate buffer.

| Entry | Compound | Weight percent 3 in pH 7.0 buffer | Solution pH[a] | Measured solubility (µg/mL)[b] |
|---|---|---|---|---|
| 1 | 8 | 0 | 6.0 | 1100 (780)[d] |
| 2 | 8 | 10 | 5.8 | 1900 (1300)[d] |
| 3 | 8 | 25 | 5.2 | 6200 (3900)[d] |
| 4 | 9 | 0 | 7.6 | 950[c] |
| 5 | 9 | 10 | 8.0 | 1100 |
| 6 | 9 | 25 | 8.2 | 1400 |
| 7 | 10 | 0 | 6.8 | 10 |
| 8 | 10 | 10 | 6.9 | 34 |
| 9 | 10 | 25 | 7.1 | 77 |

[a]The pH was measured electrochemically after excess compound was filtered from the solution.
[b]Measurements were performed in duplicate unless otherwise noted.
[c]Average of 5 trials.
[d]The two numbers represent data from separate trials where entries 1-3 were run in parallel. There was some variability in the results from the two trials.

The kinetic solubility of two test compounds, carbendazim 10 and griseofulvin 11, in PBS solution after adding stock solutions prepared in three media: DMSO, NMP, and 25% 3/NMP was also determined. The test compounds were prepared at concentrations of 10 mM and added to the buffer at room temperature such that cosolvent concentration was fixed at 2%. The measured solubility was consistent for both test compounds across the three stock solutions. While the kinetic solubility of griseofulvin was found to be higher than reported (and nearing the threshold solubility of 200 µM), there was no statistical difference in the kinetic solubilities of the test compounds among the three different media.

TABLE 3

Kinetic solubility measurements in PBS solutions.

| Entry | Compound | Medium of stock solution | Kinetic solubility (μM)[a] |
|---|---|---|---|
| 1 | 10 | DMSO | 140 ± 13[b] |
| 2 | 10 | NMP | 160 ± 5 |
| 3 | 10 | 25% 3/NMP | 150 ± 9 |
| 4 | 11 | DMSO | 170 ± 16 |
| 5 | 11 | NMP | 180 ± 13 |
| 6 | 11 | 25% 3/NMP | 190 ± 7 |

[a]Data are reported as mean ± standard deviation (n = 3).
[b]Data are reported as mean ± standard deviation (n = 5).

Figure 7:
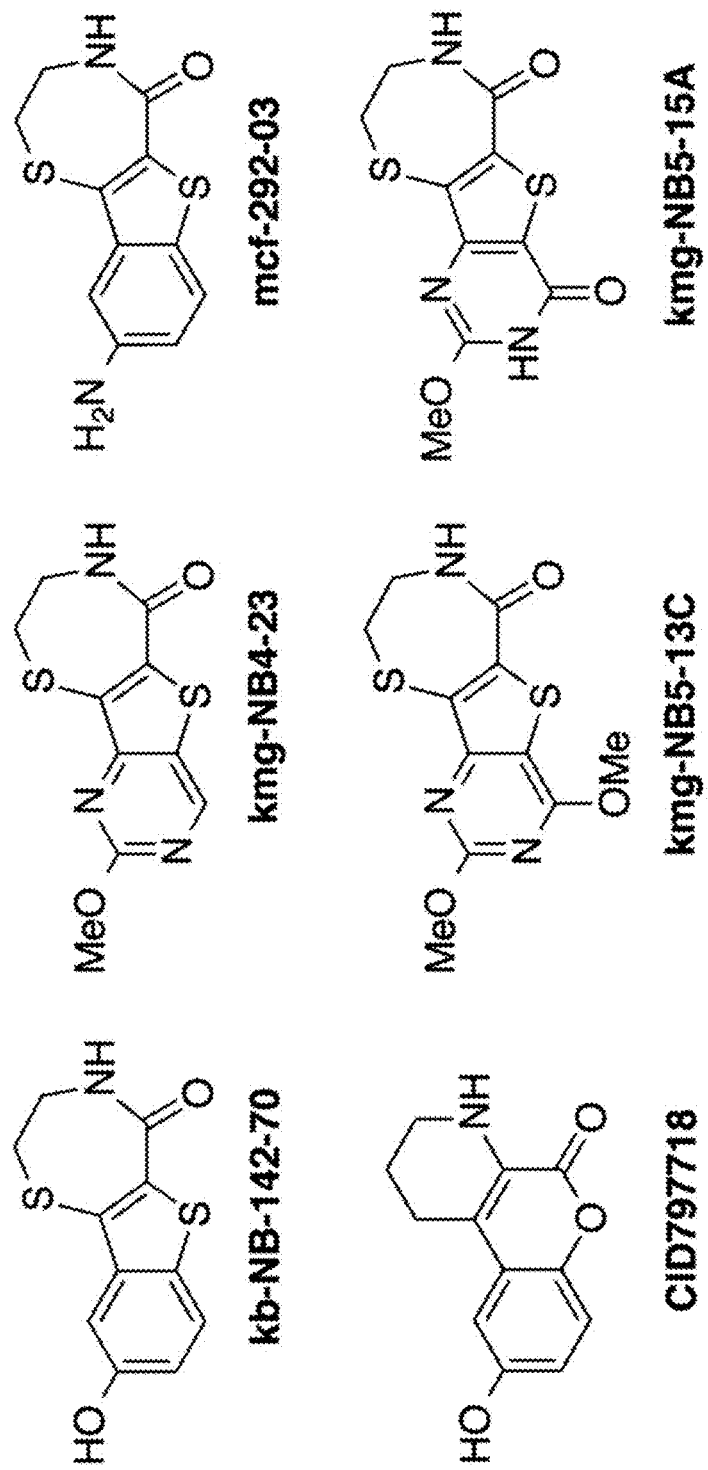
FIG. 7 provides the structures of compounds assayed for PKD1 inhibitory activity. The structures have been reported previously.
Figure 8:
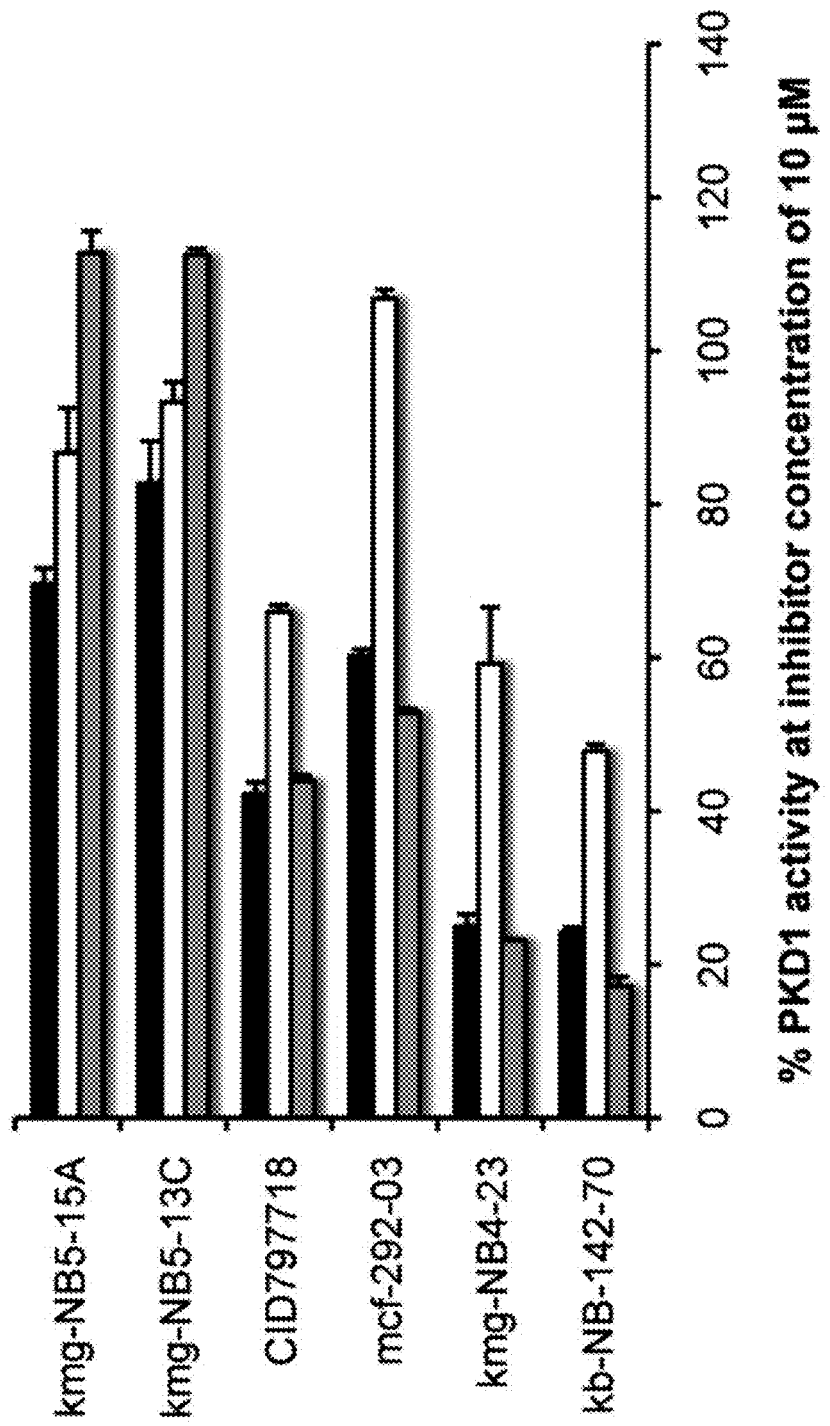
FIG. 8 is a plot of PKD1 activity with compound concentrations of 1 µM. Stock solutions were prepared in three different media (DMSO (■), NMP (□), and 25% 3/NMP (■)) at concentrations of 10 mM, and dilutions were performed using the same media. The % PKD1 activity is reported as the mean, and error bars represent SEM (n=3). The % PKD1 activity was determined as previously described.
Figure 9:
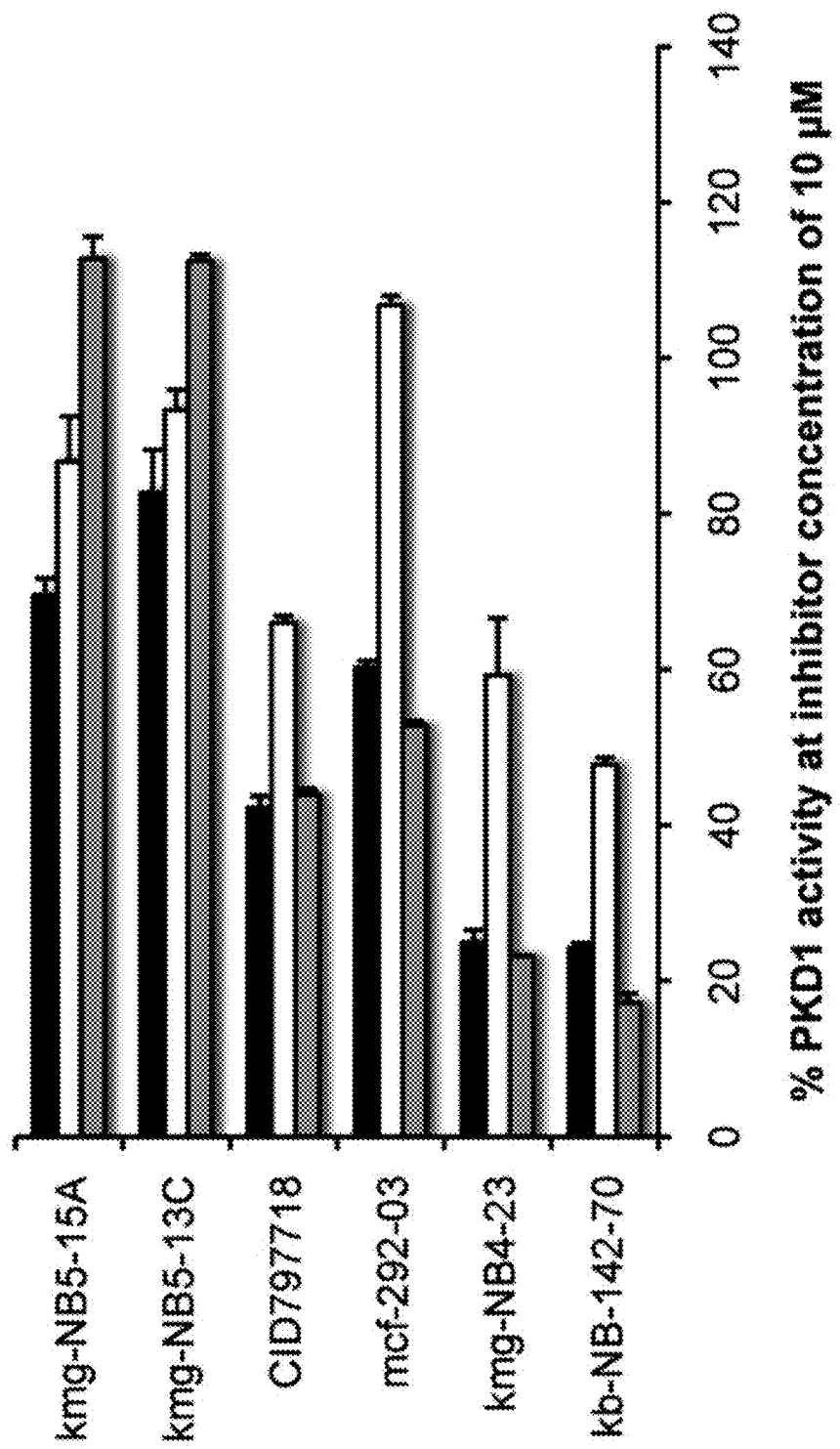
FIG. 9 is a plot of PKD1 activity with compound concentrations of 10 µM. Stock solutions were prepared in three different media (DMSO (■), NMP (□) and 25% 3/NMP (■)) at concentrations of 10 mM, and dilutions were performed using the same media. The % PKD1 activity is reported as the mean, and error bars represent SEM (n=3). The % PKD1 activity was determined as previously described.
Figure 10A:
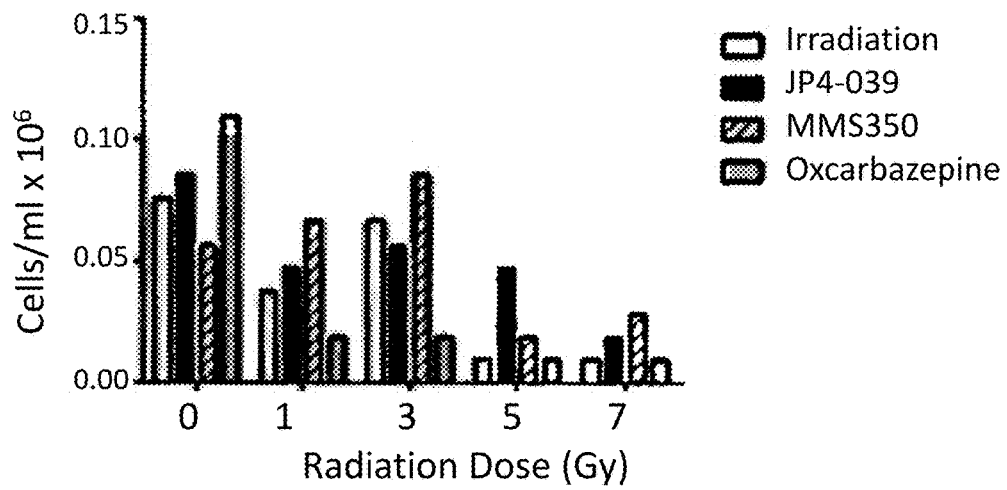
FIGS. 10A-10D provide data from a screening experiment where 32D cl 3 cells were irradiated to doses of 0, 1, 3, 5, or 7 Gy and placed in T25 flasks. Either JP4-039 or MM350 were added at 10 µM and incubated in a $CO_2$ incubator at 37° C. At Day 3 or 5 after irradiation, the cells were counted and the viability determined. In these experiments MMS350 is comparable to JP4-039 in the number of cells and viability.
Figure 10B:
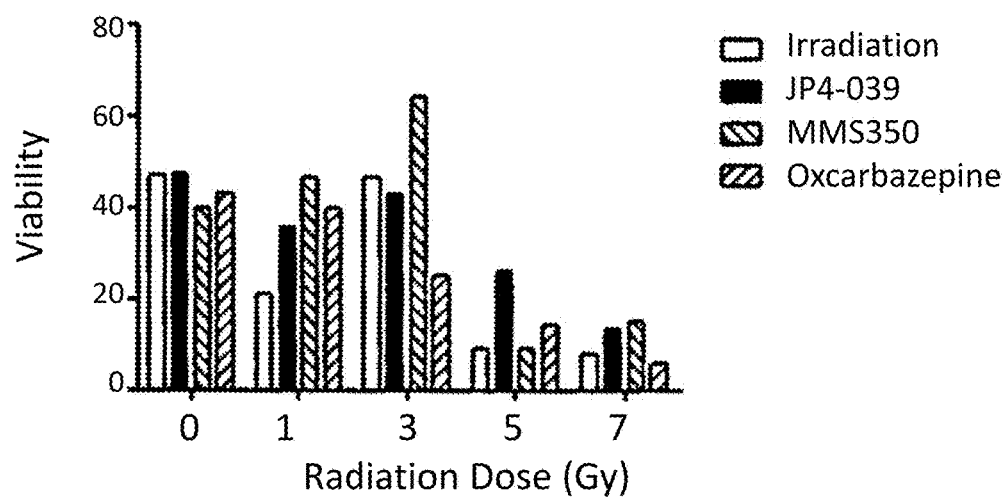
Figure 10C:
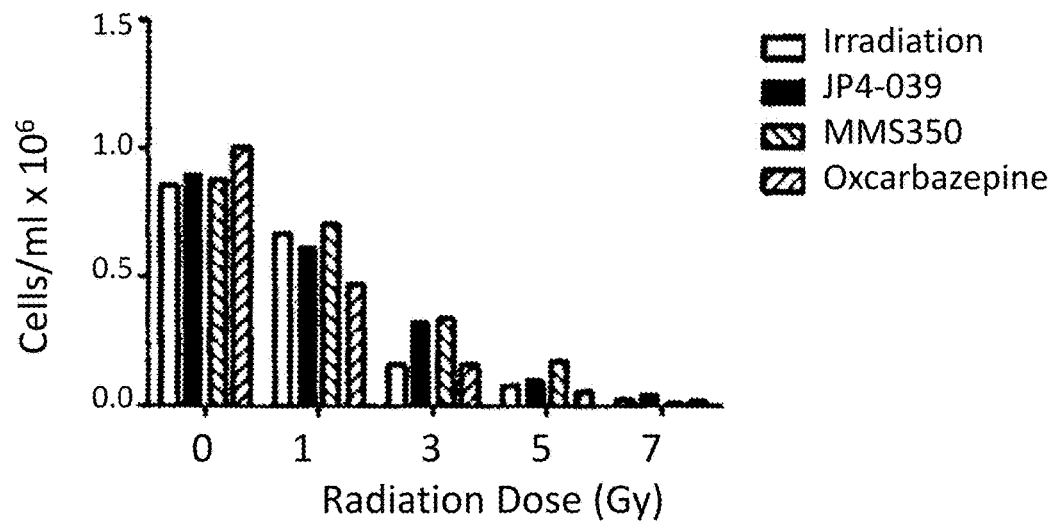
Figure 10D:
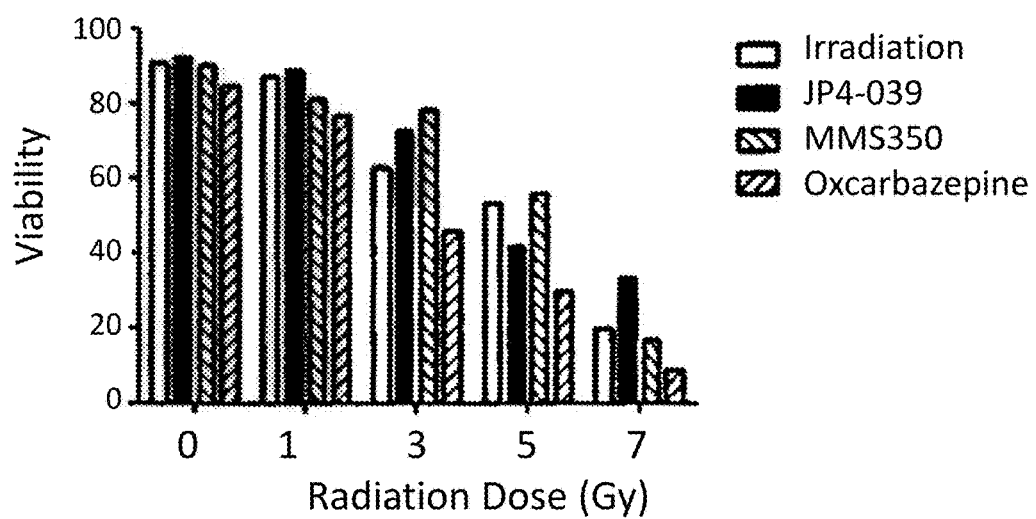
Figure 11:
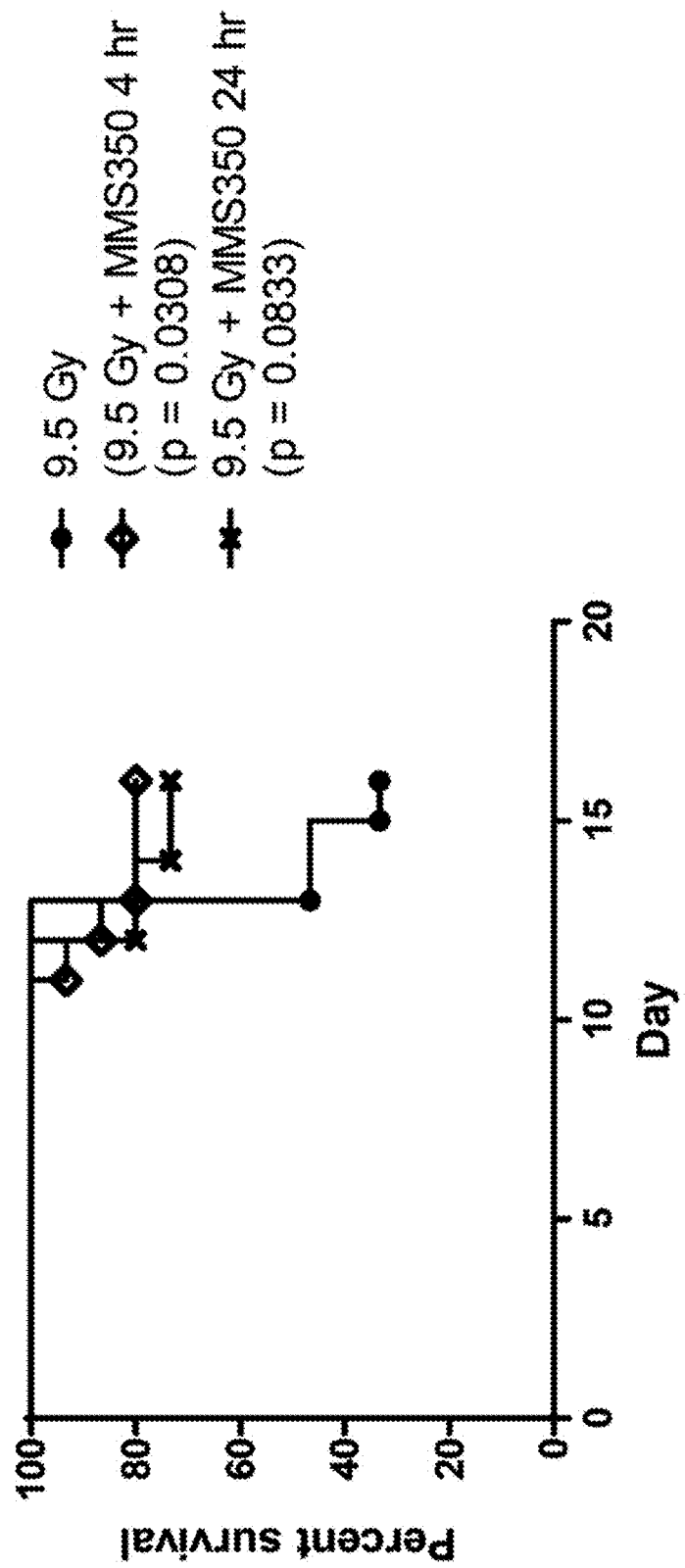
FIG. 11 is a graph of present survival versus day, illustrating the survival of mice injected IP with 20 mg/kg MMS350 dissolved in PBS. The mice were irradiated to 9.5 Gy total body irradiation and then injected at 4 or 24 hours after irradiation.

Recently, a series of compounds with nanomolar to micromolar inhibitory activity against the serine/threonine protein kinase D (PKD) isoform PKD1 was disclosed (FIG. 7). Several lead structures, especially those containing a pyrimidine moiety, suffered from poor solubility not only in aqueous media but also in DMSO. To test the feasibility of using sulfoxide 3 as a cosolvent for in vitro assays, its use in the radiometric PKD1 inhibition assay was examined. Inhibitory activity at two concentrations (1 μM and 10 μM) was measured using compound stock solutions in three formulations: DMSO, NMP, and 25% 3/NMP (FIGS. 8 and 9). Comparable biological efficacy was observed for stock solutions in 3/NMP vs DMSO. Most significantly, sulfoxide 3 did not interfere with the standard PKD1 inhibition assay.

Toxicity.

The strain energy of the oxetane ring (25.2 kcal/mol) raises concerns about the electrophilicity and related toxicity and mutagenicity of molecules containing an oxetane moiety. Computational models have indicated that despite having comparable strain energy to oxirane (26.8 kcal/mol), oxetane is $10^6$-times less susceptible to nucleophilic addition than oxetane. Animal studies have implicated the potential carcinogenicity of oxetane and 3,3-dimethyloxetane; it was shown that both compounds induce tumor formation at the site of injection in rats. However, a recent report studying the alkylating ability of oxetane, 3,3-dimethyloxetane, and 3-methyl-3-oxetanemethanol (4) demonstrated that these oxetanes are neither mutagenic nor genotoxic. Furthermore, alkylation of NBP 4-(p-nitrobenzyl)pyridine was only observed at acidic pH, implicating that oxetanes do not act as alkylating agents at physiological pH.

In order to assess the systemic toxicity of oxetane-substituted sulfoxide 3, a brine shrimp assay was performed (Table 4). Brine shrimp floating in water containing concentrations of 3 up to 20 mg/mL showed <10% mortality after 48 hours. Shrimp incubated in water containing 50 mg/mL of 3 had 85% mortality after 24 hours and 100% mortality within 48 hours. These data indicate an $LC_{50}$ of approximately 32 mg/mL (i.e. at 147 mM). In comparison, brine shrimp treated with DMSO at the same concentrations showed no mortality after 24 h and only 15% mortality after 48 h at 50 mg/mL of DMSO. These results indicate that sulfoxide 3 may be tolerated in biological assays in concentrations by mass of up to 2%.

TABLE 4

Results from a brine shrimp assay to access the toxicity of sulfoxide 3.

| Entry | Compound | Concentration (mg/mL) | % Mortality[a] after 24 h | % Mortality[a] after 48 h |
|---|---|---|---|---|
| 1 | 3 | 0 | <10 | 10 |
| 2 | 3 | 1 | 0 | 0 |
| 3 | 3 | 5 | 0 | 0 |
| 4 | 3 | 20 | 0-10 | 0-10 |
| 5 | 3 | 50 | 85 | 100 |
| 6 | DMSO | 0 | <10 | 10 |
| 7 | DMSO | 1 | 0 | 0-10 |
| 8 | DMSO | 5 | 0 | 0-6 |
| 9 | DSMO | 20 | 0 | 0 |
| 10 | DSMO | 50 | 0 | 15 |

[a]Percent mortality was determined for an average of 5 trials. Percent mortality was determined by estimating the number of shrimp showing no motility after several minutes of observation.

The cellular toxicity of sulfoxide 3 was further determined for a breast cancer cell line (MDA-MB-231) and a liver cell line (HepG2). In both cases, the $GI_{50}$ for 3 was ca. 200 mM, whereas the $GI_{50}$ for DMSO was determined ca. 800 mM. Interestingly, both cell lines exhibited the same threshold effect as observed in the case of the brine shrimp, showing only very limited toxicity at concentrations up to ca. 100 mM.

Because sulfoxide 3 is a solid, it would have to be mixed with an appropriate water-soluble cosolvent to act as a compound storage additive. NMP was chosen for exploring this potential application due to its thermal stability and low toxicity. Furthermore, it had been demonstrated that NMP had a greater solubilizing power than ethanol and propylene glycol, and NMP was previously used for solubility enhancements both in bioassays and commercial pharmaceutical applications such as the Eligard® formulation for delivery of leuprolide to prostate cancer patients. The compound test set (FIG. 2) was stored in 25% w/w solutions of 3 and NMP for 6 weeks at −20° C. During this time, it was noted that 3 partly precipitated from the solution at this temperature, but no change in model compound concentration was observed after thawing of the storage vessels.

A study performed at Abbott indicated that water absorption might induce more significant compound degradation than oxygen exposure. To ascertain the degree of water absorption, a 25% w/w 3/NMP solution was monitored for one week at ambient temperature (Table 4). Although significant water absorption was observed (ca. 7,000 ppm over the course of 7 days), the 3/NMP solution absorbed less water than NMP alone. This result indicates that the hygroscopicity of sulfoxide 3 is low relative to NMP.

TABLE 5

Comparative water absorption measurements of possible compound storage media.

| Entry | Medium | Water content at t = 0 (ppm)[a] | Water content at t = 7 d (ppm)[a] |
|---|---|---|---|
| 1 | DMSO | 160, 170[b] | 1080, 1130[b] |
| 2 | NMP | 150, 130[c] | 12,090, 17,000[c] |
| 3 | 25% 3/NMP (w/w) | 160, 200[c] | 6500, 8600[c] |

[a]Water content was analyzed by Karl Fischer titration. The two values listed represent individual vessels, the first value in each column corresponding to the same vessel at each time-point.
[b]Average of 3 measurements.
[c]Average of 2 measurements.

Conclusion.

The utility of oxetane-substituted sulfoxide 3 as a cosolvent for enhancing the aqueous solubility of model drug compounds was demonstrated. Although the relative acute toxicity of 3 was higher than that of DMSO in brine shrimp and cell based assays, it was sufficiently low to permit its use in cellular and in vivo assay development in up to 2% final concentrations. Furthermore, sulfoxide 3 proved experimentally to be far less oxidizing than DMSO, and this property could provide greater stability to long-term compound storage solutions. The amount of water absorption will likely depend on the choice of cosolvent, but the nature of 3 (being a solid) may allow the assay developer to choose cosolvents which either do not absorb as much water as DMSO (or NMP) or do not undergo the dramatic changes in physical properties observed in the case of wet DMSO solutions. As shown in our PKD1 assays, 3 does not alter the biochemical readout in standard in vitro assays.

This is the first report of the incorporation of an oxetane moiety into a cosolvent structure for solubility enhancement. The oxetane motif allows for the design of more lipophilic cosolvents that still maintain good aqueous miscibility due to the dipole moment at the oxetane oxygen.

EXAMPLES

I. Radiation Protection
Materials and Methods:
Mouse Total Body and Thoracic Irradiation C57BL/6TAC mice were obtained from Taconic Farms, and C57BL/6 luciferase+ mice were obtained from Steve Thorne, University of Pittsburgh Cancer Institute and housed 5 per cage according to Institutional IACUC protocols. Total body irradiation and transplantation of luciferase+ (luc+) marrow was performed For lung irradiation, mice were irradiated to the thoracic cavity with shielding of the head and neck region and abdomen and lower body according to published methods. Animals received 20 Gy single fraction thoracic irradiation and were then maintained according to IACUC directed laboratory conditions. Mice were sacrificed at serial time points after thoracic irradiation including pre-irradiation, days 2, 7, 14, 28, 50, 75, 100, 110, 150 and 200 post-irradiation. Lungs were removed and sagittal sections assayed for percent of lung replaced by fibroblasts and organizing alveolitis according to published methods. Representative lung lobes from the same animals were tested by RT-PCR for level of detectable message for inflammatory cytokines, redox sensitive promoters, and levels of MnSOD.
In Vitro Radiation Survival Curves The murine C57BL/6 bone marrow stromal cell line (Epperly M W, Sikora C A, Defilippi S, Gretton J E, Greenberger J S. Bone marrow origin of myofibroblasts in irradiation pulmonary fibrosis. Am J Resp Molecular Cell Biology 2003; 29:213-224) and its use in clonogenic radiation survival curves has been described (Epperly M W, Gretton J E, Bernarding M, Nie S, Rasul B, Greenberger J S. Mitochondrial localization of copper/zinc superoxide dismutase (Cu/ZnSOD) confers radioprotective functions in vitro and in vivo. Radiation Research 2003; 160:568-578).
Cell Line and Animal Irradiation Cell lines were irradiated at dose rate of 70 cGy per minute using a Cesium Gamma Cell Irradiator according to published methods. Clonogenic survival curve assays with bone marrow stromal cell lines were carried out according to published methods.

Mice were irradiated using JL Shepherd Mark 1 Model 68 irradiator to 9.25 total body irradiation dose or a Varian Linear Accelerator (Varian Medical Systems, Inc, Palo Alto, Calif.) to 20 Gy for pulmonary irradiation according to published methods (2, 10, 13).
Small Molecule Radiation Protector and Mitigator Drugs The GS-nitroxide JP4-039 has been described previously (Published U.S. Patent App. US 2010/0035869).
Separation of Different Cellular Components of the Mouse Lung To isolate different cellular compartments of the lung, mice were sacrificed and the pulmonary cavity was opened, and lungs perfused by injecting 5 ml of phosphate-buffered saline (PBS) into the right ventricle of the heart. To isolate pulmonary endothelial cells, the lungs were filled with 1 ml of dispase (39.65 mg/ml), allowed to collapse, and then expanded with 0.5 ml of a 1% low-melt agarose, which had been stored at 45° C. in a water bath. The lungs were immediately covered with ice and incubated for 2 minutes. The lungs were then removed, placed in 4 ml of digestion buffer (trypsin 10 ml. HBSS 10 ml, dispase (62.4 mg), and collagenase I (40 mg), incubated for 45 minutes at 37° C., and placed on ice. The lungs were transferred to 7 ml of Dulbecco's modified Eagle's medium (DMEM) containing 0.01% DNA, then teased away from the airways and swirled for 5-10 min at room temperature. The resulting suspension was filtered through a 40 μm cell strainer, centrifuged at 250 g for 10 min at 4° C., and resuspended in 10 ml of DMEM. A PE-anti-platelet endothelial cell adhesion molecule (PE-CAM) monoclonal antibody and an APC-Cy7-anti CD45 monoclonal antibody were added to the cells and incubated for 30 mins at 4° C. The cells were washed in DMEM media, DAPI was added to identify live cells. The cells were analyzed by flow cytometry with PECAM+ endothelial cells and PECAM− and CD45− cells alveolar cells isolated.
Measurement of Levels of Gene Transcripts for Irradiation Inducible Promoters, Growth Factors, Inflammatory Cytokines, Adhesion Molecules microRNA, and Bromodomain Epigenetic Reader Proteins by RT-PCR RNA was extracted from mouse lung or purified cell populations using the TRIzol reagent (Invitrogen, Carlsbad, Calif.) following the manufacturer's instructions, quantified using a spectrophotometer, and stored at −80° C. Reverse transcription of 2 μg of total RNA to complementary DNA (cDNA) was accomplished using the High Capacity cDNA Reverse Transcription Kit (Applied Biosystems, Foster City, Calif.) according to the manufacturer's protocol.

In subsequent steps, expression of GUSB (Gen-Bank: NM_010368.1), NF—KB (Gen-Bank: NM_199267.2), TNF-α (Gen-Bank: NM_013693.2), IFN-γ (Gen-Bank: NM_008337.3), Nrf2 (Gen-bank: NM_010902.3) (21), NF—KB (Gen-Bank: NM_008689.2), JUN (Gen-Bank: NM_010591.2), SP-1 (Gen-Bank: NM_013672.2), TGFβ1 (Gen-Bank: NM_011577.1), VEGFa (Gen-Bank: NM_001025250.3), IL-1a (Gen-Bank: NM_010554.4), FGF1 (Gen-Bank: NM_010197.3), IFNγ (Gen-Bank: NM_008337.3), IL-6 (Gen-Bank: NM_031168.1), FAP (Gen-Bank: NM_007986.2), vWF (Gen-Bank: NM_011708.3), CTGF (Gen-Bank: NM_010217.2) (60), Myd88 (Gen-Bank: NM_010851.2), CCL13 (Gen-Bank: NM_018866.2) (61, 67, 68), Toll Like Receptors TLR1 (Gen-Bank: NM_030682.1), TLR2 (Gen-Bank: NM_011905.3), TLR4 (Gen-Bank: NM_021297.2) (62-63), TLR5 (Gen-Bank: NM_016928.2), TLR6 (Gen-Bank: NM_011604.3), TLR7 (Gen-Bank: NM_133211.3), MnSOD (Gen-Bank: NM_013671.3), BMP2 (Gen-Bank: NM_007553.2), ADAM12 (Gen-Bank: NM_007400.2), IGFbp7 (Gen-Bank: NM_001159518.1), Bromodomain proteins BRD1 (Gen-Bank: NM_001033274.3), BRD2 (Gen- Bank: NM_001204973.1), BRD3 (Gen-Bank: NM_001113573.1), and BRDT (Gen-Bank: NM_001079873.1), and IL-12a (Gen-Bank: NM_001159424.1) was quantitated by real-time polymerase chain reaction (RT-PCR) as described (15). In addition micro-RNA's mi-RNA 107, mi-RNA 126, mi-RNA 155, mi-RNA 511, Let-7d were analyzed for expression. Ninety-six-well plates were prepared with 10 µl of Taqman Gene Expression Master mix, 5 µl R Nase-free water, 1 µl of the corresponding Taqman Gene Expression probe, and 4 µl of cDNA (totaling 2 µg cDNA) using the Eppendorf epMotion 5070 automated pipetting system (Eppendorf, Westbury, N.Y.). The cDNA was amplified with 40 cycles of 95° C. (denaturation) for 15 seconds and 60° C. (annealing and elongation) for 1 minute using the Eppendorf Realplex2 Mastercycler.

Data for each gene were normalized by calculating the differences (ΔCt) from the Ct-GUSB and Ct-Target genes. Subsequently, the relative increase or decrease in expression was calculated by comparing the reference gene with the target gene (ΔΔCt) and using the formula for relative expression ($=2^{\Delta\Delta Ct}$) Subsequently, (ΔΔCt) levels were compared and P values were calculated using one-way ANOVA followed by Tukey's multiple comparison tests.

The results were presented as fold increase in RNA above baseline levels which were adjusted to that for C57BL/6J/HNsd wild type mice. The pre-irradiation baseline levels were used to determine the magnitude of decrease or elevation in mRNA detectable by robot RT-PCR.

Live Imaging of Luciferase Positive Cells in Marrow and Lungs

C57BL/6NTac mice marrow chimeric luc+ mice were prepared by 9.25 Gy TBI, followed by an injection of $1\times10^7$ luc+ marrow cells 24 hours later. Subgroups of these chimeric mice were irradiated to 20 Gy to the pulmonary cavity. On day 75 following thoracic irradiation, 50% of the mice were placed on drinking water containing 100 mM MMS350. Mice in the non-chimeric group were injected intraperitoneally on day 100 after irradiation with $1\times10^6$ luc+ bone marrow stromal cells. Beginning 12 days after cell line injection (112 days after irradiation), the cell line injected mice were imaged at serial timepoints following injection of D-luciferin (Gold Biotechnology, St. Louis, Mo.) using a Xenogen IVIS 200 Imaging system and the bioluminescent signal for each mouse quantitated. As controls for thoracic irradiation, other C57BL/6NTac mice were irradiated to 20 Gy to the right hind limb and injected with luc+ bone marrow stromal cells in the same cell numbers and at the same time points used for the thoracic irradiation experiment. Animals were imaged for luc+ cell migration into irradiated hind limbs using methods identical to that used for pulmonary irradiation groups. The bioluminescence of the mice treated with MMS350 in the drinking water was compared to mice on regular drinking water using a Student T test.

Pulmonary Histopathology

Lungs from irradiated and luc+ cell line injected mice were removed and serial sectioned. Sections were stained for luc+, GFP+ cells, BrdU incorporation, and for quantitation of percent lung replaced by fibrosis (organizing alveolitis) according to published methods.

Radiation Mitigator Drug Administration

Mice were injected intra-peritoneally with MMS350 or JP4-039 (GS-nitroxide) in 50% cremphor/50% ethanol according to published methods. For long-term administration of MMS350, the drug was administered in water bottles with bottles changed every 7 days. The dose of drug per bottle was 100 µM MMS350 starting on day 88. The estimated total amount consumed by each animal daily was 10.9 µg based on a mouse drinking 5 ml of water per day. Chimeric mice irradiated to the thoracic cavity were placed 30 days later on MMS350 in water containing 100 mM MMS350. On day 88 after thoracic irradiation of non-chimeric mice, mice were placed on 100 mM MMS350 in drinking water.

Results:

MMS350 is a Water Soluble Radiation Protector and Mitigator.

Figures 12A, 12B:
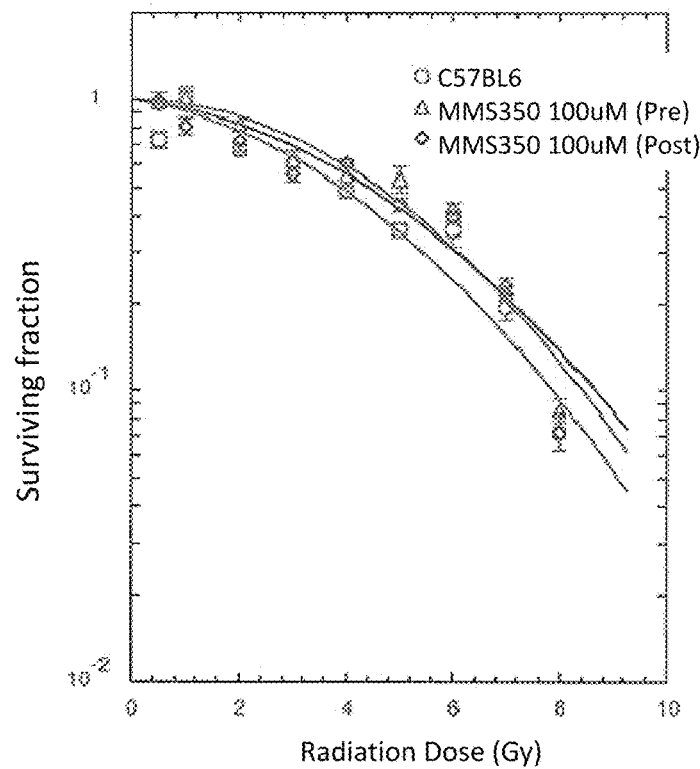
FIG. 12A is a graph of surviving fraction versus radiation dose, illustrating the in vitro radioprotection and mitigation of bone marrow stromal cells. In vitro survival curves were performed using a bone marrow stromal cell line derived from C57BL/6NTac mice. Cells were incubated in 100 µM MMS350 for one hour before irradiation or was added to the cells 10 min after irradiation. Cells were irradiated to doses ranging from 0 to 8 Gy, plated in 4 well tissue culture plates, incubated for 7 days at 37° C. in a humidified $CO_2$ incubator, and stained with crystal violet. Colonies of greater than 50 cells were counted and analyzed using a linear quadratic model or single-hit, multi-target model. Cells incubated in MMS350 before irradiation were more resistant to irradiation as seen by an increased shoulder on the survival curve (ñ=14.9±2.9 compared to 5.8±1.1 for control cells, p=0.0039). Cells administered MMS350 following irradiation also were more radioresistant as demonstrated by an increased $D_0$ (2.4±0.3 compared to 1.9±0.1 for control cells, p=0.0444).
FIG. 12B is a table comparing the shoulders of the survival curves (ñ) from FIG. 12 A.
Figure 13:
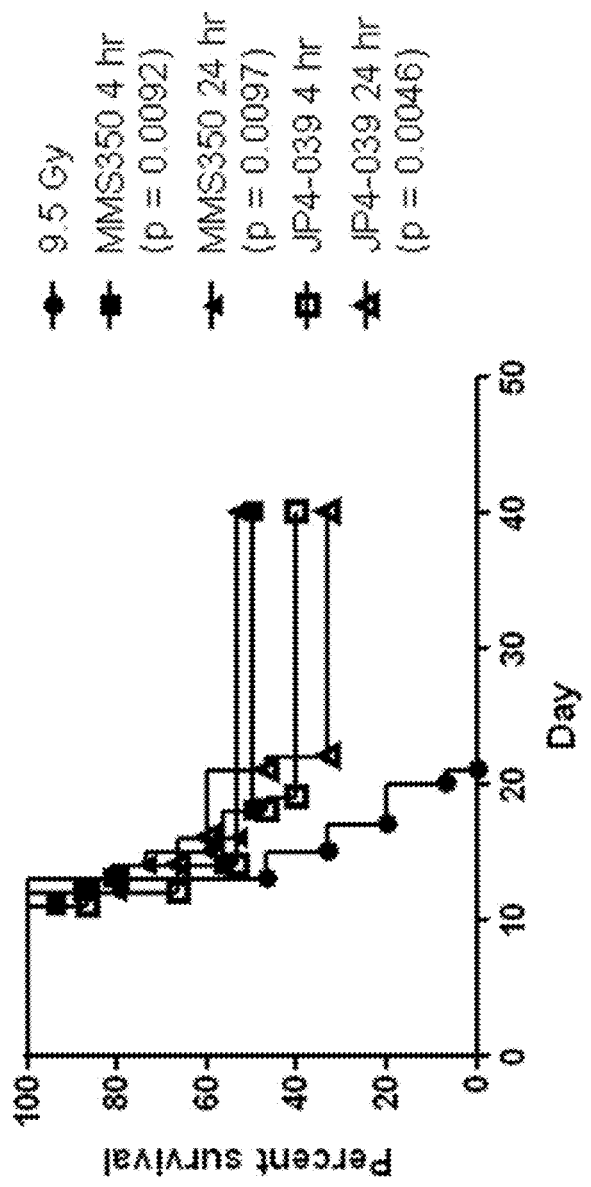
FIG. 13 is a graph of percent survival versus day, illustrating the in vivo mitigation of total body irradiation by MMS350. MMS350 was dissolved in water at a concentration of 2 mg/ml. C57BL/6NTac mice (n=15/group) were irradiated to 9.5 Gy total body irradiation and injected intraperitoneally with 10 mg/kg of MMS350 at 4 or 24 hours after irradiation. The mice were followed for the development of the hematopoietic syndrome at which time the mice were sacrificed. Mice administered MMS350 at either 4 or 24 hours after irradiation had significantly increased survival (p=0.0092 and 0.0097, respectively) compared to 10 mg/kg JP4-039 at 24 hours.

MMS350 was protective and mitigative for a C57BL/6 bone marrow stromal cell line cells in vitro (FIGS. 12A and 12B) and mitigated mice against death from the hematopoietic syndrome in 9.5 Gy total body irradiated C57BL/6NTac mice (FIG. 13).

Luciferase Bone Marrow Chimeric Mice Demonstrate Pulmonary Migration of Marrow Cells During the Onset of Fibrosis, which is Ameliorated by MMS350.

The hypothesis that serial time live imaging of luc+ marrow chimeric mice would correlate the timing of marrow migration to the lungs, with the onset of elevation of chronic pulmonary fibrosis related mRNA transcripts in the lung and endothelial cells, was tested.

Luciferase (luc+) chimeric mice were prepared by total body irradiation according to Materials and Methods, and then at day 63 were irradiated to thoracic cavity to either 18 or 20 Gy according to published methods.

Figure 14:
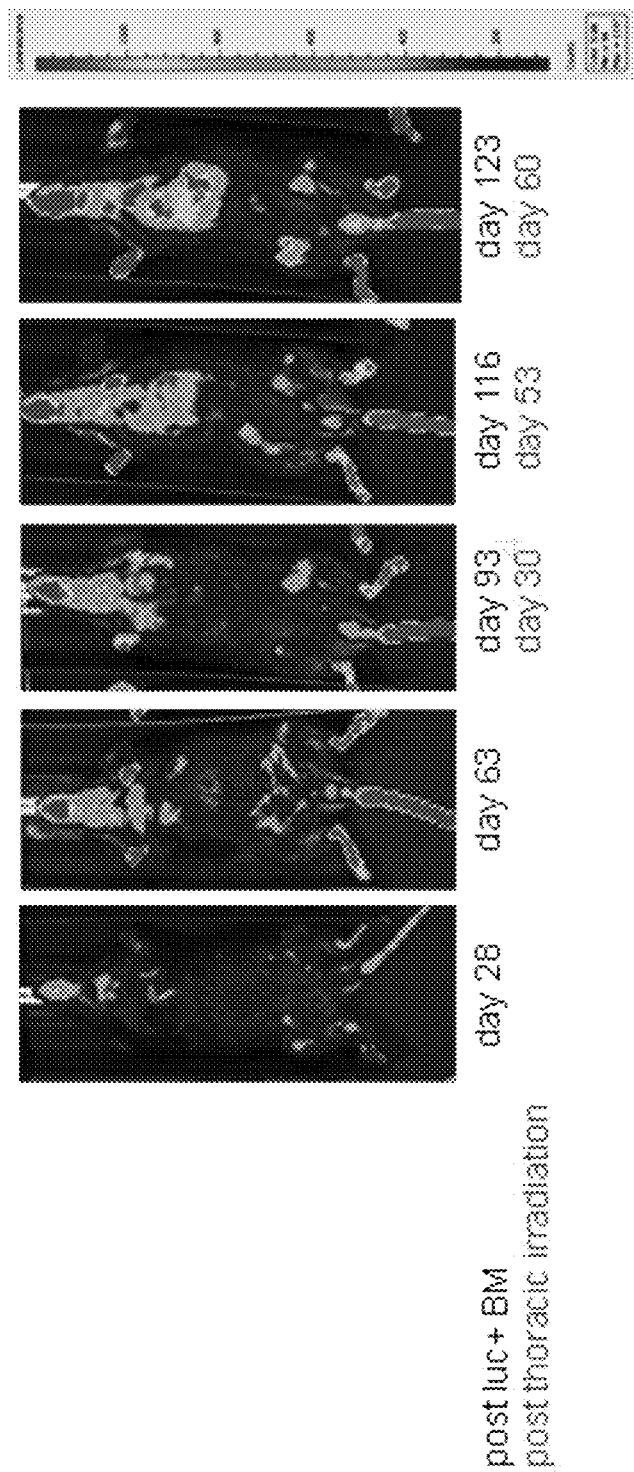
FIG. 14 provides photographs illustrating the pulmonary migration of luc+ marrow cells to irradiated lungs of luc+ chimeric mice. Groups of 30 C57BL/6Tac mice were given 10 Gy TBI then 24 hours later $1 \times 10^7$ luc+ bone marrow cells I.V. At day 63, subgroups received 18 Gy thoracic irradiation. Total body irradiated, luc+ bone marrow chimeric mice demonstrated marrow cavity specific bioluminescence (day 28) and no specific pulmonary concentration of luc+ cells until 60 days after thoracic irradiation (day 123 post luc+ cells). Mice were serially imaged for luciferase, as described in the methods.

As shown in FIG. 14, total body irradiated, luc+ bone marrow chimeric mice demonstrated marrow cavity specific bioluminescence (day 28) and no specific pulmonary concentration of luc+ cells until 60 days after thoracic irradiation (day 128). These results were obtained in multiple experiments. These results confirm and extend experiments with GFP+ marrow transplanted mice showing marrow cell migration to the lungs at the time of onset of pulmonary fibrosis. With luc+ marrow chimeric mice that received 18 Gy or 20 Gy to the thoracic cavity at day 63, subgroups that were placed on MMS350 in the drinking water showed reduction of luc+ areas in the thoracic cavity at day 123 and day 128 post-marrow transplantation (days 60 and 65 post-thoracic irradiation).

MMS350 Administration Decreases Luciferase+ Bone Marrow Stromal Cell Homing and Proliferation in Irradiated Lung.

Figure 15A:
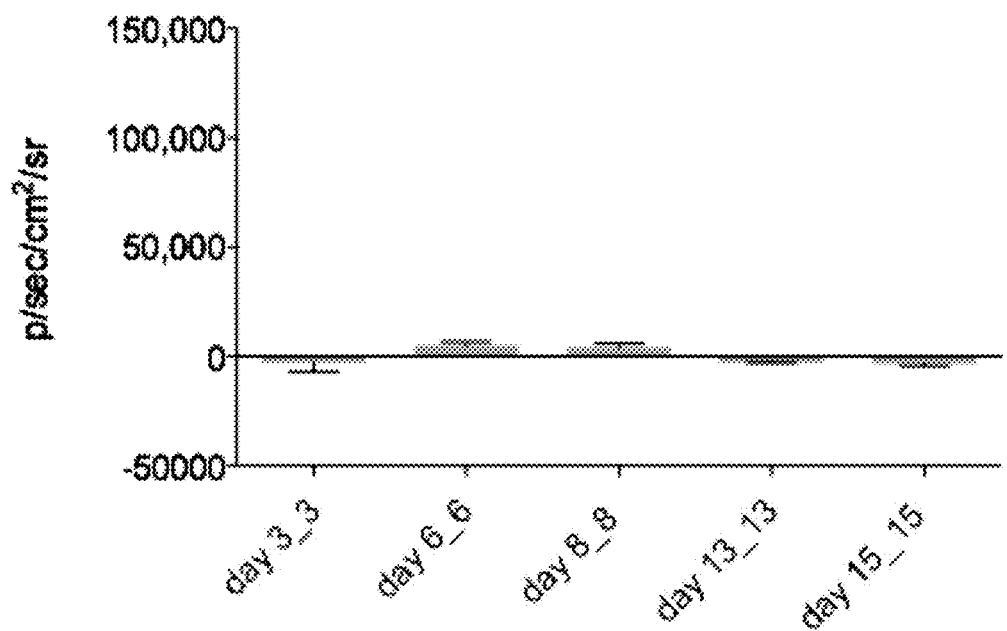
FIG. 15A is a graph illustrating that in vivo imaging revealed little or no migration of luc+BM stromal cells to the lungs of 20 Gy thoracic irradiated mice on days 3-15 post irradiation, during the acute phase.
Figure 15B:
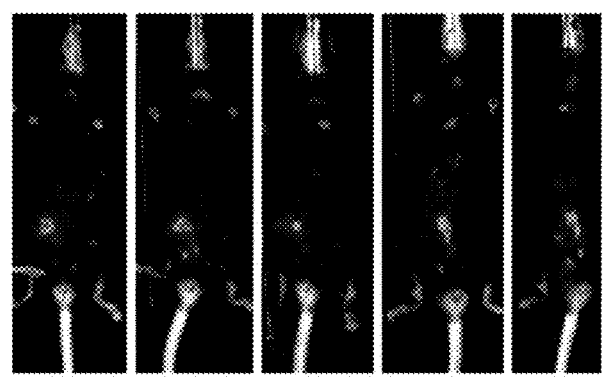
FIG. 15B is a photograph of the in vivo images corresponding to the data presented in FIG. 15A.
Figure 15C:
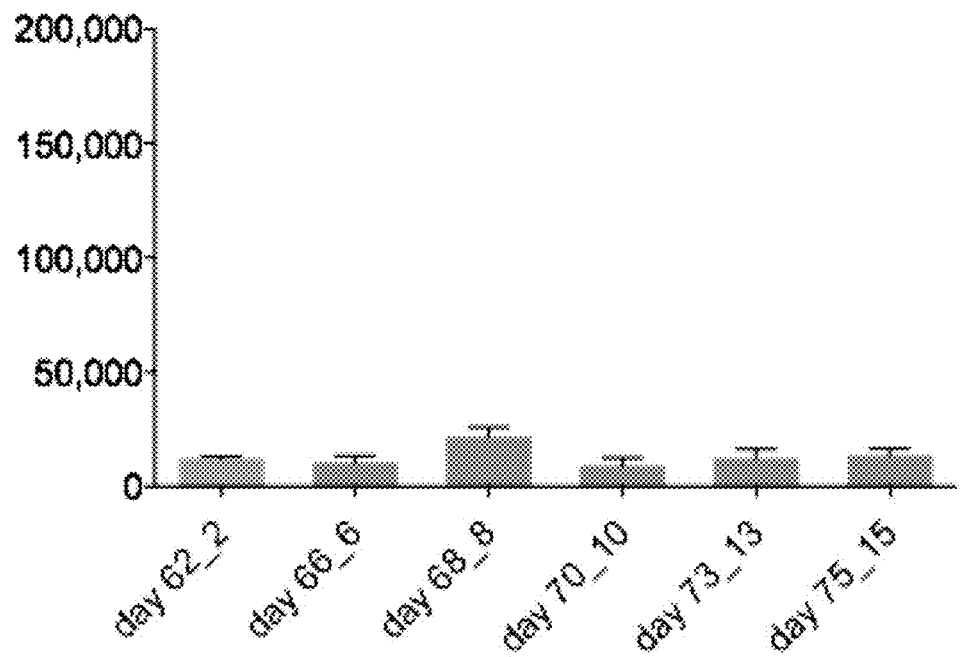
FIG. 15C is a graph illustrating that in vivo imaging revealed little or no migration of luc+ BM stromal cells to the lungs of 20 Gy thoracic irradiated mice on days 60-75 post irradiation, during the latent period.
Figure 15D:
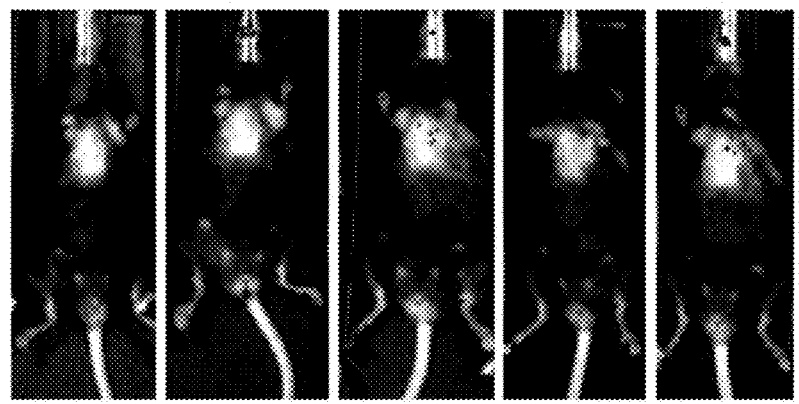
FIG. 15D is a photograph of the in vivo images corresponding to the data presented in FIG. 15C.
Figure 16A:
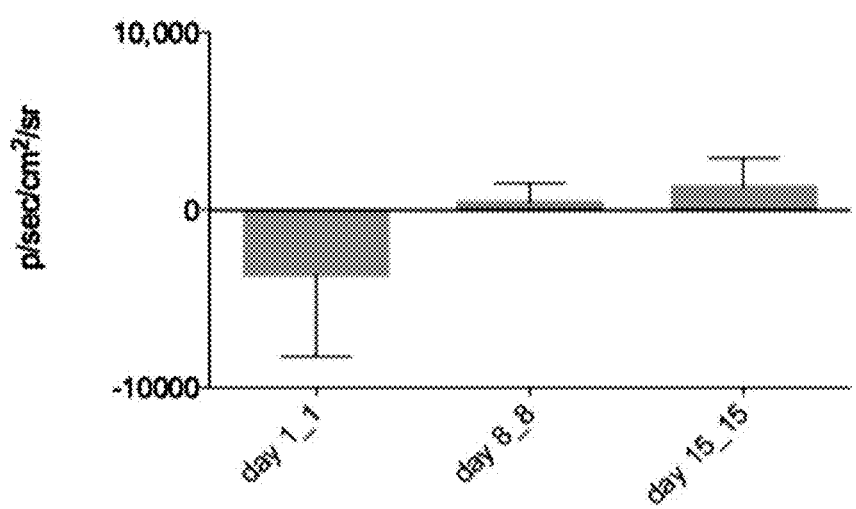
FIG. 16A is a graph illustrating that in vivo imaging revealed no migration of 1×10$^6$ luc+BM stromal cells on days 1-15 post 20 Gy to the right hind leg.
Figure 16B:
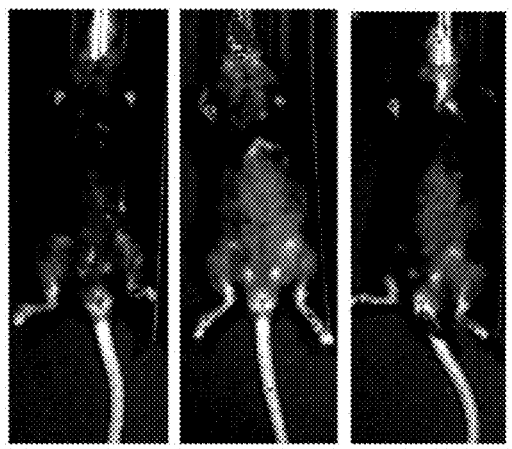
FIG. 16B is a photograph of the in vivo images corresponding to the data presented in FIG. 16A.
Figure 16C:
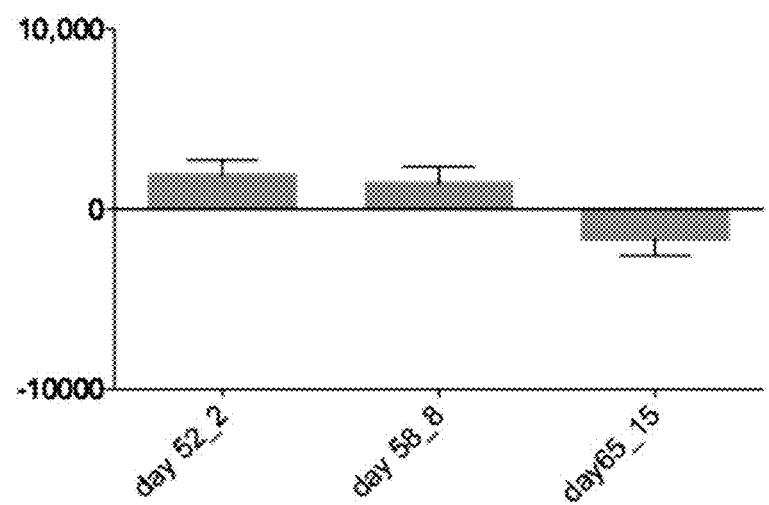
FIG. 16C is a graph illustrating that in vivo imaging revealed no migration of 1×10$^6$ luc+ BM stromal cells on days 52-65 post 20 Gy to the right hind leg.
Figure 16D:
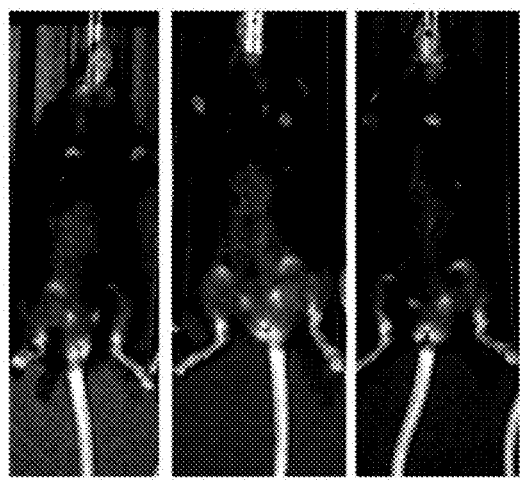
FIG. 16D is a photograph of the in vivo images corresponding to the data presented in FIG. 16C.
Figure 16E:
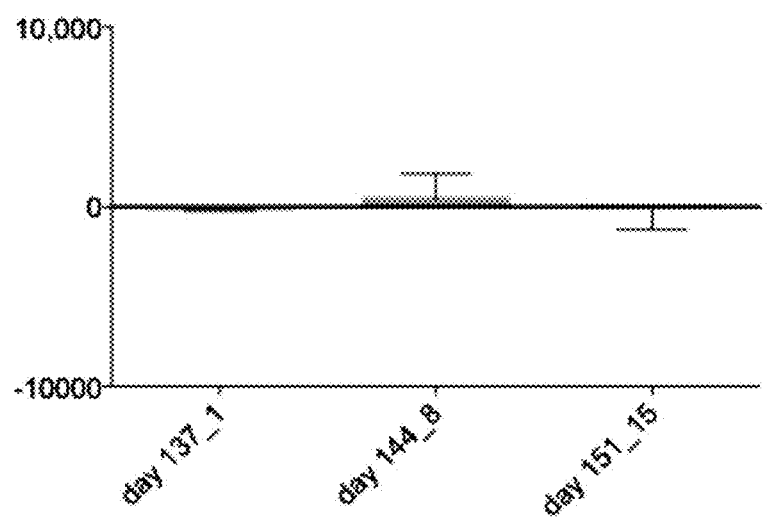
FIG. 16E is a graph illustrating that in vivo imaging revealed no migration of 1×10$^6$ luc+ BM stromal cells on days 140-155 post 20 Gy to the right hind leg.
Figure 16F:
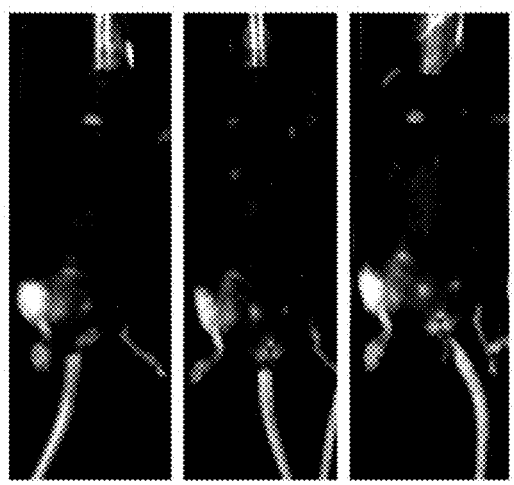
FIG. 16F is a photograph of the in vivo images corresponding to the data presented in FIG. 16E.

In a second established experimental model of marrow stromal cell line migration to the irradiated lung, C57BL/6NTac mice were irradiated to 20 Gy to the thoracic cavity and then held for varying intervals. At day 3, 60, or 127, subgroups of mice received intraperitoneal injection of $2\times10^6$ (FIGS. 15A-15F) cells from a luc+ bone marrow stromal cell line that was established from C57BL6-luc+ GFP+ marrow using published methods. As shown in FIGS. 15A-15D, there was no significant accumulation of luc+ cells in the lungs of mice injected at day 3 (FIGS. 15A and 15B) or day 60 (FIGS. 15C, 15D). In marked contrast, mice injected at day 127 showed significant migration of luc+ cells to the lungs (FIGS. 15E and 15F). That the migration was lung specific was confirmed in mice irradiated to the hind leg and held for equal intervals before injection of the same luc+ cell line and showing no cell migration to the irradiated limb (FIGS. 16A-16F). The luc+ cells migrating to the lungs were proliferating in the lung as shown by simultaneous BUDR labeling in luc+ cells (FIG. 17). The results were more prominent in mice receiving the higher cell number of bone marrow stromal cells, also migrating from the peritoneal cavity to the lungs.

Irradiation Induced Elevation of Pulmonary Gene Transcripts in Whole Lung.

Figure 18A:
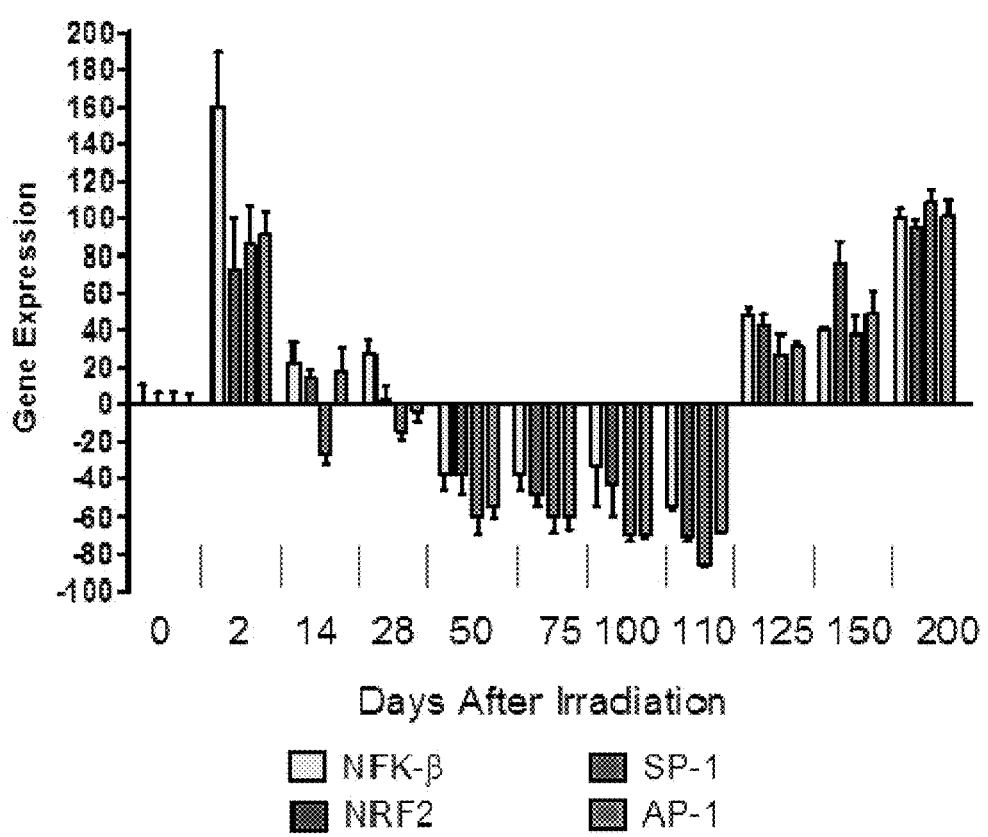
FIG. 18A is a graph of gene expression versus days after irradiation, illustrating the irradiation induction of mRNA by RT-PCR for acute phase reacting transcript genes.

Expression of three categories of gene transcripts associated with ionizing irradiation effects on the whole lung was initially evaluated. As shown in FIG. 18A, transcripts associated with the acute pulmonary radiation reaction between days 1 and 14 included inflammatory cytokine (IL-1, TNF-α, TGF-β) and transcripts for promoters associated with oxidative stress (Nrf2), and DNA damage (NFK—B). Transcripts for acute phase associated gene activation products fell after day 14 and remained low during the latent period between days 28 and 120. The acute radiation response phase of the lung has been associated with, pneumonitis related history of pathology including alveolar cells and endothelial cell swelling, alveolar space transudates, and infiltration with inflammatory cells. Resolution of the acute phase has been associated with a latent period during which the histopathology of the lung returns to normal.

Figure 18B:
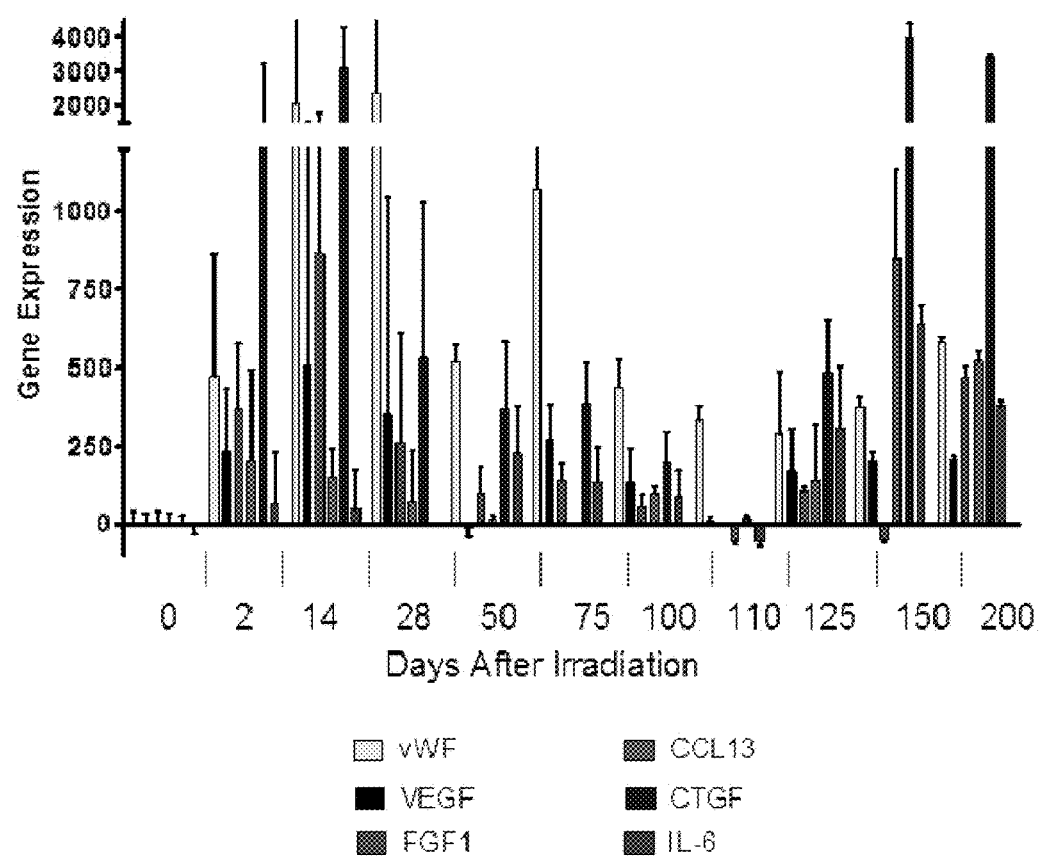
FIG. 18B is a graph of gene expression versus days after irradiation, illustrating the irradiation induction of mRNA by RT-PCR for latent period endothelial specific genes and late fibrotic period transcript genes.
Figure 18C:
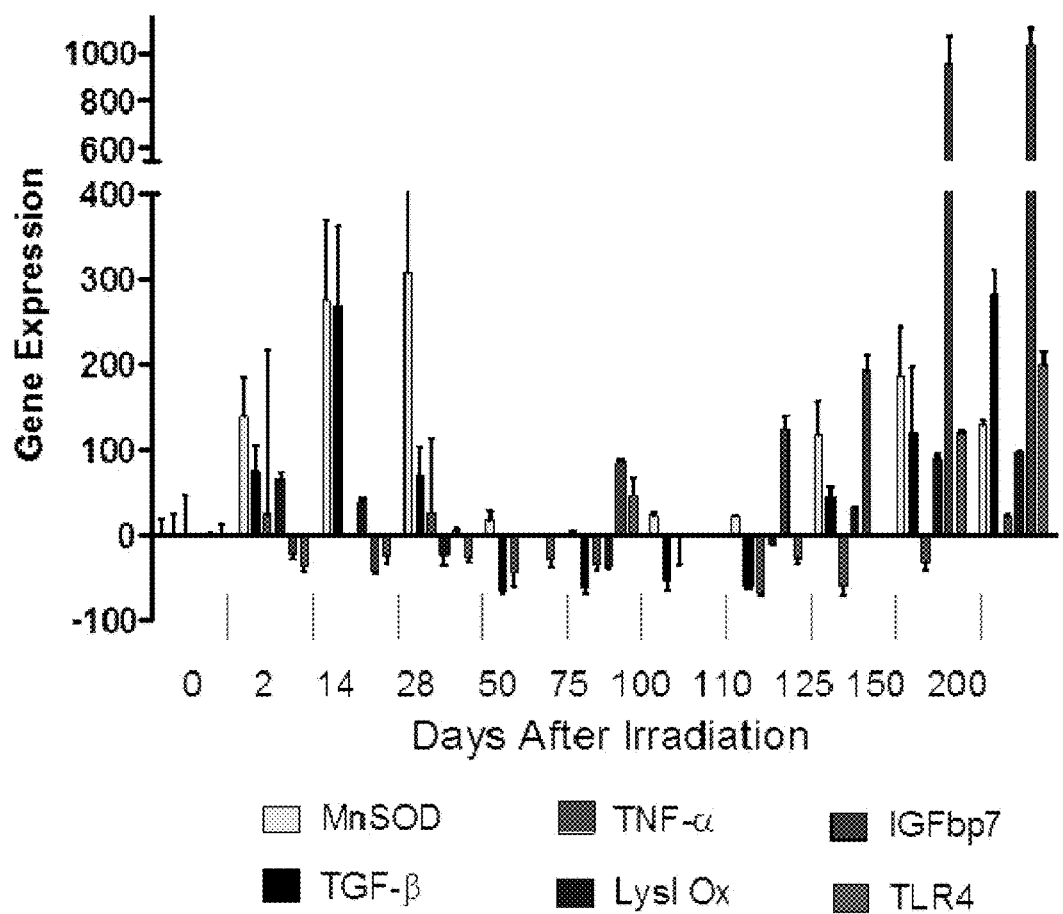
FIG. 18C is a graph of gene expression versus days after irradiation, illustrating the irradiation induction of mRNA by RT-PCR for late fibrotic period transcript genes including TGF-β, IGFbp7, MnSOD, TNF-α, lysl-oxidase, and TLR4.

During the latent period, a different pattern of gene transcript expression was detected in endothelial cell specific genes. As shown in FIG. 18B, endothelial cell associated gene transcripts remained elevated during the latent period (vWF, VEGF, FGF1) as well as CTGF and IL-6. Endothelial cell associated transcripts remained elevated after initial induction during the acute phase well into the latent period unlike inflammation associated transcripts (TGF-β, TNF-α, and MnSOD), which fell to baseline (FIG. 18C).

The late, fibrotic phase of irradiation induced pulmonary damage has been associated with a secondary elevation of some of the gene products initially identified during the acute phase. As shown in FIG. 18C, during the late fibrotic phase, after day 120 and extending out to day 200, there was elevation in expression of MnSOD, lysl oxidase, TGF-β, IGFbp7, and TLR family genes (prominently TLR4). These data establish a pattern of elevated endothelial cell associated gene transcripts during the latent period, and suggest ongoing biologic changes in the lung during a time when histopathologic changes are not identifiable.

Levels of Expression of miRNA Transcripts in Irradiated Lung Follow Established Patterns with Induction of RNA Transcripts.

Figure 19A:
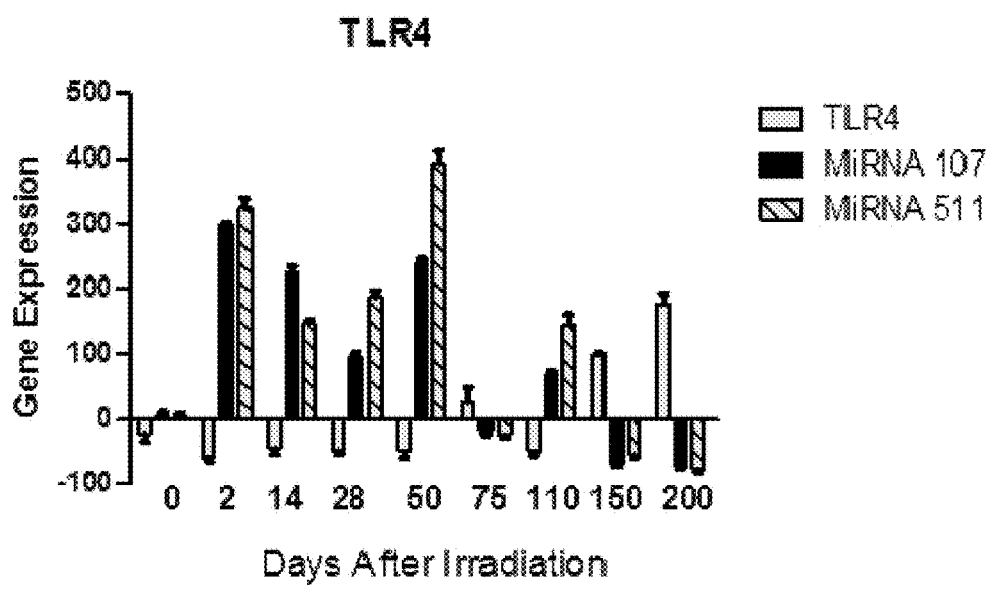
FIG. 19A is a graph of gene expression versus days after irradiation, illustrating microRNA expression of TLR4, miRNA151 and miRNA107 during acute phase, latent period, and late radiation fibrotic phase in lungs of 20 Gy irradiated mice.
Figure 19B:
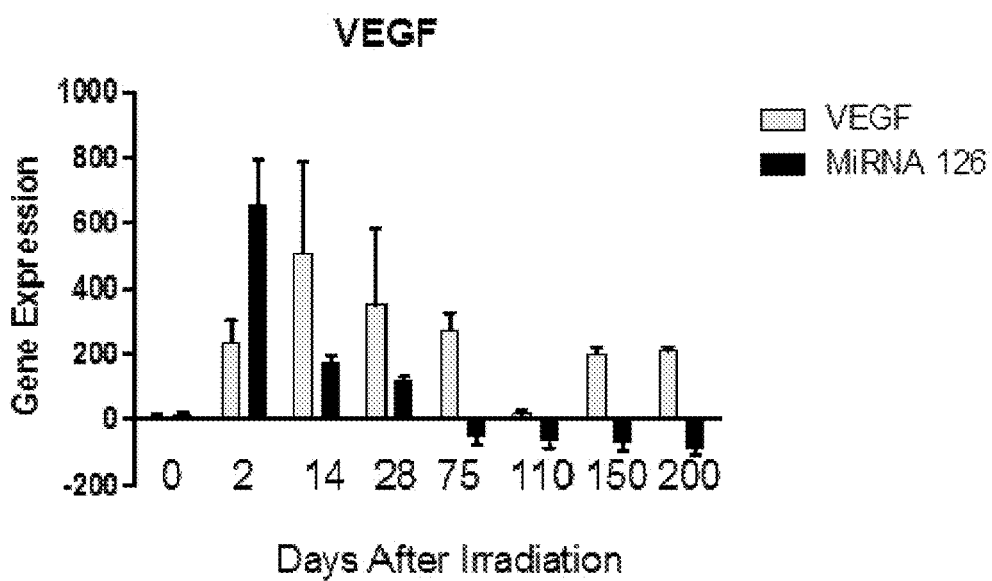
FIG. 19B is a graph of gene expression versus days after irradiation, illustrating microRNA expression of VEGF and miRNA126 during acute phase, latent period, and late radiation fibrotic phase in lungs of 20 Gy irradiated mice.
Figure 19C:
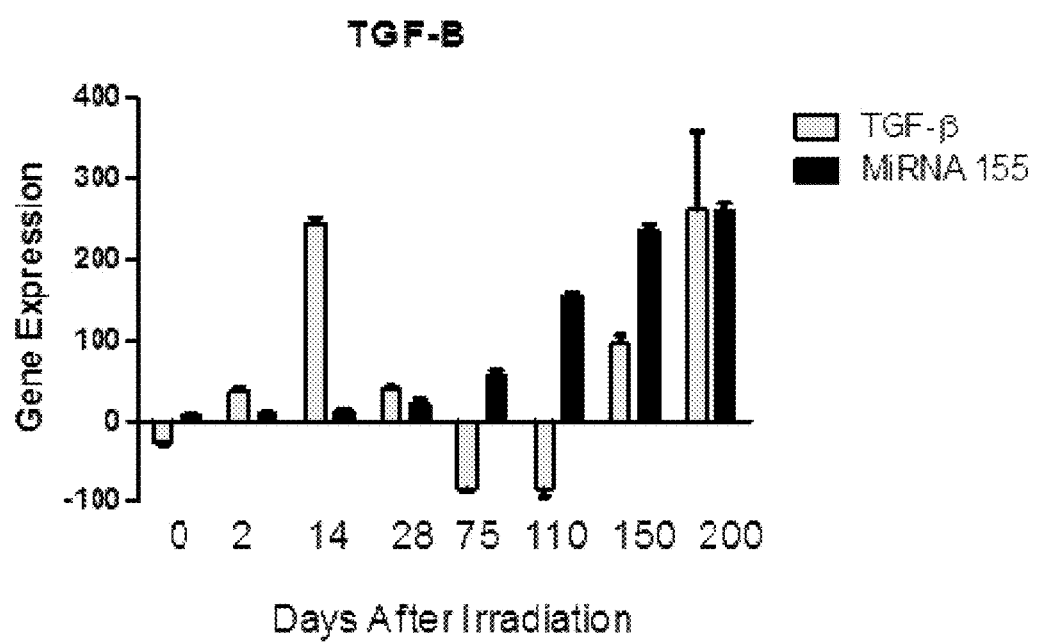
FIG. 19C is a graph of gene expression versus days after irradiation, illustrating microRNA expression of TGF-β and miRNA155 during acute phase, latent period, and late radiation fibrotic phase in lungs of 20 Gy irradiated mice.

MicroRNA transcripts have been shown to be expressed in reciprocal levels with known patterns of upregulation or downregulation of specific RNA moieties in a regulating manner. The possibility that irradiation fibrosis might be associated with an inappropriate or unsynchronized upregulation or downregulation of microRNAs was tested. Such dysregulation could explain the induction of high levels of transcripts for gene products associated with fibrosis. miRNAs associated with TLR4 (mi107 and 511) (FIG. 19A), vWF (mi126) (FIG. 19B), and with TGF-β (mi155) (FIG. 19C) were evaluated as test cases. MicroRNA Mi107, Mi511, Mi126, and Mi155 responded with levels of RNA for TGF-β, vWF, and TLR4 in expected patterns.

Therefore, the observed patterns of upregulation and downregulation of miRNAs associated with irradiation-induction of RNA for TLR4, VEGF, and TGF-β were as predicted. The data establish that irradiation altered miRNA levels, but could not explain the elevated late phase or persistent RNA expression patterns observed with TLR4, VEGF, or TGF-β.

Endothelial Cell Specific Upregulation of Gene Transcripts During the Latent Period Between Acute and Chronic Radiation Pulmonary Damage Populations of cells from the lung at several time points during the acute reaction, latent period, and chronic fibrosis phase, were separated. Endothelial cells were compared with alveolar type II cells, epithelial cells, and alveolar macrophages, and separation methods were those used in previous publications. The results shown in FIGS. 20A-20D demonstrate elevation in both alveolar and endothelial cells of NFK—B, Nrf2 (FIG. 20A), TLR4, IGFbp7 (FIG. 20B), MnSOD, TGF-β (FIG. 20C), vWF, and VEGF (FIG. 20D). These results establish that the elevations in specific transcripts include those that were endothelial cell specific (vWF and VEGF) and others seen in both alveolar and endothelial cells (TGF-β, TLR4, NFK—B). The elevation of specific transcripts was significantly greater in endothelial cells compared to alveolar cells from the same lungs.

Bromodomain Epigenetic Reader Protein Transcripts are Uniquely Elevated During the Latent Period.

The above results establish that there are clear transcriptional differences between the acute radiation pneumonitis phase, the latent period, and the late fibrosis phase in irradiated C57BL/6NTac mice. The results establish that endothelial cell specific transcripts were continually upregulated during all three phases of the radiation response in the lung in whole lung and in separated endothelial compared to the alveolar cells.

Given that very low levels of intrinsic lung cell divisions occurring prior to the onset of fibrosis (as detectable by BrdU uptake in vivo), we next searched for evidence of genetic and epigenetic changes evolving in pulmonary endothelial cells, which might explain their role in initiating migration to the lung of marrow stromal cells during the late fibrotic phase. To attempt to quantitate genetic changes, endothelial cells from lungs at 120 days after thoracic irradiation were explanted and grown in a combination of endothelial specific growth factors (VEGF, FGF1, PPGF). Cell division was monitored and testing for chromosomal aberrations by karyotype analysis of metaphase spreads was sought. A very low number of endothelial cells removed from irradiated lung attached to plastic or glass surfaces compared to cells from un-irradiated control lungs, and an even lower number went through a cell division, preventing analysis of metaphases.

Figure 21A:
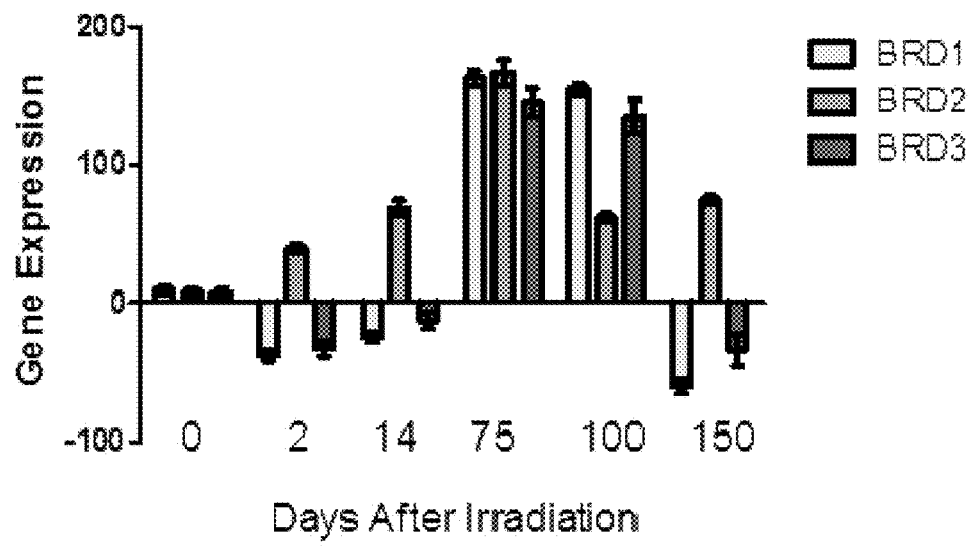
FIGS. 21A-21C provide data illustrating that MMS350 reduces irradiation induced bromodomain protein RNA transcript levels associated with the late pulmonary fibrotic phase. Mice irradiated to 20 Gy to pulmonary cavity were sacrificed at various times after irradiation. mRNA was extracted from the total lungs, endothelial cells, alveolar II cells. Expression of BD1, BD2, BD3, and BRDT was determined.
Figure 21B:
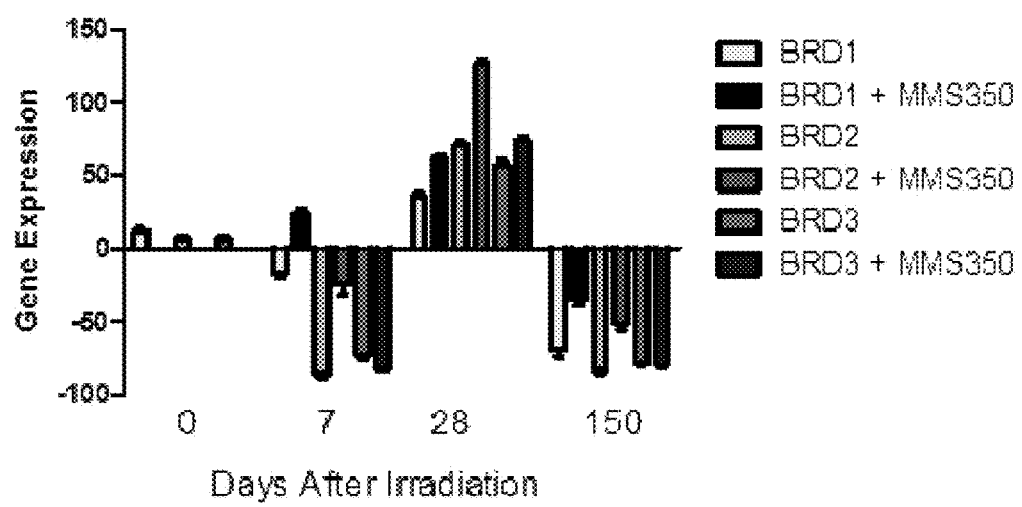
Figure 21C:
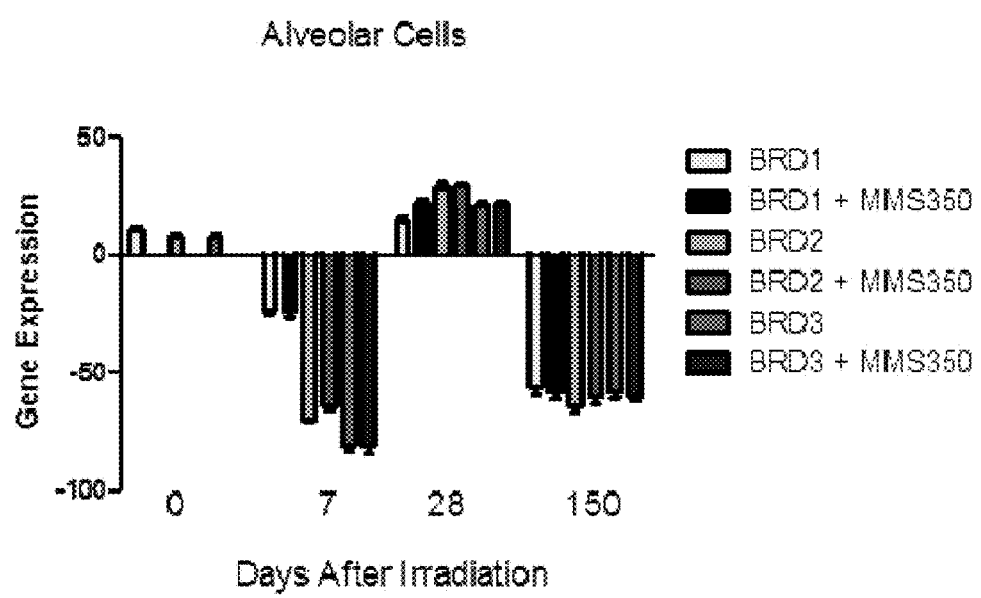

Epigenetic changes were quantitated by analysis of the expression of Bromodomain epigenetic reader proteins, as shown in FIGS. 21A-21C, there was a unique early and late fibrotic phase reduced expression of BRD1, BRD2, and BRD3 specifically in lung endothelial cells. In contrast, elevation in these transcripts during the latent period was detected in separated endothelial and alveolar cells and in whole lung. As a negative control, testes-specific BRDT protein was not detectable in any pulmonary endothelial or epithelial lung specimens. These data establish that both the acute pneumonitis-associated and late fibrosis phase of the radiation pulmonary response in C57BL/6NTac mice includes suppression of bromodomain epigenetic reader proteins.

MMS350 Reduces Expression of Genes Associated with Late Irradiation Fibrosis.

The hypothesis that administration of MMS350 continuously during the time of induction of gene transcripts associated with the fibrotic phase might reduce both gene transcription and radiation pulmonary fibrosis was tested. MMS350 at 100 μM was administered in drinking water continuously from day 80, after 20 Gy thoracic irradiation during the latent period, and throughout the fibrotic period. Mice receiving MMS350 showed decreased expression of fibrosis phase mRNA expression (FIGS. 19A-19C), and decreased associated cytokine and inflammatory marker RNA (FIGS. 20A-20D), but little effect on bromodomain transcripts, which were already low (FIGS. 21A-21C).

Endothelial and alveolar cell specific expression of fibrotic phase associated RNA was reduced by MMS350. These results establish a biomolecular correlation of the effect of the MMS350 mediated decrease in luc+ cell stromal cell migration to the lungs.

Endothelial Cells do not Release Detectable Humoral Factors that Stimulate Stromal Cell Migration In Vitro.

Figure 22:
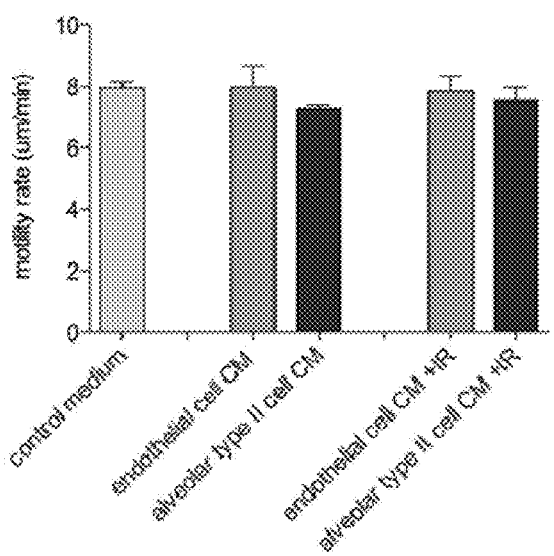
FIG. 22 is a plot of mobility rate versus medium, illustrating that the conditional medium for endothelial cells removed from 20 Gy thoracic cavity irradiated mice does not stimulate luc+ stromal cell mobility.

Endothelial cells from late fibrotic phase irradiated lung could be releasing a humoral factor that stimulated migration of stromal cells to the lungs through the circulation. Real time tracking/imaging of luc+ BM stromal cell motility in response to endothelial cell and type II alveolar cell conditioned medium (CM) was performed. Endothelial and type II alveolar cells were isolated from mouse lung on 150 post irradiation and from uniirradiated lung using flow cytometry. The isolated cells were cultured and CM was harvested after 24 hours. As shown in FIG. 22, there was no significant effect of adding CM from explanted late phase irradiated pulmonary endothelial or alveolar cells on luc+ cell motility in vitro.

MMS350 Reduced Fibrosis in Lungs of Thoracic Irradiated Mice.

Figure 23:
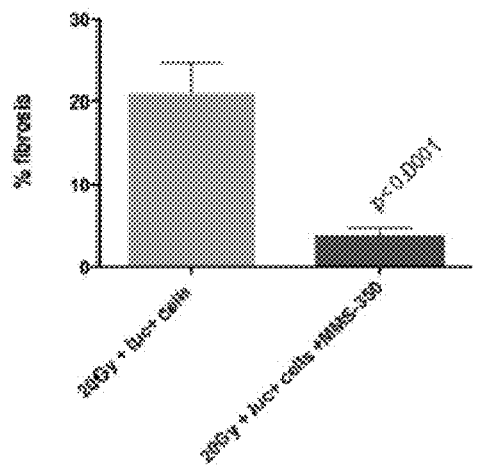
FIG. 23 is a plot of percentage fibrosis versus cells, illustrating that MMS350 in drinking water decreases fibrosis in the lungs of thoracic irradiated (20 Gy) mice.

To determine whether the MMS350 mediated changes in cell biologic and molecular biologic properties of late phase irradiation fibrosis also resulted in decreased histopathological evidence of fibrosis, we followed mice placed on MMS350 in the drinking water daily after day 80. As shown in FIG. 23, there was a significant decrease in pulmonary fibrosis in mice maintained on MMS350 compared to irradiated control mice.

The present results establish that a novel water soluble oxetanyl sulfoxide has potent radiation mitigation properties against both the total body irradiation induced hematopoietic syndrome and thoracic irradiation induced late pulmonary fibrosis. MMS350 was an effective radiation mitigator against both the LD 50/30 dose of total body irradiation in C57BL/6J/HNsd mice when administered in a single dose 24 hours after total body irradiation. MMS350 was also an effective radiation protector when administered prior to total body irradiation. Radiation mitigation was comparable to that observed with other small molecule radiation protector and mitigator drugs.

Administration of MMS350 in drinking water was effective in decreasing the severity of late radiation pulmonary fibrosis in 20 Gy thoracic irradiated mice and decreased the magnitude of pulmonary homing to and proliferation of luc+ bone marrow stromal cells, in both a marrow chimera and bone marrow stromal cell line injection. The present data confirm and extend previous publications showing marrow origin of radiation lung fibrosis using clonal green fluorescent protein positive bone marrow stromal cell lines.

The present results also establish that MMS350 reduces several biomarkers of radiation pulmonary fibrosis. Administration of MMS350 in drinking water during the latent period between days 14 and 120 after thoracic irradiation was associated with downregulation of transcription of mRNA associated with the late pulmonary fibrotic reaction including TGF-β, TLR4, and TLR7. Furthermore, explanted, separated populations of pulmonary endothelial cells from mice irradiated and treated with MMS350, showed modulation of the irradiation effect on mRNA transcripts, with some specific to pulmonary endothelial cells and others downregulated in both endothelial and alveolar type-II cells. MicroRNAs known to be associated with upregulation or downregulation of transcripts for TGF-β, and TLR4, responded inversely to irradiation and were also downregulated in mice treated with MMS350. A previous publication has shown that overexpression of miRNA-29 can reduce bleomycin induced fibrosis. The present results provide strong evidence that MMS350 is an effective radiation mitigator for late pulmonary fibrosis and acts by a mechanism that does not inappropriately alter the balance of RNA transcript regulation by specific miRNAs.

Acute and chronic ionizing irradiation induced changes in the lung represent an excellent model system in which to define the molecular and physiologic mechanisms involved during the latent period between the acute and chronic tissue damage responses. Inflammation associated transcripts were observed during both acute and fibrotic phases but not during the latent period. We investigated the molecular and cellular biomarkers linking the acute and chronic pulmonary irradiation damage phases by real time RT-PCR analysis. Endothelial cell specific levels of gene transcripts for vWF, VEGF, CCL3, IL6, and CTGF were elevated during the latent period and preceding onset of fibrosis. Migration to the lungs of luciferase+ marrow stromal cells was associated with late elevations of TLR4, TGFβ, and MnSOD all inhibited by drinking water administration of MMS350.

The present discovery of an elevation during the latent period of vWF and VEGF as well as other endothelial cell markers indicates that endothelial cells in the irradiated lung demonstrate persistent elevation in gene expression following ionizing irradiation after histopathologic markers of the acute response have subsided.

Coupled with the increased expression of endothelial markers in whole lung was elevated gene transcripts in endothelial cells compared to alveolar cells at all time points as well as increased bromodomain expression in endothelial cells. This data indicate that irradiation induced damage leading to lung fibrosis may be mediated through the endothelial cells.

Bromodomain protein transcripts also changed following pulmonary irradiation. Binding of bromodomains to DNA prevents histone deacetylation and inhibits DNA transcription. During the acute phase and late phase, there was decreased bromodomain protein transcript expression which correlates with increased gene transcription. During the latent phase, bromodomain expression increased correlated to reduction in some gene expression, but not in endothelial markers of irradiation damage where expression remained elevated. Irradiation may have released a bromodomain inhibitor during the acute and late phases.

II. Accelerated Bone Repair and/or Increased Bone Density

Figure 26:
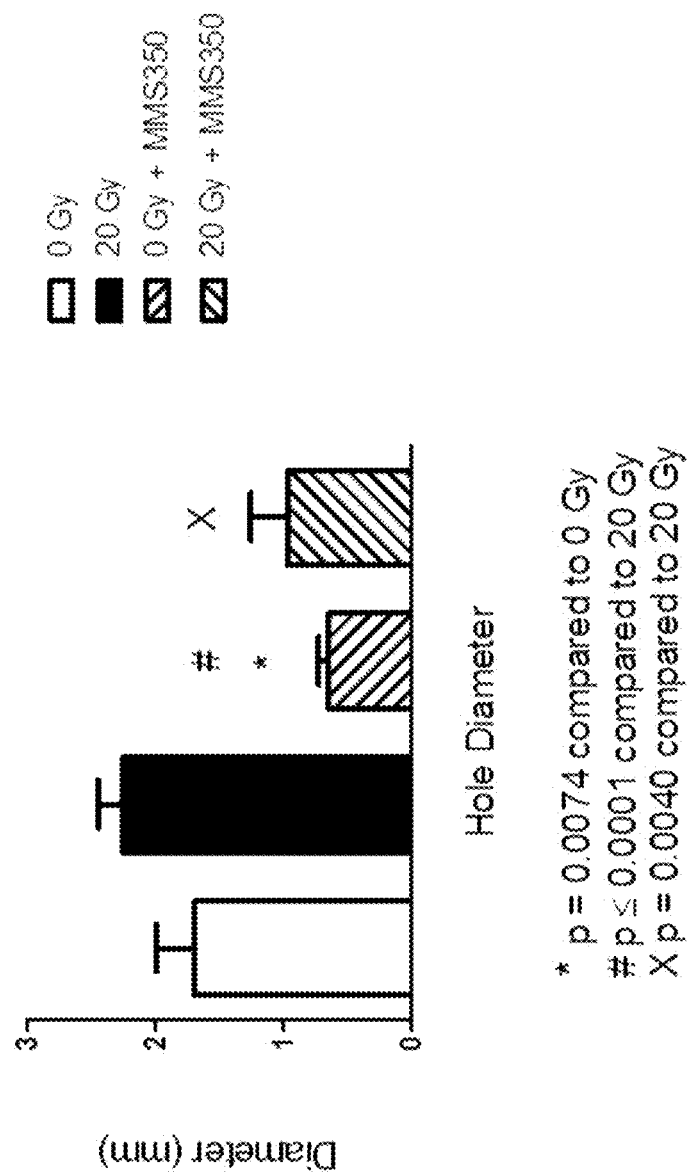
FIG. 26 is a graph of diameters of experimental bone wounds in mouse tibias after twenty one days, illustrating the increased bone healing in mice administered MMS350.
Figure 27:
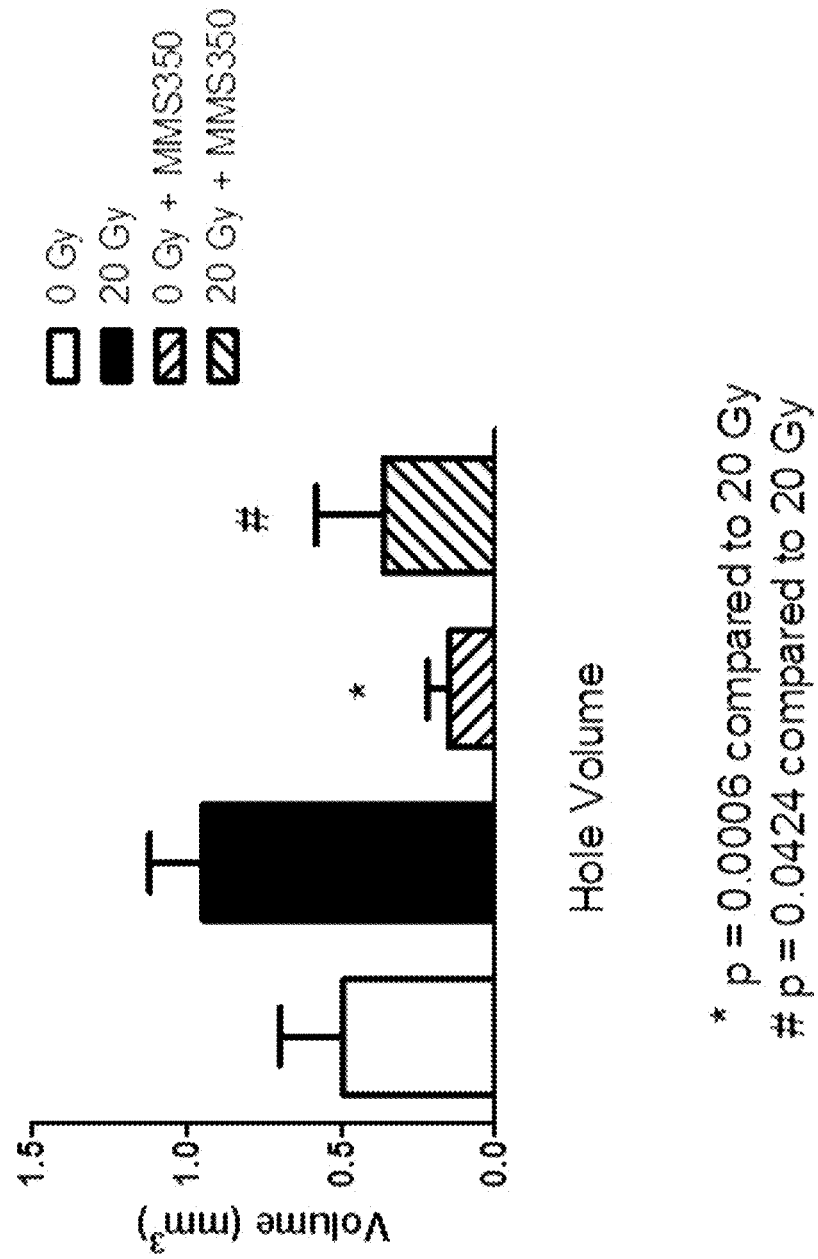
FIG. 27 is a graph of volumes of experimental bone wounds in mouse tibias after twenty one days, illustrating the increased bone healing in mice administered MMS350.

Eighteen C57BL/6NTac female mice were divided into 2 groups of 9 mice. The first group was placed on water containing 400 μM MMS350. One week later the MMS350 mice were injected IP with 20 mg/kg MMS350 in water 15 minutes before irradiation. The control mice and the MMS350 treated mice were anesthetized with Nembutal and the right hind leg was irradiated to 20 Gy with the remainder of the mouse shielded from the irradiation. Twenty-four hours later holes were drilled into the tibias of all the mice. The MMS350 treated mice were kept on the MMS350 with the water changed weekly. Twenty-one days later the mice were sacrificed and both tibias removed, and fixed. The tibias were imaged using a high resolution CT. The holes in the tibias were measured and the volume of the holes determined. The results are shown in FIGS. 26 and 27. The diameter of the 0 Gy tibia from the MMS350 group was significantly smaller than the diameter of the control 0 Gy hole (FIG. 26). Similarly, the hole in the irradiated tibia of the MMS350 group was significantly smaller than the control 20 Gy irradiated tibia (FIG. 26). Similar results were seen with the volume of the holes with the volume from the holes of the 0 Gy+ MMS350 and the 20 Gy+ MMS350 groups being significantly smaller than the volume of the hole of the control 20 Gy irradiated tibia (FIG. 27). These results demonstrated that administering MMS350 sped up bone healing in both irradiated and non-irradiated subjects.

III. Effect of MMS350 on Osteoinduction by Demineralized Bone Implants in Rats Overview Local irradiation has been used as a tool to investigate the role of neo-angiogenesis on osteoinduction by Demineralized Bone (DB). Radiation has clearly been shown to inhibit spine fusion in animal models. There is unmistakable clinical significance of post-irradiation bone grafting. In orthopedic oncology, radiation is a powerful adjunct to surgical treatments. A recent review of outcomes of treatment for metastatic spinal cord compression determined that 40 to 67% of patients undergoing pre-surgical radiation developed complications, in contrast to 33% of those who received surgery as the initial intervention. The orthopedic oncologist often sees pathologic fractures or impending fractures of irradiated bones. The most common complication seen is that of impaired wound healing and infection. Many of the complications of radiotherapy are attributable to decreased vascularity and hypoxia in affected tissues. There is compelling need for agents to mitigate the damaging effects of irradiation on bone healing and graft incorporation, and also for conditions in addition to post-irradiation skeletal reconstruction, such as in diabetes, fracture non-union, and intractable wounds.

Figure 28:
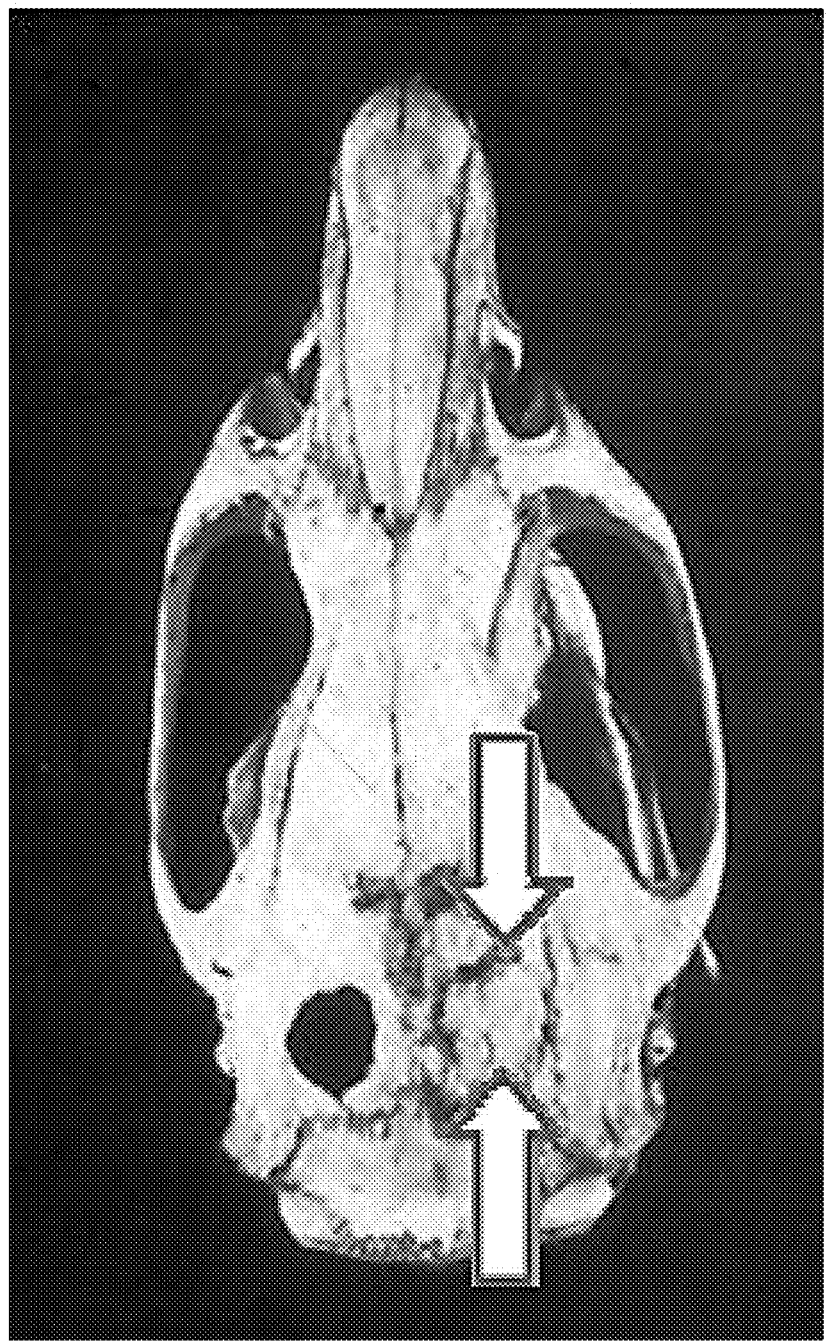
FIG. 28 is a photograph of a rat skull four weeks after implantation of Demineralized Bone Powder (DBP) into the defect created in the right parietal bone, in contrast to the defect on the left that was left empty and is clearly non-healing.

Disclosed herein is a novel water-soluble compound that mitigates the effect of irradiation to inhibit repair of calvarial defects with allogeneic rat OB. This test demonstrates that MMS350 restores osteoinduction by DBP in irradiated bone and also that MMS350 has beneficial effects in control, non-irradiated bone. The experimental model described herein is a non-healing osseous defect that is surgically constructed and is large enough to not show notable amounts of spontaneous repair. Defect models are valuable to assess efficacy of bone grafts and bone substitute materials. FIG. 28 shows an archival example of a rat skull four weeks after implantation of Demineralized Bone Powder (DBP) into the defect created in the right parietal bone, in contrast to the defect on the left that was left empty and is clearly non-healing. Extensive osteogenesis and vascularity are evident in the defect with DBP (between arrows).

The compound is tested in a defect/DBP model in rats with prior irradiation to the head. The study concerns the efficacy of systemic MMS350 to ameliorate irradiation-induced impaired DBP-induced osteogenesis and also to stimulate DBP-induced osteogenesis in control non-irradiated defects. 20 Gy irradiation is used because of its clinical significance to orthopedic oncology. An en fasse 6 MeV electron beam radiation field is used to deliver the prescribed dose of 20 Gy to calvarial bone, bolused to limited depth dose below the dura. Because there is little dose to brain and oral cavity, there is little or no mucositis. A non-healing defect is made in each parietal bone, because that affords 2 samples for analysis (one side for histology and one side for molecular), and because it avoids the dural bleeding that is often encountered when making a defect across the midline suture.

Local irradiation has known effects on bone tissue, including retardation of rat cranial and tibial growth, and mandible composition. Irradiation has deleterious effects on surgical procedures in the rodent skeleton, such as mandibular distraction osteogenesis, alveolar healing after tooth extraction, and osseous wound healing and gene therapy for defects. Subcutaneous (sc) sites are used to study the mechanisms of bone induction by DBP. Local irradiation of the sc implantation site 24 hours prior to implantation of DBP suppressed the formation of endochondral bone and marrow; osteogenesis was restored if fresh bone marrow was implanted with the DBP. Further evidence of the role of local cells was provided by a report that whole-body sub-lethal pre-irradiation impaired DBP-induced endochondral osteogenesis, but had no effect if the implantation site was shielded from pre-irradiation.

The compound disclosed herein, oxetanyl sulfoxide (MMS350, a novel, non-toxic, water-soluble radiation mitigator) protected mice from lethal total-body irradiation and decreased late radiation-induced pulmonary fibrosis (Table 6) when administered in drinking water to thoracic-irradiated mice.

TABLE 6

| Percent Pulmonary Fibrosis | |
| --- | --- |
| −MMS350 | 20.8 ± 3.9 |
| +MMS350 | 3.6 ± 1.1 |

$p < 0.0001$

Figure 29:
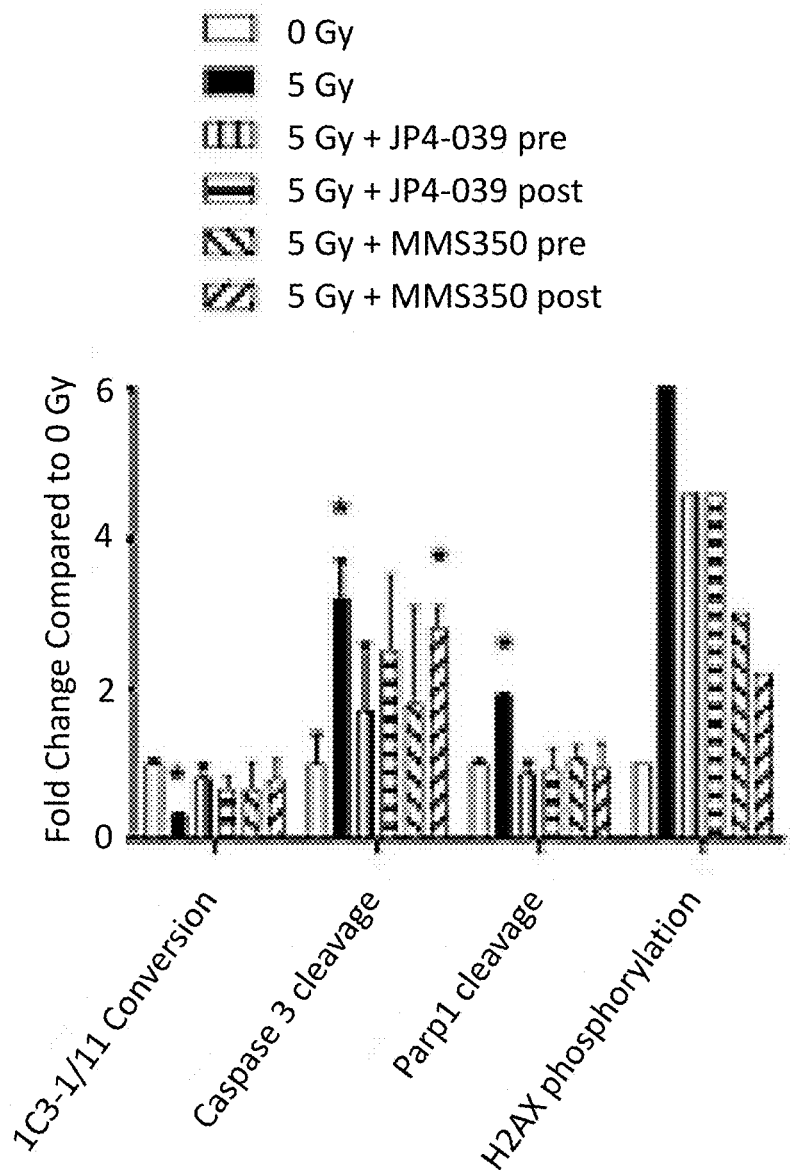
FIG. 29 is a graph of fold change compared to 0 Gy versus treatment, illustrating the effects of different treatments on apoptotic markers following irradiation.

Its mechanisms of action have been shown to include anti-oxidant and anti-apoptotic pathways (FIG. 29). FIG. 29 illustrates that MMS350 administered one-hour before or 30-minutes after 5 Gy irradiation to 320 cl 3 murine hematopoietic cells in vitro reduced mitochondrial markers of apoptosis at 24 hours after irradiation. The left-most measure (1C3-1/11 conversion) showed no difference and ruled out autophagy. Caspase-3 cleavage and Parpl cleavage illustrated the effects on apoptosis. The H2AX phosphorylation data showed that DNA strand break repair was more prominent with MMS-350 than JP4-038. These data demonstrated MMS-350's dual anti-oxidant and anti-apoptotic mechanisms.

Materials and Methods:
Overall Design of Studies (Table 7).

TABLE 7

| Number of rats needed for each experiment (6 per group) | | | |
| --- | --- | --- | --- |
| Prepare rat DBP | n = 48 | | |
| MMS/irradiated | n = 48 | ±MMS350 | 4 weekly timepoints |
| MMS/non-irradiated | n = 24 | ±MMS350 | 2 weekly timepoints |

A group of 48 CD rats is used for harvest of long bones and preparation of Demineralized Bone Powder (DBP), 75-250 μm particle size. 250 gm rats are used to determine the effects of MMS-350 on bone induction by DBP after irradiation to the skull in non-healing bilateral parietal bone defects, 5 mm in diameter. Groups of 6 anesthetized rats are positioned to receive a single dose of 20 Gy to the calvaria, with shielding of the snout and the rest of the body. After recovery, craniotomy defects are created (5-mm in diameter, one in each parietal bone), and a fixed aliquot of DBP with an amalgam carrier is placed in each defect. Rats ±irradiation and with DBP in parietal defects are treated with MMS350 in drinking water. Concentration of the MMS350 in the drinking water is maintained to achieve a daily dose of 2.5 mg per day, which is proportional to the effective dose/mg for the mouse study. And treatment begins on the day of surgery. The number of rats is further minimized by evaluating effect of MMS350 in non-irradiated rats at weeks 1 and 2, because any enhancement is achieved within that time period.

Methods

Rats are irradiated following an IACUC-approved protocol. Rats are anesthetized using Nembutal. A 6-MV linear accelerator (Varian Corp, Palo Alto) is used. The head of the rat is placed in an irradiation field of 3 cm×40 cm so that only the head is irradiated with the rest of the rat being shielded from the irradiation. The head is covered with 1.5 cm of tissue equivalent bolus to ensure homogeneity of the dose to the skull only. The skull is irradiated with electrons at a source to surface distant (SSD) of 100 cm. The rats are irradiated to 20 Gy at 3 Gy per minute. The rats are then allowed to awaken and returned to the Animal Facility.

An IACUC-approved protocol is followed for cranial surgery. The intraosseous cranial defects are constructed with an electric Dremel hand-held drill and fresh bit for each group of animals. Animals are anesthetized by Isofluane inhalation. Preoperative administration of buprenorphine (0.05-0.1 mg/kg sc) lessens intraoperative pain sensation and smooths the anesthetic course. Overlying skin is shaved and prepped. Marcaine (0.1 ml of 0.125% with epinephrine) is infiltrated into the incision region and a curved coronal incision is made posterior to the parietal bones. This location ensures that the skin wound is at a distance from the osseous defect and implant. The skin flap is reflected anteriorly and the pericranium is stripped from the parietal skull. A 5 mm diameter defect is made in each parietal bone while rinsing with Ringer's Solution. After removal of the wafer of bone, the sites are thoroughly rinsed of bone dust, and DBP is placed into each. Skin is returned to position and closed with 5 interrupted Vicryl 5.0 sutures.

Outcome Measures

Rat weights and water consumption are recorded daily. If there is early evidence of group differences in weights, pair-feeding design will be initiated. This prevents the findings from being contaminated by growth and/or nutritional effects. If differences are found in water consumption, the concentration of MMS350 in the drinking water will be recalculated to be comparable to the concentration that was effective with mice receiving whole body or thoracic irradiation. At weekly intervals to 4 weeks, rats are sacrificed for quantitative analysis of bone formed within defects.

Digital radiographs of excised parietal bones are taken with a digital FAXITRON MX-20 Specimen Radiograph System with the external cortical side facing the detector screen. The extent of bone regeneration is expressed as fractional area of newly formed bone in the defect site.

One half of the defects (right side) is processed for histological analysis of percent cartilage, bone, mineral, and vessels. Paraffin-embedment is done to enable Safranin-O stain for metachromatic cartilage matrix as red and for bone and connective tissue as green; bone architecture as woven or lamellar is identified with polarized optics. A von Kossa/H&E stain is used to identify black mineralized (calcium phosphate) foci in extracellular matrix. Immunohistological stains are useful for endothelial cell density with CD31 stain, expressed as vessel area fraction.

The other defects (left side) are processed for molecular analysis of repair tissue. RNA are isolated for quantitative gene expression analysis of markers for cartilage (Collagen type II), bone (Alkaline phosphatase, Bone Sialoprotein, Osteocalcin), vessels (vVVF), cellular proliferation (PCNA), and apoptosis (caspase, BAX, Bcl-2). Other genes of potential mechanistic interest depending on initial results include HIF-1α, VEGFα, Flt-1, TGF-β1, and TNF-α. Multiplex protein assays and RNA macroarrays may be used as well.

Data Analysis

Data are first evaluated for normality according to the Kolmogorov-Smirnov test and for equality of standard deviations with Barlett's test [Graph Pad InStat version 3.00, Graph Pad Software Inc., San Diego Calif.]. If data from each outcome measure are found to be Gaussian, statistical significance between 2 groups is tested with unpaired or paired t-tests, as appropriate, or for 3 or more groups with ANOVA. Correlations are tested with Pearson test or, for more than 2 groups, with multiple regression analysis. In the case of non-parametric data, Mann-Whitney test is used for 2 groups, Kruskal-Wallis for 3 or more, and Spearman for correlation analysis. Two-tailed p-values are always used. Based upon past performance, with the two-sided two-sample t-test with significance level of 0.05 and alpha below 0.05, a sample size of 6 replicates per group provides 99% power to detect a difference of 25%. To avoid Type II ($\beta$) error, power of each test is confirmed in post-hoc tests and sample size adjustments made if needed. If an outlier data-point is more than ±5×SD, it would be excluded.

The study addresses the following main questions:

Is there an effect of MMS350 to mitigate the inhibitory effect of local irradiation on radiographic, histologic, and molecular evidence of DBP-induced endochondral osteogenesis at 1, 2, 3, and 4 weeks after implantation of DBP into fresh calvarial defects?

Is there an effect of MMS350 to accelerate or increase radiographic, histologic, and molecular evidence of DBP-induced endochondral osteogenesis at 1 and 2 weeks after implantation of DBP into fresh calvarial defects in non-irradiated rats?

Does histologic and molecular evidence suggest mechanism(s) of action of MMS350 in this model. Is there increased cell migration across the defect? Is there increased vascularity? Are there differences in inflammatory cells and products? Is there decreased apoptosis or b=necrosis as a result of MMS350?

Expected Results

First, it is expected that 20 Gy to the skull inhibits DBP-induced endochondral osteogenesis. The dose of 20 Gy may be relevant to clinical radiotherapy. It is expected that irradiation is toxic to endothelial and/or mesenchymal cells migrating into the DBP site. Histology and molecular studies indicate a possible role of vascularization; if the cartilage phase is induced and prolonged, that may be explained by interruption of vascularization. Also, the irradiation may dampen the extent of DBP-induction.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of accelerating bone healing, bone growth, bone reconstruction, or bone repair, comprising:

selecting a subject that has, or is at increased risk of having, bone damage; and administering to the subject, a therapeutically effective amount of a compound having a formula

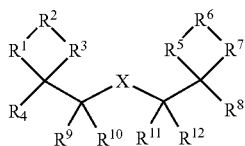

wherein
- X is S, SO or $SO_2$;
- one of $R^1$, $R^2$, and $R^3$ is O and the others of $R^1$, $R^2$ and $R^3$ are independently, the same or different, $CH_2$, or $CR^{13}$ wherein, $R^{13}$ is an alkyl group, an alkenyl group, an alkynyl group, a trialkylsilyl group, or —$(CH_2)_m OR^{15}$, wherein $R^{15}$ is an alkyl group or an aryl group and m is an integer in the range of 1 to 10, and one of $R^5$, $R^6$, and $R^7$ is O and the others of $R^5$, $R^6$ and $R^7$ are independently, the same or different, $CH_2$, or $CR^{14}$ wherein, $R^{14}$ is an alkyl group, an alkenyl group, an alkynyl group, a trialkylsilyl group, or —$(CH_2)_n OR^{16}$, wherein $R^{16}$ is an alkyl group or an aryl group and n is an integer in the range of 1 to 10;
- $R^4$ and $R^8$ are independently, the same or different, H, an alkyl group, an alkenyl group, an alkynyl group, an aryl group, a heteroaryl group, a $C_1$-$C_3$ alkoxy group, an aryloxy group, or —$(CH_2)_q OR^{17}$, wherein $R^{17}$ is an alkyl group or an aryl group and q is an integer in the range of 1 to 10, provided that $R^4$ is not a $C_1$-$C_3$ alkoxy group or an aryloxy group when $R^1$ or $R^3$ is O and $R^8$ is not a $C_1$-$C_3$ alkoxy group or an aryloxy group when $R^5$ or $R^7$ is O;
- $R^9$, $R^{10}$, $R^{11}$ and $R^{12}$ are independently, the same or different, H, an alkyl group, an alkenyl group, an alkynyl group, or an aryl group;
- wherein administration of the compound accelerates bone healing, bone growth, bone reconstruction, or bone repair.

2. The method of claim 1, wherein $R^{13}$ is a $C_1$-$C_3$ alkyl group, a $C_2$-$C_3$ alkenyl group, a $C_2$-$C_3$ alkynyl group, or a trialkylsilyl group and $R^{14}$ is a $C_1$-$C_3$ alkyl group, a $C_2$-$C_3$ alkenyl group, a $C_2$-$C_3$ alkynyl group, or a trialkylsilyl group.

3. The method of claim 1, wherein one of $R^9$ and $R^{10}$ is H and one of $R^{11}$ and $R^{12}$ is H.

4. The method of claim 1, wherein one of $R^1$, $R^2$, and $R^3$ is O and the others of $R^1$, $R^2$ and $R^3$ are $CH_2$, and one of $R^5$, $R^6$, and $R^7$ is O and the others of $R^5$, $R^6$ and $R^7$ are $CH_2$.

5. The method of claim 1, wherein X is SO.

6. The method of claim 1, wherein the compound has the formula:

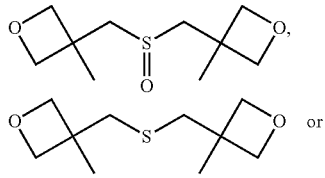

7. The method of claim 1, wherein $R^2$ and $R^6$ are each O, and $R^1$, $R^3$, $R^5$, $R^7$ are each $CH_2$.

8. The method of claim 1, wherein:
- $R^2$ and $R^6$ are each O;
- $R^1$, $R^3$, $R^5$, $R^7$ are each $CH_2$;
- $R^4$ and $R^8$ are each $C_1$-$C_{10}$ alkyl such as a methyl, ethyl, propyl, isopropyl, butyl, iso-butyl, sec-butyl, pentyl, 3-pentyl, or hexyl; and
- $R^9$-$R^{12}$ are each H.

9. The method of claim 1, wherein $R^9$—$R^{12}$ are each H.

10. The method of claim 1, wherein:
- X is SO;
- $R^2$ and $R^6$ are each O;
- $R^1$, $R^3$, $R^5$, $R^7$ are each $CH_2$;
- $R^4$ and $R^8$ are each $C_1$-$C_{10}$ alkyl such as a methyl, ethyl, propyl, isopropyl, butyl, iso-butyl, sec-butyl, pentyl, 3-pentyl, or hexyl; and
- $R^9$-$R^{12}$ are each H.

11. The method of claim 1, wherein the subject has a low bone density.

12. The method of claim 1, wherein the subject has osteoporosis.

13. The method of claim 1, wherein the subject has a bone fracture.

14. The method of claim 1, wherein the compound is administered prophylactically.

15. The method of claim 1, wherein the subject has had minimal or no exposure to radiation.

16. The method of claim 15, wherein the subject has been exposed to less than 1 Gy of radiation within 14 days of administration of the compound.

17. The method of claim 1, wherein the subject has been or is at risk of being exposed to radiation.

18. The method of claim 17, wherein the subject has been or is at risk of being exposed to from 1 to 100 Gy of radiation within 14 days of administration of the compound.

19. A method of accelerating bone healing, bone growth, bone reconstruction, or bone repair, comprising:
- selecting a subject that has, or is expected to have, bone damage; and
- administering to the subject a therapeutically effective amount of a compound having a formula

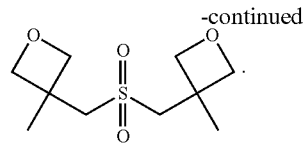

-continued

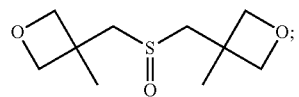

wherein administration of the compound accelerates bone healing, bone growth, bone reconstruction, or bone repair.

* * * * *